US009926560B2

(12) United States Patent
MacLachlan et al.

(10) Patent No.: US 9,926,560 B2
(45) Date of Patent: *Mar. 27, 2018

(54) LIPID ENCAPSULATING INTERFERING RNA

(71) Applicant: Protiva Biotherapeutics, Inc., Burnaby (CA)

(72) Inventors: Ian MacLachlan, Mission (CA); Lorne R. Palmer, Burnaby (CA); James Heyes, Vancouver (CA)

(73) Assignee: Protiva Biotherapeutics, Inc., Burnaby (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/936,169

(22) Filed: Nov. 9, 2015

(65) Prior Publication Data

US 2016/0115477 A1    Apr. 28, 2016

Related U.S. Application Data

(62) Division of application No. 12/852,379, filed on Aug. 6, 2010, now Pat. No. 9,181,545, which is a division of application No. 11/148,152, filed on Jun. 7, 2005, now Pat. No. 7,799,565.

(60) Provisional application No. 60/577,961, filed on Jun. 7, 2004, provisional application No. 60/578,075, filed on Jun. 7, 2004, provisional application No. 60/610,746, filed on Sep. 17, 2004, provisional application No. 60/679,427, filed on May 9, 2005.

(51) Int. Cl.
C12N 15/11     (2006.01)
A61K 9/127     (2006.01)
C12N 15/88     (2006.01)
C12N 15/113    (2010.01)
A61K 31/7105   (2006.01)
A61K 31/7088   (2006.01)

(52) U.S. Cl.
CPC .......... C12N 15/113 (2013.01); A61K 9/1272 (2013.01); A61K 31/7088 (2013.01); A61K 31/7105 (2013.01); C12N 15/111 (2013.01); C12N 15/88 (2013.01); C12N 2310/14 (2013.01); C12N 2310/351 (2013.01); C12N 2320/32 (2013.01)

(58) Field of Classification Search
CPC .............. A61K 9/1272; A61K 31/7105; A61K 31/7088; C12N 15/88; C12N 15/111; C12N 15/113; C12N 2310/14; C12N 2310/351; C12N 2320/32
USPC ....................................................... 514/44 A
See application file for complete search history.

(56) References Cited

U.S. PATENT DOCUMENTS

| 4,394,448 A | 7/1983 | Szoka, Jr. et al. |
| 4,438,052 A | 3/1984 | Weder et al. |
| 4,515,736 A | 5/1985 | Deamer |
| 4,598,051 A | 7/1986 | Papahadjopoulos et al. |
| 4,897,355 A | 1/1990 | Eppstein et al. |
| 5,013,556 A | 5/1991 | Woodle et al. |
| 5,171,678 A | 12/1992 | Behr et al. |
| 5,208,036 A | 5/1993 | Eppstein et al. |
| 5,225,212 A | 7/1993 | Martin et al. |
| 5,264,618 A | 11/1993 | Felgner et al. |
| 5,279,833 A | 1/1994 | Rose |
| 5,283,185 A | 2/1994 | Epand et al. |
| 5,320,906 A | 6/1994 | Eley et al. |
| 5,334,761 A | 8/1994 | Gebeyehu et al. |
| 5,545,412 A | 8/1996 | Eppstein et al. |
| 5,578,475 A | 11/1996 | Jessee |
| 5,627,159 A | 5/1997 | Shih et al. |
| 5,641,662 A | 6/1997 | Debs et al. |
| 5,656,743 A | 8/1997 | Busch et al. |
| 5,674,908 A | 10/1997 | Haces et al. |
| 5,703,055 A | 12/1997 | Feigner et al. |
| 5,705,385 A | 1/1998 | Bally et al. |
| 5,736,392 A | 4/1998 | Hawley-Nelson et al. |
| 5,820,873 A | 10/1998 | Choi et al. |
| 5,877,220 A | 3/1999 | Schwartz et al. |
| 5,885,613 A | 3/1999 | Holland et al. |
| 5,958,901 A | 9/1999 | Dwyer et al. |
| 5,976,567 A | 11/1999 | Wheeler et al. |
| 5,981,501 A | 11/1999 | Wheeler et al. |
| 6,020,202 A | 2/2000 | Jessee |
| 6,020,526 A | 2/2000 | Schwartz et al. |
| 6,034,135 A | 3/2000 | Schwartz et al. |
| 6,051,429 A | 4/2000 | Hawley-Nelson et al. |
| 6,075,012 A | 6/2000 | Gebeyehu et al. |
| 6,165,501 A | 12/2000 | Tirosh et al. |
| 6,172,049 B1 | 1/2001 | Dwyer et al. |

(Continued)

FOREIGN PATENT DOCUMENTS

CA    2309727 A1    4/1999
CA    2271582 A1    11/1999

(Continued)

OTHER PUBLICATIONS

Sioud et al 2003, BBRC 312; 1220-1225.*
Arpicco S. et al., "Synthesis, Characterization and Transfection Activity of New Saturated and Unsaturated Cationic Lipids." II Farmaco, Nov. 2004, vol. 59, No. 11, pp. 869-878, (ISSN 0014-827X) See Compound 13 (Scheme 1, p. 871 and section 2.2.2., p. 872), p. 876, right column, first full paragraph, Figure 3.

(Continued)

Primary Examiner — Christopher M Babic
Assistant Examiner — Kelaginamane T Hiriyanna
(74) Attorney, Agent, or Firm — Kilpatrick Townsend & Stockton LLP

(57) ABSTRACT

Rich tooling is provided for REST application development that integrates the exploration of a REST API, modeling of data types and the REST API, and the generation of artifacts using the modeled REST API and data types.

14 Claims, 32 Drawing Sheets

(56) References Cited

U.S. PATENT DOCUMENTS

| | | |
|---|---|---|
| 6,251,939 B1 | 6/2001 | Schwartz et al. |
| 6,284,267 B1 | 9/2001 | Aneja |
| 6,287,591 B1 | 9/2001 | Semple et al. |
| 6,339,173 B1 | 1/2002 | Schwartz et al. |
| 6,376,248 B1 | 4/2002 | Hawley-Nelson et al. |
| 6,534,484 B1 | 3/2003 | Wheeler et al. |
| 6,586,410 B1 | 7/2003 | Wheeler et al. |
| 6,638,529 B2 | 10/2003 | Schwartz et al. |
| 6,649,780 B1 * | 11/2003 | Eibl .............. C07C 219/08 554/103 |
| 6,670,332 B1 | 12/2003 | Wheeler |
| 6,671,393 B2 | 12/2003 | Hays et al. |
| 6,696,424 B1 | 2/2004 | Wheeler et al. |
| 6,815,432 B2 | 11/2004 | Wheeler et al. |
| 6,858,224 B2 | 2/2005 | Wheeler et al. |
| 7,148,342 B2 | 12/2006 | Tolentino et al. |
| 7,166,745 B1 | 1/2007 | Chu et al. |
| 7,422,902 B1 | 9/2008 | Wheeler et al. |
| 7,479,573 B2 | 1/2009 | Chu et al. |
| 7,514,099 B2 | 4/2009 | Chen et al. |
| 7,601,872 B2 | 10/2009 | Chu et al. |
| 7,687,070 B2 | 3/2010 | Gebeyehu et al. |
| 7,745,651 B2 | 6/2010 | Heyes et al. |
| 7,799,565 B2 | 9/2010 | MacLachlan et al. |
| 7,803,397 B2 | 9/2010 | Heyes et al. |
| 7,807,815 B2 | 10/2010 | MacLachlan et al. |
| 7,915,450 B2 | 3/2011 | Chu et al. |
| 7,982,027 B2 | 7/2011 | MacLachlan et al. |
| 8,058,068 B2 | 11/2011 | Hawley-Nelson et al. |
| 8,158,827 B2 | 4/2012 | Chu et al. |
| 8,227,443 B2 | 7/2012 | MacLachlan et al. |
| 2001/0048940 A1 | 12/2001 | Tousignant et al. |
| 2003/0069173 A1 | 4/2003 | Hawley-Nelson et al. |
| 2003/0077829 A1 | 4/2003 | MacLachlan |
| 2003/0125263 A1 | 7/2003 | Gold et al. |
| 2003/0143732 A1 | 7/2003 | Fosnaugh et al. |
| 2004/0063654 A1 | 4/2004 | Davis et al. |
| 2004/0142892 A1 | 7/2004 | Finn et al. |
| 2004/0253723 A1 | 12/2004 | Tachas et al. |
| 2004/0259247 A1 | 12/2004 | Tuschl et al. |
| 2005/0064595 A1 | 3/2005 | MacLachlan et al. |
| 2005/0118253 A1 | 6/2005 | MacLachlan et al. |
| 2005/0260757 A1 | 11/2005 | Gebeyehu et al. |
| 2006/0105976 A1 | 5/2006 | Soutschek et al. |
| 2006/0134189 A1 | 6/2006 | MacLachlan et al. |
| 2006/0147514 A1 | 7/2006 | Gebeyehu et al. |
| 2006/0228406 A1 | 10/2006 | Chiou et al. |
| 2007/0202598 A1 | 8/2007 | Chu et al. |
| 2007/0202600 A1 | 8/2007 | Chu et al. |
| 2009/0143583 A1 | 6/2009 | Chu et al. |
| 2010/0159593 A1 | 6/2010 | Chu et al. |
| 2011/0060032 A1 | 3/2011 | MacLachlan et al. |
| 2011/0262527 A1 | 10/2011 | Heyes et al. |
| 2012/0058188 A1 | 3/2012 | MacLachlan et al. |
| 2012/0136073 A1 | 5/2012 | Yang et al. |
| 2012/0202871 A1 | 8/2012 | Heyes et al. |
| 2012/0238747 A1 | 9/2012 | Chu et al. |

FOREIGN PATENT DOCUMENTS

| | | |
|---|---|---|
| CA | 2330741 A1 | 11/1999 |
| CA | 2397016 A1 | 7/2001 |
| JP | 03-126211 | 5/1991 |
| JP | 05-202085 | 8/1993 |
| JP | 06/080560 | 3/1994 |
| WO | WO 91/16024 A1 | 10/1991 |
| WO | WO 93/05162 A1 | 3/1993 |
| WO | WO 93/12240 A1 | 6/1993 |
| WO | WO 93/12756 A2 | 7/1993 |
| WO | WO 93/24640 A2 | 12/1993 |
| WO | WO 93/25673 A1 | 12/1993 |
| WO | WO 95/02698 A1 | 1/1995 |
| WO | WO 95/18863 A1 | 7/1995 |
| WO | WO 95/35301 A1 | 12/1995 |
| WO | WO 96/02655 A1 | 2/1996 |
| WO | WO 96/10390 A1 | 4/1996 |
| WO | WO 96/41873 A1 | 12/1996 |
| WO | WO 98/51285 A2 | 11/1998 |
| WO | WO 00/03683 A2 | 1/2000 |
| WO | WO 00/15820 A1 | 3/2000 |
| WO | WO 00/62813 A2 | 10/2000 |
| WO | WO 01/05374 A1 * | 1/2001 |
| WO | WO 2001/005374 A1 | 1/2001 |
| WO | WO 2001/005873 A1 | 1/2001 |
| WO | WO 02/87541 A1 * | 1/2002 |
| WO | WO 2002/034236 A2 | 5/2002 |
| WO | WO 2002/087541 A1 | 11/2002 |
| WO | WO 2003/097805 A2 | 11/2003 |
| WO | WO 2004/065546 A2 | 8/2004 |
| WO | WO 2004/110499 A1 | 12/2004 |
| WO | WO 2005/007196 A2 | 1/2005 |
| WO | WO 2005/026372 A1 | 3/2005 |
| WO | WO 2005/120152 A2 | 12/2005 |
| WO | WO 2005/121348 A1 | 12/2005 |
| WO | WO 2009/129387 A2 | 10/2009 |
| WO | WO 2009/132131 A1 | 10/2009 |
| WO | WO 2010/054401 A1 | 5/2010 |
| WO | WO 2011/000106 A1 | 1/2011 |

OTHER PUBLICATIONS

Arpicco S. et al., "Preparation and Characterization of Novel Cationic Lipids Developed for Gene Transfection." Proceed. Int'l Symp. Control Rel. Bioact. Mater., Controlled Release Society, Torchilin, V.P.; Beronese Francesco m., Eds., 1999, vol. 26, pp. 759-760.

Ballas, N. et al., "Liposomes bearing a quarternary ammonium detergent as an efficient vehicle for functional transfer of TMV-RNA into plant protoplasts," Biochim. Biophys. Acta, 1998, pp. 8-18, vol. 939.

Barinaga, M., "Step Taken Toward Improved Vectors for Gene Transfer," Science, 1994, p. 1326, vol. 266.

Bass, "The short answer," Nature, 2001, vol. 411, pp. 428-429.

Beale, G., et al. "Gene Silencing Nucleic Acids Designed by Scanning Arrays: Anti-EGFR Activity of siRNA, Ribozyme and DNA Enzymes Targeting a Single Hybridization-accessible Region using the Same Delivery System," Journal of Drug Targeting, 2003, vol. 11, No. 7, pp. 449-456.

Behr, J-P., "Synthetic Gene-Transfer Vectors," Acc. Chem. Res. 1993, pp. 274-78, vol. 26.

Brigham, K. et al., "Rapid Communication: In vivo Transfection of Murine Lungs with a Functioning Prokaryotic Gene Using a Liposome Vehicle," Am. J. Med. Sci., 1989, pp. 278-81, vol. 298.

Brummelkamp, et al. "A System for Stable Expression of Short Interfering RNAs in Mammalian Cells," Science, 2002, vol. 296, pp. 550-553.

Cas Registry; STN International, Columbus, Ohio; Registry Nos. 832075-06-6; 784136-07-8; 733738-92-6.

Cevc, G., "How Membrane Chain-Melting Phase-Transition Temperature is Affected by Lipid CHain Asymmetry and Degree of Unsaturation: An Effective Chain Length Model." Biochemestry, Jul. 1991, vol. 30, No. 29, pp. 7186-7193.

Chonn et al., "Recent advances in liposomal drug-delivery systems," Current Opinion in Biotechnology, 1995, pp. 698-708, vol. 6.

Cortesi, R., et al., "Effect of cationic liposome composition on in vitro cytotoxicity and protective effect on carried DNA," International Journal of Pharmaceutics, 1996, pp. 69-78, vol. 139.

Crystal, R., "Transfer of Genes to Humans: Early Lessons and Obstacles to Success," Science, 1995, pp. 404-410, vol. 270.

Culver K., "The First Human Gene Therapy Experiment," Gene Therapy: A Handbook for Physicians, 1994, pp. 33-40.

Duzgunes, N., "Membrane Fusion," Subcellular Biochemistry, 1985, pp. 195-286, vol. 11.

Dwarki, V.J., et al., "Cationic Liposime-Mediated RNA Transfection," Methods in Enzymology, 1993, pp. 644-54, vol. 217.

Enoch, H. et al., "Formation and properties of 1000-Å-diameter, single-bilayer phospholipid vesicles," Proc. Natl. Acad. Sci. USA, 1979, pp. 145-149, vol. 76, No. 1.

(56) References Cited

OTHER PUBLICATIONS

Felgner, J., et al., "Cationic Lipid-Mediated Transfection in Mammalian Cells: "Lipofection"," *J. Tiss. Cult. Meth.*, 1993, pp. 63-68, vol. 15.

Felgner, J.H., et al., "Enhanced Gene Delivery and Mechanism Studies with a Novel Series of Cationic Lipid Formulations," *The Journal of Biological Chemistry*, Jan. 1994, pp. 2550-2561, vol. 269, No. 4.

Felgner, P. et al., "Lipofection: A highly efficient, lipid-mediated DNA-transfection procedure," *Proc. Natl. Acad. Sci. USA*, 1987, pp. 7413-7417, vol. 84.

Felgner, P.L., et al., "Cationic Liposome Mediated Transfection," *Proc. West. Pharmacol. Soc.*, 1989, pp. 115-121, vol. 32.

Gao, X. et al., "A Novel Cationic Liposome Reagent for Efficient Transfection of Mammalian Cells," *Biochem. Biophys. Res. Comm.*, 1991, pp. 280-285, vol. 179.

Gaucheron, et al.; Transfection with fluorinated lipoplexes based on fluorinated analogues of DOTMA, DMRIE and DPPES; Biochimica et Biophysica Acta; 2002; 1564, 349-358.

Gershon, H. et al., "Mode of Formation and Structural Feature of DNA-Cationic Liposome Complexes Used for Transfection," *Biochemistry*, 1993, pp. 7413-7151, vol. 32.

Guy-Caffey, J., et al., "Novel Polyaminolipids Enhance the Cellular Uptake of Oligonucleotides " *The Journal of Biological Chemistry*, Dec. 1995, pp. 31391-31396, vol. 270, No. 52.

Hawley-Nelson, et al., "LipofectAmine™ Reagent: A New, Higher Efficiency Polycationic Liposome Transfection Reagent," *Focus*, 1993, p. 73-80, vol. 15, No. 3.

Heyes, James et al., "Cationic lipid saturation influences intracellular delivery of encapsulated nucleic acids," Journal of Controlled Release, 2005, vol. 107, No. 2, pp. 276-287.

Heyes, James et al., "Synthesis of Novel Cationic Lipids: Effect of Structural Modification on the Efficiency of Gene Transfer," J. Med. Chem., 2002, vol. 45, No. 1, pp. 99-114.

Hyde, S., et al., "Correction of the ion transport defect in cystic fibrosis transgenic mice by gene therapy," *Nature*, 1993, pp. 250-256, vol. 362.

Jaeger et al.; Preparation and Characterization of Glycerol-Based Cleavable Surfactants and Derived Vesicles; J. Am. Chem. Soc.; 1989; 111, 3001-3006.

Jiang, Lei et al.; "Comparison of protein precipitation methods for sample preparation prior to proteomic analysis"; 2004, *Journal of Chromatography*, vol. 1023, No. 2, pp. 317-320.

Juliano R., and Stamp, D., "The Effect of Particle Size and Charge on the Clearance Rates of Liposomes and Liposome Encapsulated Drugs," *Biochem. Biophys. Res. Commun.*, 1975, pp. 651-658, vol. 63.

Keough, K.M.W., "Influence of Chain Unsaturation and Chain Position on Thermotropism and Intermolecular Interactions in Membranes." Biochem. Soc. Transactions, 1990, vol. 18, No. 5, pp. 835-837.

Lawrence et al. "The formation, characterization and stability of non-ionic surfactant vesicles," S.T.P. Pharma Sciences, 1996, vol. 6, No. 1, pp. 49-60.

Lawrence et al., "Synthesis and aggregation properties of dialkyl polyoxyethylene glycol ethers," Chemistry and Physics of Lipids, 1996, 82(2):89-100.

Legendre, J.Y. and Szoka, F., "Delivery of Plasmid DNA into Mammalian Cell Lines Using pH-Sensitive Liposomes: Comparison with Cationic Liposomes," *Pharm. Res.*, 1992, pp. 1235-1242, vol. 9, No. 10.

Leventis, R., et al.,, "Interactions of mammalian cells with lipid dispersions containing novel metabolizable cationic amphiphiles," *Biochem. Biophys. Acta*, 1990, p. 124, vol. 1023.

Liu et al., "Cationic liposome-mediated intravenous gene delivery," J. Biol. Chem. 1995, vol. 270, pp. 24864-24870.

Marshall, E., "Gene Therapy's Growing Pains," *Science*, 1995, pp. 1050-1055, vol. 269.

Mashek et al. "Short Communication: Net Uptake of Nonesterified Long Chain Fatty Acids by the Perfused Caudate Lobe of the Caprine Liver," J. Dairy Sci., 2003, 86:1218-1220.

Moss et al.; Dynamics of Liposomes Constructed from Phytanyl Lipids; Tetrahedron Letters; 1990; vol. 31, No. 52, 7559-7562.

Moss, et al.; Relation of Surfactant Monomer Structure to Flip-Flop Dynamics in Surface-Differentiated Synthetic Bilayer Membranes; J. Am. Chem. Soc.; 1990; 112, 6391-6392.

Murahashi et al., "Synthesis and evaluation of neoglycolipid for liposome modification," Biol. Pharm. Bull., 1997, 20(6):704-707.

Orkin, et al., *NIH Report, Report and Recommendations of the Panel to Assess the NIH Investment in Research on Gene Therapy*, 1995.

Parr et al., Factors influencing the retention and chemical stability of poly(ethylene glycol)-lipid conjugates incorporated into large unilamellar vesicles, Biochimica et Biophysica Acta, 1994, 1195:21-30.

Paul, Cynthia P. et al.; "Effective expression of small interfering RNA in human cells"; 2002, *Nature Biotechnology*, vol. 20, pp. 505-508.

Puyal, C., et al., "A new cationic liposome encapsulating genetic material: A potential delivery system for polynucleotides," *Eur. J. Biochem.*, 1995, pp. 697-703, vol. 228.

Sawada et al., "Microemulsions in supercritical $CO_2$ utilizing the polyethyleneglycol dialkylglycerol and their use for the solubilization of hydrophiles," Dyes and Pigments, 2005, pp. 64-74, vol. 65.

Shin, et al. "Acid-triggered release via dePEGylation of DOPE liposomes containing acid-labile vinyl ether PEG-lipids," Journal of Controlled Release, 2003, vol. 91, pp. 187-200.

Sioud et al., 2003, 88RC 312:1225.

Song et al., "Characterization of the inhibitory effect of PEG-lipid conjugates on the intracellular delivery of plasmid and antisense DNA mediated by cationic lipid liposomes," Biochimica et Biophysica Acta, 2002, 1558:1-13.

Sorensen et al., "Gene Silencing by Systemic Delivery of Synthetic siRNAs in Adult Mice," J. Mol. Biol., Apr. 4, 2003, vol. 4, pp. 761-766.

Spagnou, Sebastien et al.; "Lipidic Carriers of siRNA: Differences in the Formulation, Cellular Uptake, and Delivery with Plasmid DNA"; 2004, *Biochemistry*, vol. 43, pp. 13348-13356.

Stamatatos, L., et al., "Interactions of Cationic Lipid Vesicles with Negatively Charged Phospholipid Vesicles and Biological Membranes," *Biochemistry*, 1988, pp. 3917-3925, vol. 27.

Szoka, F. et al., "Comparative Properties and Methods of Preparation of Lipid Vesicles (Liposomes)," *Ann. Rev. Biophys. Bioeng.*, 1980, pp. 467-508, vol. 9.

Szoka, F. et al., "Procedure for preparation of liposomes with large internal aqueous space and high capture by reverse-phase evaporation," *Proc. Natl. Acad. Sci. USA*, 1978, pp. 4194-4198, vol. 75, No. 9.

Templeton, "Cationic liposome-mediated intravenous gene delivery in vivo," Bioscience Reports, 2002, vol. 22, No. 2, pp. 283-295.

Van Der Woude, I., et al., "Parameters influencing the introduction of plasmid DNA into cells by the use of synthetic amphiphiles as a carrier system," *Biochimica et Biophysica Acta*, 1995, pp. 34-40, vol. 1240.

Vigh et al. "Does the membrane's physical state control the expression of heat shock and other genes?" TIBS, 1998, 23:369-374.

Wang, et al.; Preparation, Properties, and Applications of Vesicle-Forming Cleavable Surfactants with a 1, 3-Dioxane Ring; Journal of Colloid and Interface Science; 1995; 173, 49-54.

Wetzer, et al.; S-Layer Reconstitution at Phospholipid Monolayers; Langmuir; 1998; 14, 6899-6906.

Wheeler et al., Stabilized plasmid-dipid particles: construction and characterization, Gene Therapy, 1999, vol. 6, No. 271-281.

Wilson, R. et al., "Counterion-Induced Condensation of Deoxyribonucleic Acid. A Light-Scattering Study." *Biochemistry*, 1979, pp. 2192-2196, vol. 18.

Woodle, M.C. et al., "Versatility in lipid compositions showing prolonged circulation with sterically stabilized liposomes," *Biochim. Biophys. Acta*, 1992, pp. 193-200, vol. 1105.

(56) References Cited

OTHER PUBLICATIONS

Yamamura, et al.; Synthesis and Properties of Destructible Double-chain Cationic Surfactants with a 1,3-Dioxolane Ring; Kagaku to Kogyo (Osaka Japan); 1994; 68(3), 127-131.
Zhu, N., et al., "Systemic Gene Expression After Intravenous DNA Delivery into Adult Mice," *Science*, 1993, pp. 209-211, vol. 261.

* cited by examiner

LIPID ENCAPSULATING INTERFERING RNA

CROSS-REFERENCES TO RELATED APPLICATIONS

This application is a Divisional of U.S. patent application Ser. No. 12/852,379, filed Aug. 6, 2010, which is a Divisional of U.S. patent application Ser. No. 11/148,152, filed Jun. 7, 2005, which claims the benefit of U.S. Provisional Patent Application Nos. 60/577,961 filed Jun. 7, 2004, 60/578,075 filed Jun. 7, 2004, 60/610,746, filed Sep. 17, 2004, and 60/679,427, filed May 9, 2005, the disclosures of each of which are hereby incorporated by reference in their entirety for all purposes.

REFERENCE TO A "SEQUENCE LISTING," A TABLE, OR A COMPUTER PROGRAM LISTING APPENDIX SUBMITTED ON A COMPACT DISK

The Sequence Listing written in file 086399-001962US-0963783_SequenceListing.txt, created on Nov. 9, 2015, 1,226 bytes, machine format IBM-PC, MS-Windows operating system, is hereby incorporated by reference in its entirety for all purposes.

FIELD OF THE INVENTION

The present invention relates to compositions and methods for the therapeutic delivery of a nucleic acid comprising a serum-stable lipid delivery vehicle encapsulating a nucleic acid to provide efficient RNA interference (RNAi) in a cell or mammal. More particularly, the present invention is directed to using a small interfering RNA (siRNA) encapsulated in a serum-stable lipid particle having a small diameter suitable for systemic delivery.

BACKGROUND OF THE INVENTION

RNA interference (RNAi) is an evolutionarily conserved, sequence specific mechanism triggered by double stranded RNA (dsRNA) that induces degradation of complementary target single stranded mRNA and "silencing" of the corresponding translated sequences (McManus and Sharp, *Nature Rev. Genet.* 3:737 (2002)). RNAi functions by enzymatic cleavage of longer dsRNA strands into biologically active "short-interfering RNA" (siRNA) sequences of about 21-23 nucleotides in length (Elbashir, et al., *Genes Dev.* 15:188 (2001)).

siRNA can be used downregulate or silence the transcription and translation of a gene product of interest. For example, it is desirable to downregulate genes associated with liver diseases and disorders such as hepatits. In particular, it is desirable to downregulate genes associated with hepatitis viral infection and survival.

An effective and safe nucleic acid delivery system is required for interference RNA to be therapeutically useful. Viral vectors are relatively efficient gene delivery systems, but suffer from a variety of limitations, such as the potential for reversion to the wild type as well as immune response concerns. As a result, nonviral gene delivery systems are receiving increasing attention (Worgall, et al., *Human Gene Therapy* 8:37 (1997); Peeters, et al., Human Gene Therapy 7:1693 (1996); Yei, et al., *Gene Therapy* 1: 192 (1994); Hope, et al., *Molecular Membrane Biology* 15:1 (1998)). Furthermore, viral systems are rapidly cleared from the circulation, limiting transfection to "first-pass" organs such as the lungs, liver, and spleen. In addition, these systems induce immune responses that compromise delivery with subsequent injections.

Plasmid DNA-cationic liposome complexes are currently the most commonly employed nonviral gene delivery vehicles (Feigner, Scientific American 276:102 (1997); Chonn, et al., *Current Opinion in Biotechnology* 6:698 (1995)). For instance, cationic liposome complexes made of an amphipathic compound, a neutral lipid, and a detergent for transfecting insect cells are disclosed in U.S. Pat. No. 6,458,382. Cationic liposome complexes are also disclosed in U.S. Patent Publication No. 2003/0073640.

Cationic liposome complexes are large, poorly defined systems that are not suited for systemic applications and can elicit considerable toxic side effects (Harrison, et al., *Biotechniques* 19:816 (1995); Li, et al., *The Gene* 4:891 (1997); Tam, et al, *Gene Ther.* 7:1867 (2000)). As large, positively charged aggregates, lipoplexes are rapidly cleared when administered in vivo, with highest expression levels observed in first-pass organs, particularly the lungs (Huang, et al., *Nature Biotechnology* 15:620 (1997); Templeton, et al., *Nature Biotechnology* 15:647 (1997); Hofland, et al., *Pharmaceutical Research* 14:742 (1997)).

Other liposomal delivery systems include, for example, the use of reverse micelles, anionic and polymer liposomes. Reverse micelles are disclosed in U.S. Pat. No. 6,429,200. Anionic liposomes are disclosed in U.S. Patent Application No. 2003/0026831. Polymer liposomes, that incorporate dextrin or glycerol-phosphocholine polymers, are disclosed in U.S. Patent Application Nos. 2002/0081736 and 2003/0082103, respectively.

A gene delivery system containing an encapsulated nucleic acid for systemic delivery should be small (i.e., less than about 100 nm diameter) and should remain intact in the circulation for an extended period of time in order to achieve delivery to affected tissues. This requires a highly stable, serum-resistant nucleic acid-containing particle that does not interact with cells and other components of the vascular compartment. The particle should also readily interact with target cells at a disease site in order to facilitate intracellular delivery of a desired nucleic acid.

Recent work has shown that nucleic acids can be encapsulated in small (about 70 nm diameter) "stabilized nucleic acid-lipid particles" (SNALP) that consist of a single plasmid encapsulated within a bilayer lipid vesicle (Wheeler, et al., *Gene Therapy* 6:271 (1999)). These SNALPs typically contain the "fusogenic" lipid dioleoylphosphatidylethanolamine (DOPE), low levels of cationic lipid, and are stabilized in aqueous media by the presence of a poly (ethylene glycol) (PEG) coating. SNALP have systemic application as they exhibit extended circulation lifetimes following intravenous (i.v.) injection, accumulate preferentially at distal tumor sites due to the enhanced vascular permeability in such regions, and can mediate transgene expression at these tumor sites. The levels of transgene expression observed at the tumor site following i.v. injection of SPLP containing the luciferase marker gene are superior to the levels that can be achieved employing plasmid DNA-cationic liposome complexes (lipoplexes) or naked DNA.

Thus, there remains a strong need in the art for novel and more efficient methods and compositions for introducing nucleic acids, such as interfering RNA, into cells. In addition, there is a need in the art for methods of treating or preventing disorders such as hepatitis by downregulating genes associated with viral infection and survival. The present invention addresses this and other needs.

BRIEF SUMMARY OF THE INVENTION

The present invention comprises novel, stable nucleic acid-lipid particles (SNALP) encapsulating one or more interfering RNA molecules, methods of making the SNALPs and methods of deliverubg and/or administering the SNALPs.

In one embodiment, the invention provides for a nucleic acid-lipid particle comprising an interfering RNA and a cationic lipid of Formula I or II and having the following structures:

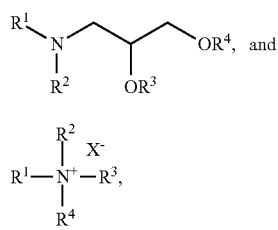

wherein $R^1$ and $R^2$ are independently selected from the group consisting of: H and $C_1$-$C_3$ alkyls; and $R^3$ and $R^4$ are independently selected from the group consisting of alkyl groups having from about 10 to about 20 carbon atoms, wherein at least one of $R^3$ and $R^4$ comprises at least two sites of unsaturation. In a preferred embodiment, that cationic lipid is selected from 1,2-DiLinoleyloxy-N,N-dimethylaminopropane (DLinDMA) and 1,2-Dilinolenyloxy-N,N-dimethylaminopropane (DLenDMA). In a preferred embodiment, the interfering RNA molecule is fully encapsulated within the lipid bilayer of the nucleic acid-lipid particle such that the nucleic acid in the nucleic acid-lipid particle is resistant in aqueous solution to degradation by a nuclease. In a preferred embodiment, the nucleic acid particle is substantially non-toxic to mammals. The nucleic acid lipid particles may further comprise a non-cationic lipid, a bilayer stabilizing component (i.e., a conjugated lipid that prevents aggregation of particles, a cationic polymer lipid, a sterol (e.g., cholesterol) and combinations thereof.

In some embodiments, the interfering RNA is a small-interfering RNA molecule that is less than about 60 nucleotides in length or a double-stranded RNA greater than about 25 nucleotides in length. In some embodiments the interfering RNA is transcribed from a plasmid, in particular a plasmid comprising a DNA template of a target sequence.

In one embodiment, the non-cationic lipid is selected from distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), a sterol (e.g., cholesterol) and a mixture thereof.

In one embodiment, the conjugated lipid that inhibits aggregation of particles is one or more of a polyethyleneglycol (PEG)-lipid conjugate, a polyamide (ATTA)-lipid conjugate, and a mixture thereof. In one aspect, the PEG-lipid conjugate is one or more of a PEG-dialkyloxypropyl (DAA), a PEG-diacylglycerol (DAG), a PEG-phospholipid, a PEG-ceramide, and a mixture thereof. In one aspect, the PEG-DAG conjugate is one or more of a PEG-dilauroylglycerol ($C_{12}$), a PEG-dimyristoylglycerol ($C_{14}$), a PEG-dipalmitoylglycerol ($C_{16}$), and a PEG-distearoylglycerol ($C_{18}$). In one aspect, the PEG-DAA conjugate is one or more of a PEG-dilauryloxypropyl ($C_{12}$), a PEG-dimyristyloxypropyl ($C_{14}$), a PEG-dipalmityloxypropyl ($C_{16}$), and a PEG-distearyloxypropyl ($C_{18}$).

The nucleic acid-lipid particles of the present invention are useful for the therapeutic delivery of nucleic acids comprising an interfering RNA sequence. In particular, it is an object of this invention to provide in vitro and in vivo methods for treatment of a disease in a mammal by downregulating or silencing the transcription and translation of a target nucleic acid sequence of interest. In some embodiments, an interfering RNA is formulated into a nucleic acid-lipid particle, and the particles are administered to patients requiring such treatment. In other embodiments, cells are removed from a patient, the interfering RNA delivered in vitro, and reinjected into the patient. In one embodiment, the present invention provides for a method of introducing a nucleic acid into a cell by contacting a cell with a nucleic acid-lipid particle comprised of a cationic lipid, a non-cationic lipid, a conjugated lipid that inhibits aggregation, and an interfering RNA.

In one embodiment, at least about 5%, 10%, 15%, 20%, or 25% of the total injected dose of the nucleic acid-lipid particles is present in plasma about 8, 12, 24, 36, or 48 hours after injection. In other embodiments, more than 20%, 30%, 40% and as much as 60%, 70% or 80% of the total injected dose of the nucleic acid-lipid particles is present in plasma about 8, 12, 24, 36, or 48 hours after injection. In one embodiment, the presence of an interfering RNA in cells of the lung, liver, tumor or at a site of inflammation is detectable at about 8, 12, 24, 36, 48, 60, 72 or 96 hours after administration. In one embodiment, downregulation of expression of the target sequence is detectable at about 8, 12, 24, 36, 48, 60, 72 or 96 hours after administration. In one embodiment, downregulation of expression of the target sequence occurs preferentially in tumor cells or in cells at a site of inflammation. In one embodiment, the presence of an interfering RNA in cells at a site distal to the site of administration is detectable at least four days after intravenous injection of the nucleic acid-lipid particle. In another embodiment, the presence of an interfering RNA in of cells in the lung, liver or a tumor is detectable at least four days after injection of the nucleic acid-lipid particle. In another embodiment, the nucleic acid-lipid particle is administered parenterally or intraperitoneally.

The particles are suitable for use in intravenous nucleic acid transfer as they are stable in circulation, of a size required for pharmacodynamic behavior resulting in access to extravascular sites and target cell populations. The invention also provides for pharmaceutically acceptable compositions comprising a nucleic acid-lipid particle.

Another embodiment of the present invention provides methods for in vivo delivery of interfering RNA. A nucleic acid-lipid particle comprising a cationic lipid, a non-cationic lipid, a conjugated lipid that inhibits aggregation of particles, and interfering RNA is administered (e.g., intravenously) to a subject (e.g., a mammal such as a human). In some embodiments, the invention provides methods for in vivo delivery of interfering RNA to the liver of a mammalian subject.

A further embodiment of the present invention provides a method of treating a disease or disorder in a mammalian subject. A therapeutically effective amount of a nucleic acid-lipid particle comprising a cationic lipid, a non-cationic lipid, a conjugated lipid that inhibits aggregation of particles, and interfering RNA is administered to the mammalian subject (e.g., a rodent such as a mouse, a primate such as a human or a monkey). In some embodiments, the disease or disorder is associated with expression and/or overexpression of a gene and expression or overexpression of the gene is reduced by the interfering RNA.

DEFINITIONS

The term "lipid" refers to a group of organic compounds that include, but are not limited to, esters of fatty acids and are characterized by being insoluble in water, but soluble in many organic solvents. They are usually divided into at least three classes: (1) "simple lipids" which include fats and oils as well as waxes; (2) "compound lipids" which include phospholipids and glycolipids; (3) "derived lipids" such as steroids.

"Lipid vesicle" refers to any lipid composition that can be used to deliver a compound including, but not limited to, liposomes, wherein an aqueous volume is encapsulated by an amphipathic lipid bilayer; or wherein the lipids coat an interior comprising a large molecular component, such as a plasmid comprising an interfering RNA sequence, with a reduced aqueous interior; or lipid aggregates or micelles, wherein the encapsulated component is contained within a relatively disordered lipid mixture.

As used herein, "lipid encapsulated" can refer to a lipid formulation that provides a compound with full encapsulation, partial encapsulation, or both. In a preferred embodiment, the nucleic acid is fully encapsulated in the lipid formulation (e.g., to form an SPLP, pSPLP, or other SNALP).

As used herein, the term "SNALP" refers to a stable nucleic acid lipid particle, including SPLP. A SNALP represents a vesicle of lipids coating a reduced aqueous interior comprising a nucleic acid (e.g., ssDNA, dsDNA, ssRNA, micro RNA (miRNA), short hairpin RNA (shRNA), dsRNA, siRNA, or a plasmid, including plasmids from which an interfering RNA is transcribed). As used herein, the term "SPLP" refers to a nucleic acid lipid particle comprising a nucleic acid (e.g., a plasmid) encapsulated within a lipid vesicle. SNALPs and SPLPs typically contain a cationic lipid, a non-cationic lipid, and a lipid that prevents aggregation of the particle (e.g., a PEG-lipid conjugate). SNALPs and SPLPs have systemic application as they exhibit extended circulation lifetimes following intravenous (i.v.) injection, accumulate at distal sites (e.g., sites physically separated from the administration site and can mediate expression of the transfected gene at these distal sites. SPLPs include "pSPLP" which comprise an encapsulated condensing agent-nucleic acid complex as set forth in WO 00/03683.

The term "vesicle-forming lipid" is intended to include any amphipathic lipid having a hydrophobic moiety and a polar head group, and which by itself can form spontaneously into bilayer vesicles in water, as exemplified by most phospholipids.

The term "vesicle-adopting lipid" is intended to include any amphipathic lipid that is stably incorporated into lipid bilayers in combination with other amphipathic lipids, with its hydrophobic moiety in contact with the interior, hydrophobic region of the bilayer membrane, and its polar head group moiety oriented toward the exterior, polar surface of the membrane. Vesicle-adopting lipids include lipids that on their own tend to adopt a nonlamellar phase, yet which are capable of assuming a bilayer structure in the presence of a bilayer-stabilizing component. A typical example is DOPE (dioleoylphosphatidylethanolamine). Bilayer stabilizing components include, but are not limited to, conjugated lipids that inhibit aggregation of the SNALPs, polyamide oligomers (e.g., ATTA-lipid derivatives), peptides, proteins, detergents, lipid-derivatives, PEG-lipid derivatives such as PEG coupled to dialkyloxypropyls, PEG coupled to diacylglycerols, PEG coupled to phosphatidyl-ethanolamines, and PEG conjugated to ceramides as described in U.S. Pat. No. 5,885,613.

The term "amphipathic lipid" refers, in part, to any suitable material wherein the hydrophobic portion of the lipid material orients into a hydrophobic phase, while the hydrophilic portion orients toward the aqueous phase. Amphipathic lipids are usually the major component of a lipid vesicle. Hydrophilic characteristics derive from the presence of polar or charged groups such as carbohydrates, phosphate, carboxylic, sulfato, amino, sulfhydryl, nitro, hydroxy and other like groups. Hydrophobicity can be conferred by the inclusion of apolar groups that include, but are not limited to, long chain saturated and unsaturated aliphatic hydrocarbon groups and such groups substituted by one or more aromatic, cycloaliphatic or heterocyclic group(s). Examples of amphipathic compounds include, but are not limited to, phospholipids, aminolipids and sphingolipids. Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine or dilinoleoylphosphatidylcholine. Other compounds lacking in phosphorus, such as sphingolipid, glycosphingolipid families, diacylglycerols and .beta.-acyloxyacids, are also within the group designated as amphipathic lipids. Additionally, the amphipathic lipid described above can be mixed with other lipids including triglycerides and sterols.

The term "neutral lipid" refers to any of a number of lipid species that exist either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides and diacylglycerols.

The term "noncationic lipid" refers to any neutral lipid as described above as well as anionic lipids. Non-cationic lipids include, e.g., distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoyl-phosphatidylcholine (POPC), palmitoyloleoyl-phosphatidylethanolamine (POPE) and dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, and 1-stearoyl-2-oleoyl-phosphatidylethanolamine (SOPE).

The term "anionic lipid" refers to any lipid that is negatively charged at physiological pH. These lipids include, but are not limited to, phosphatidylglycerol, cardiolipin, diacylphosphatidylserine, diacylphosphatidic acid, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), and other anionic modifying groups joined to neutral lipids.

The term "cationic lipid" refers to any of a number of lipid species that carry a net positive charge at a selected pH, such as physiological pH. Such lipids include, but are not limited to: 1,2-DiLinoleyloxy-N,N-dimethylaminopropane (DLinDMA) and 1,2-Dilinolenyloxy-N,N-dimethylaminopropane (DLenDMA), N,N-dioleyl-N,N-dimethylammonium chloride (DODAC); N-(2,3-dioleyloxy)propyl)-N,N,N-trimethylammonium chloride (DOTMA); N,N-distearyl-N,N-dimethylammonium bromide (DDAB); N-(2,3-dioleoyloxy)propyl)-N,N,N-trimethylammonium chloride (DOTAP); 3-(N—(N',N'-dimethylaminoethane)-carbamoyl) cholesterol (DC-Chol) and N-(1,2-dimyristyloxyprop-3-yl)-N,N-dimethyl-N-hydroxyethyl ammonium bromide (DMRIE). The following lipids are cationic and have a positive charge at below physiological pH: DODAP, DODMA, DMDMA and the like.

The term "hydrophobic lipid" refers to compounds having apolar groups that include, but are not limited to, long chain saturated and unsaturated aliphatic hydrocarbon groups and such groups optionally substituted by one or more aromatic, cycloaliphatic or heterocyclic group(s). Suitable examples include, but are not limited to, diacylglycerol, dialkylglycerol, N—N-dialkylamino, 1,2-diacyloxy-3-aminopropane and 1,2-dialkyl-3-aminopropane.

The term "fusogenic" refers to the ability of a liposome, an SNALP or other drug delivery system to fuse with membranes of a cell. The membranes can be either the plasma membrane or membranes surrounding organelles, e.g., endosome, nucleus, etc.

The term "diacylglycerol" refers to a compound having 2-fatty acyl chains, $R^1$ and $R^2$, both of which have independently between 2 and 30 carbons bonded to the 1- and 2-position of glycerol by ester linkages. The acyl groups can be saturated or have varying degrees of unsaturation. Diacylglycerols have the following general formula:

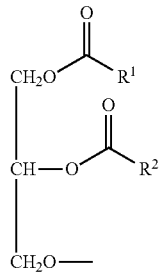

The term "dialkyloxypropyl" refers to a compound having 2-alkyl chains, $R^1$ and $R^2$, both of which have independently between 2 and 30 carbons. The alkyl groups can be saturated or have varying degrees of unsaturation. Dialkyloxypropyls have the following general formula:

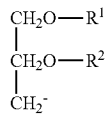

The term "ATTA" or "polyamide" refers to, but is not limited to, compounds disclosed in U.S. Pat. Nos. 6,320,017 and 6,586,559. These compounds include a compound having the formula

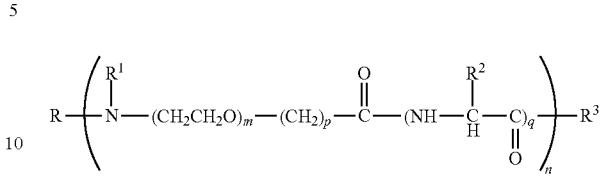

wherein: R is a member selected from the group consisting of hydrogen, alkyl and acyl; $R^1$ is a member selected from the group consisting of hydrogen and alkyl; or optionally, R and $R^1$ and the nitrogen to which they are bound form an azido moiety; $R^2$ is a member of the group selected from hydrogen, optionally substituted alkyl, optionally substituted aryl and a side chain of an amino acid; $R^3$ is a member selected from the group consisting of hydrogen, halogen, hydroxy, alkoxy, mercapto, hydrazino, amino and $NR^4R^5$, wherein $R^4$ and $R^5$ are independently hydrogen or alkyl; n is 4 to 80; m is 2 to 6; p is 1 to 4; and q is 0 or 1. It will be apparent to those of skill in the art that other polyamides can be used in the compounds of the present invention.

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. The term "basic amino acid" refers to naturally-occurring amino acids as well as synthetic amino acids and/or or amino acid mimetics having a net positive charge at a selected pH, such as physiological pH. This group includes, but is not limited to, lysine, arginine, asparagine, glutamine, histidine and the like. Naturally occurring amino acids are those encoded by the genetic code, as well as those amino acids that are later modified, e.g., hydroxyproline, α-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

The term "nucleic acid" or "polynucleotide" refers to a polymer containing at least two deoxyribonucleotides or ribonucleotides in either single- or double-stranded form. Unless specifically limited, the terms encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Cassol et al. (1992); Rossolini et al., *Mol. Cell. Probes* 8:91-98 (1994)). "Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides. DNA may be in the form of antisense, plasmid DNA, parts of a plasmid DNA, pre-condensed DNA, product of a polymerase chain reaction (PCR), vectors (P1, PAC, BAC, YAC, artificial chromosomes), expression cassettes, chimeric sequences, chromosomal DNA, or derivatives of these groups. The term nucleic acid is used interchangeably with gene, cDNA, mRNA encoded by a gene, and an interfering RNA molecule.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

The term "gene" refers to a nucleic acid (e.g., DNA or RNA) sequence that comprises partial length or entire length coding sequences necessary for the production of a polypeptide or precursor (e.g., hepatitis virus A, B, C, D, E, or G; or herpes simplex virus).

"Gene product," as used herein, refers to a product of a gene such as an RNA transcript.

The term "interfering RNA" or "RNAi" or "interfering RNA sequence" refers to double-stranded RNA that results in the degradation of specific mRNAs and can be used to interfere with translation from a desired mRNA target transcript. Short RNAi that is about 15-30 nucleotides in length is referred to as "small-interfering RNA" or "siRNA." Longer RNAi is generally referred to as "double-stranded RNA" or "dsRNA." A DNA molecule that transcribes dsRNA or siRNA (for instance, as a hairpin duplex) also provides RNAi. DNA molecules for transcribing dsRNA are disclosed in U.S. Pat. No. 6,573,099, and in U.S. Patent Publication Nos. 20020160393 and 20030027783. DNA molecules for transcribing siRNA are reviewed in Tuschl and Borkhardt, *Molecular Interventions,* 2:158 (2002).

By "silencing" or "downregulation" of a gene or nucleic acid is intended to mean a detectable decrease of transcription and/or translation of a target nucleic acid sequence, i.e., the sequence targeted by the RNAi, or a decrease in the amount or activity of the target sequence or protein in comparison to the normal level that is detected in the absence of the interfering RNA or other nucleic acid sequence. A detectable decrease can be as small as about 5% or 10%, or as great as about 80%, 90% or 100%. More typically, a detectable decrease is about 20%, 30%, 40%, 50%, 60%, or 70%.

As used herein, the term "aqueous solution" refers to a composition comprising in whole, or in part, water.

As used herein, the term "organic lipid solution" refers to a composition comprising in whole, or in part, an organic solvent having a lipid.

"Distal site," as used herein, refers to a physically separated site, which is not limited to an adjacent capillary bed, but includes sites broadly distributed throughout an organism.

"Serum-stable" in relation to nucleic acid-lipid particles means that the particle is not significantly degraded after exposure to a serum or nuclease assay that would significantly degrade free DNA. Suitable assays include, for example, a standard serum assay or a DNAse assay such as those described in the Examples below.

"Systemic delivery," as used herein, refers to delivery that leads to a broad biodistribution of a compound within an organism. Some techniques of administration can lead to the systemic delivery of certain compounds, but not others. Systemic delivery means that a useful, preferably therapeutic, amount of a compound is exposed to most parts of the body. To obtain broad biodistribution generally requires a blood lifetime such that the compound is not rapidly degraded or cleared (such as by first pass organs (liver, lung, etc.) or by rapid, nonspecific cell binding) before reaching a disease site distal to the site of administration. Systemic delivery of nucleic acid-lipid particules can be by any means known in the art including, for example, intravenous, subcutaneous, intraperitoneal, In a preferred embodiment, systemic delivery of nucleic acid-lipid particules is by intravenous delivery.

DETAILED DESCRIPTION

I. Introduction

Figure 1:
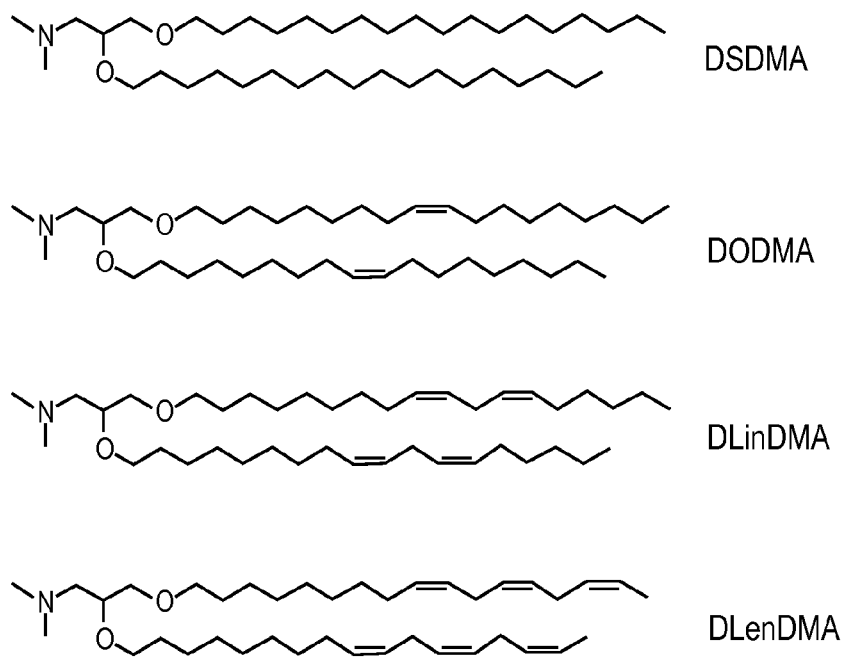
FIG. 1 illustrates the structures of two exemplary cationic lipids of the invention: 1,2-DiLinoleyloxy-N,N-dimethylaminopropane (DLinDMA) and 1,2-Dilinolenyloxy-N,N-dimethylaminopropane (DLenDMA).
Figure 2:
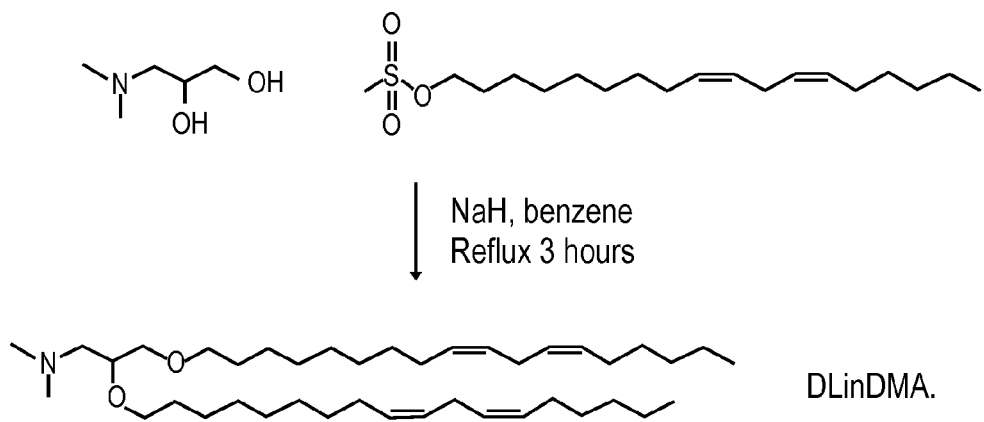
FIG. 2 illustrates the synthetic scheme for DLinDMA.
Figure 3:
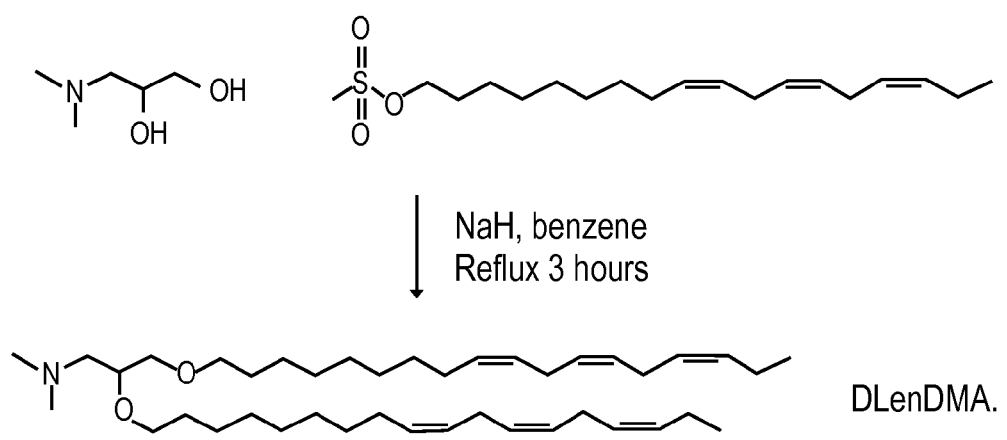
FIG. 3 illustrates the synthetic scheme for DLenDMA.

The present invention demonstrates the unexpected success of encapsulating short interfering RNA (siRNA) molecules in SNALPs comprising cationic lipids of Formula I, II, or mixture thereof. The SNALPs described herein can be used to deliver an siRNA to a cell to silence a target sequence of interest. SNALP comprising any of a broad range of concentrations of additional cationic lipids, non-cationic lipids, and other lipids can be used to practice the present invention. The SNALP can be prepared with any nucleic acid comprising an interfering RNA sequence, from any source and comprising any polynucleotide sequence, and can be prepared using any of a large number of methods.

II. Stable Nucleic Acid-Lipid Particles (SNALPs) and Properties Thereof

The stable nucleic acid-lipid particles or, alternatively, SNALPs typically comprise cationic lipid (i.e., a cationic lipid of Formula I or II) and nucleic acids. Such SNALPs also preferably comprise noncationic lipid and a bilayer stabilizing component (i.e., a conjugated lipid that inhibits aggregation of the SNALPs). The SNALPs of the present invention typically have a mean diameter of about 50 nm to about 150 nm, more typically about 100 nm to about 130 nm, most typically about 110 nm to about 115 nm, and are substantially nontoxic. In addition, the nucleic acids present in the SNALPs of the present invention are resistant in aqueous solution to degradation with a nuclease.

In one embodiment, the present invention provides stabilized nucleic acid-lipid particles (SPLPs or SNALPs) and other lipid-based carrier systems (e.g., a liposome, a micelle, a virosome, a lipid-nucleic acid particle, a nucleic acid complex and mixtures thereof) containing cationic lipids of the present invention, i.e., cationic lipids of Formula I, Formula II, or a combination thereof. The lipid-nucleic acid particles of the present invention typically comprise a nucleic acid, a cationic lipid of Formula I or Formula II, a non-cationic lipid and a PEG-lipid conjugate. The cationic lipid of Formula I or Formula II typically comprises from about 2% to about 60%, from about 5% to about 50%, from about 10% to about 45%, from about 20% to about 40%, or about 30% of the total lipid present in said particle. The non-cationic lipid typically comprises from about 5% to about 90%, from about 10% to about 85%, from about 20% to about 80%, from about 30% to about 70%, from about 40% to about 60% or about 48% of the total lipid present in said particle. The PEG-lipid conjugate typically comprises from about 1% to about 20%, from about 1.5% to about 18%, from about 4% to about 15%, from about 5% to about 12%, or about 2% of the total lipid present in said particle. The nucleic acid-lipid particles of the present invention may further comprise cholesterol. If present, the cholesterol typically comprises from about 10% to about 60%, from about 12% to about 58%, from about 20% to about 55%, or about 48% of the total lipid present in said particle. It will be readily apparent to one of skill in the art that the proportions of the components of the nucleic acid-lipid particles may be varied, e.g., using the ERP assay described herein. For example for systemic delivery, the cationic lipid may comprise from about 5% to about 15% of the total lipid present in said particle and for local or regional delivery, the cationic lipid comprises from about 40% to about 50% of the total lipid present in said particle.

A. Cationic Lipids

Cationic lipids of Formula I and II may be used in the present invention, either alone or in combination with one or more other cationic lipid species or non-cationic lipid species. Cationic lipids of Formula I and II have the following structures:

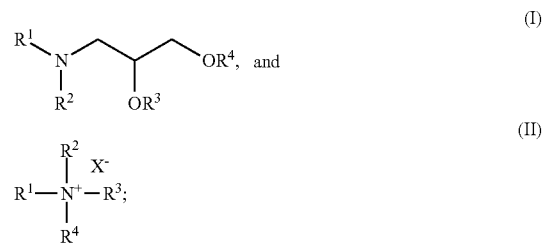

wherein $R^1$ and $R^2$ are independently selected and are H or $C_1$-$C_3$ alkyls. $R^3$ and $R^4$ are independently selected and are alkyl groups having from about 10 to about 20 carbon atoms; at least one of $R^3$ and $R^4$ comprises at least two sites of unsaturation. In one embodiment, $R^3$ and $R^4$ are both the same, i.e., $R^3$ and $R^4$ are both linoleyl (C18), etc. In another embodiment, $R^3$ and $R^4$ are different, i.e., $R^3$ is myristyl (C14) and $R^4$ is linoleyl (C18). In a preferred embodiment, the cationic lipids of the present invention are symmetrical, i.e., $R^3$ and $R^4$ are both the same. In another preferred embodiment, both $R^3$ and $R^4$ comprise at least two sites of unsaturation. In some embodiments, $R^3$ and $R^4$ are independently selected from dodecadienyl, tetradecadienyl, hexadecadienyl, linoleyl, and icosadienyl. In a preferred embodiment, $R^3$ and $R^4$ are both linoleyl. In some embodiments, $R^3$ and $R^4$ comprise at least three sites of unsaturation and are independently selected from, e.g., dodecatrienyl, tetradectrienyl, hexadecatrienyl, linolenyl, and icosatrienyl.

The cationic lipids of Formula I and Formula II described herein typically carry a net positive charge at a selected pH, such as physiological pH. It has been surprisingly found that cationic lipids comprising alkyl chains with multiple sites of unsaturation, e.g., at least two or three sites of unsaturation, are particularly useful for forming lipid-nucleic acid particles with increased membrane fluidity. A number of cationic lipids and related analogs, which are also useful in the present invention, have been described in co-pending U.S. Ser. No. 08/316,399; U.S. Pat. Nos. 5,208,036, 5,264,618, 5,279,833 and 5,283,185, and WO 96/10390.

Additional suitable cationic lipids include, e.g., dioctadecyldimethylammonium ("DODMA"), Di stearyldimethylammonium ("DSDMA"), N,N-dioleyl-N,N-dimethylammonium chloride ("DODAC"); N-(2,3-dioleyloxy)propyl)-N,N,N-trimethylammonium chloride ("DOTMA"); N,N-distearyl-N,N-dimethylammonium bromide ("DDAB"); N-(2,3-dioleoyloxy)propyl)-N,N,N-trimethylammonium chloride ("DOTAP"); 3-(N—(N',N'-dimethylaminoethane)-carbamoyl)cholesterol ("DC-Chol") and N-(1,2-dimyristyloxyprop-3-yl)-N,N-dimethyl-N-hydroxyethyl ammonium bromide ("DMRIE"). A number of these lipids and related analogs, which are also useful in the present invention, have been described in U.S. Pat. Nos. 5,208,036, 5,264,618, 5,279,833, 5,283,185, 5,753,613 and 5,785,992.

B. Non-Cationic Lipids

The noncationic lipids used in the present invention can be any of a variety of neutral uncharged, zwitterionic or anionic lipids capable of producing a stable complex. They are preferably neutral, although they can alternatively be positively or negatively charged. Examples of noncationic lipids useful in the present invention include: phospholipid-related materials, such as lecithin, phosphatidylethanolamine, lysolecithin, lysophosphatidylethanolamine, phosphatidylserine, phosphatidylinositol, sphingomyelin, cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE). Noncationic lipids or sterols such as cholesterol may be present. Additional nonphosphorous containing lipids are, e.g., stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkyl-aryl sulfate polyethyloxylated fatty acid amides, dioctadecyldimethyl ammonium bromide and the like, diacylphosphatidylcholine, diacylphosphatidylethanolamine, ceramide, sphingomyelin, cephalin, and cerebrosides. Other lipids such as lysophosphatidylcholine and lysophosphatidylethanolamine may be present. Noncationic lipids also include polyethylene glycol-based polymers such as PEG 2000, PEG 5000 and polyethylene glycol conjugated to phospholipids or to ceramides (referred to as PEG-Cer), as described in co-pending U.S. Ser. No. 08/316,429.

In preferred embodiments, the noncationic lipids are diacylphosphatidylcholine (e.g., distearoylphosphatidylcholine, dioleoylphosphatidylcholine, dipalmitoylphosphatidylcholine and dilinoleoylphosphatidylcholine), diacylphosphatidylethanolamine (e.g., dioleoylphosphatidylethanolamine and palmitoyloleoylphosphatidylethanolamine), ceramide or sphingomyelin. The acyl groups in these lipids are preferably acyl groups derived from fatty acids having $C_{10}$-$C_{24}$ carbon chains. More preferably the acyl groups are lauroyl, myristoyl, palmitoyl, stearoyl or oleoyl. In particularly preferred embodiments, the noncationic lipid will be cholesterol, 1,2-sn-dioleoylphosphatidylethanolamine, or egg sphingomyelin (ESM).

C. Bilayer Stabilizing Component

In addition to cationic and non-cationic lipids, the SPLPs of the present invention comprise bilayer stabilizing component (BSC) such as an ATTA-lipid or a PEG-lipid, such as PEG coupled to dialkyloxypropyls (PEG-DAA) as described in, e.g., WO 05/026372, PEG coupled to diacylglycerol (PEG-DAG) as described in, e.g., U.S. Patent Publication Nos. 20030077829 and 2005008689), PEG coupled to phosphatidylethanolamine (PE) (PEG-PE), or PEG conjugated to ceramides, or a mixture thereof (see, U.S. Pat. No. 5,885,613). In one preferred embodiment, the BSC is a conjugated lipid that inhibits aggregation of the SPLPs. Suitable conjugated lipids include, but are not limited to PEG-lipid conjugates, ATTA-lipid conjugates, cationic-polymer-lipid conjugates (CPLs) or mixtures thereof. In one preferred embodiment, the SPLPs comprise either a PEG-lipid conjugate or an ATTA-lipid conjugate together with a CPL.

PEG is a polyethylene glycol, a linear, water-soluble polymer of ethylene PEG repeating units with two terminal hydroxyl groups. PEGs are classified by their molecular weights; for example, PEG 2000 has an average molecular weight of about 2,000 daltons, and PEG 5000 has an average molecular weight of about 5,000 daltons. PEGs are commercially available from Sigma Chemical Co. and other companies and include, for example, the following: monomethoxypolyethylene glycol (MePEG-OH), monomethoxypolyethylene glycol-succinate (MePEG-S), monomethoxypolyethylene glycol-succinimidyl succinate (MePEG-S—NHS), monomethoxypolyethylene glycol-amine (MePEG-NH$_2$), monomethoxypolyethylene glycol-tresylate (MePEG-TRES), and monomethoxypolyethylene glycol-imidazolyl-carbonyl (MePEG-IM). In addition, monomethoxypolyethyleneglycol-acetic acid (MePEG-CH$_2$COOH), is particularly useful for preparing the PEG-lipid conjugates including, e.g., PEG-DAA conjugates.

In a preferred embodiment, the PEG has an average molecular weight of from about 550 daltons to about 10,000 daltons, more preferably of about 750 daltons to about 5,000 daltons, more preferably of about 1,000 daltons to about 5,000 daltons, more preferably of about 1,500 daltons to about 3,000 daltons and, even more preferably, of about 2,000 daltons, or about 750 daltons. The PEG can be optionally substituted by an alkyl, alkoxy, acyl or aryl group. PEG can be conjugated directly to the lipid or may be linked to the lipid via a linker moiety. Any linker moiety suitable for coupling the PEG to a lipid can be used including, e.g., non-ester containing linker moieties and ester-containing linker moieties. In a preferred embodiment, the linker moiety is a non-ester containing linker moiety. As used herein, the term "non-ester containing linker moiety" refers to a linker moiety that does not contain a carboxylic ester bond (—OC(O)—). Suitable non-ester containing linker moieties include, but are not limited to, amido (—C(O)NH—), amino (—NR—), carbonyl (—C(O)—), carbamate (—NHC(O)O—), urea (—NHC(O)NH—), disulphide (—S—S—), ether (—O—), succinyl (—(O)CCH$_2$CH$_2$C(O)—), succinamidyl (—NHC(O)CH$_2$CH$_2$C(O)NH—), ether, disulphide, etc. as well as combinations thereof (such as a linker containing both a carbamate linker moiety and an amido linker moiety). In a preferred embodiment, a carbamate linker is used to couple the PEG to the lipid.

In other embodiments, an ester containing linker moiety is used to couple the PEG to the lipid. Suitable ester containing linker moieties include, e.g., carbonate (—OC(O)O—), succinoyl, phosphate esters (—O—(O)POH—O—), sulfonate esters, and combinations thereof Phosphatidylethanolamines having a variety of acyl chain groups of varying chain lengths and degrees of saturation can be conjugated to polyethyleneglycol to form the bilayer stabilizing component. Such phosphatidylethanolamines are commercially available, or can be isolated or synthesized using conventional techniques known to those of skilled in the art. Phosphatidylethanolamines containing saturated or unsaturated fatty acids with carbon chain lengths in the range of $C_{10}$ to $C_{20}$ are preferred. Phosphatidylethanolamines with mono- or diunsaturated fatty acids and mixtures of saturated and unsaturated fatty acids can also be used. Suitable phosphatidylethanolamines include, but are not limited to, the following: dimyristoylphosphatidylethanolamine (DMPE), dipalmitoylphosphatidylethanolamine (DPPE), dioleoylphosphatidylethanolamine (DOPE) and distearoylphosphatidylethanolamine (DSPE).

The term "ATTA" or "polyamide" refers to, but is not limited to, compounds disclosed in U.S. Pat. Nos. 6,320,017 and 6,586,559. These compounds include a compound having the formula

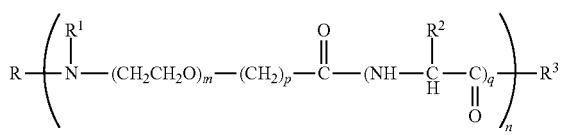

wherein: R is a member selected from the group consisting of hydrogen, alkyl and acyl; $R^1$ is a member selected from the group consisting of hydrogen and alkyl; or optionally, R and $R^1$ and the nitrogen to which they are bound form an azido moiety; $R^2$ is a member of the group selected from hydrogen, optionally substituted alkyl, optionally substituted aryl and a side chain of an amino acid; $R^3$ is a member selected from the group consisting of hydrogen, halogen, hydroxy, alkoxy, mercapto, hydrazino, amino and $NR^4R^5$, wherein $R^4$ and $R^5$ are independently hydrogen or alkyl; n is 4 to 80; m is 2 to 6; p is 1 to 4; and q is 0 or 1. It will be apparent to those of skill in the art that other polyamides can be used in the compounds of the present invention.

The term "diacylglycerol" refers to a compound having 2-fatty acyl chains, le and $R^2$, both of which have independently between 2 and 30 carbons bonded to the 1- and 2-position of glycerol by ester linkages. The acyl groups can be saturated or have varying degrees of unsaturation. Diacylglycerols have the following general formula:

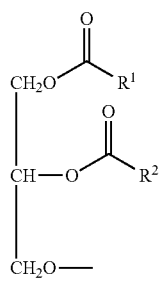

The term "dialkyloxypropyl" refers to a compound having 2-alkyl chains, $R^1$ and $R^2$, both of which have independently between 2 and 30 carbons. The alkyl groups can be saturated or have varying degrees of unsaturation. Dialkyloxypropyls have the following general formula:

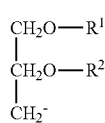

In one preferred embodiment, the PEG-lipid is a PEG-DAA conjugate has the following formula:

In Formula VI, $R^1$ and $R^2$ are independently selected and are long-chain alkyl groups having from about 10 to about 22 carbon atoms. The long-chain alkyl groups can be saturated or unsaturated. Suitable alkyl groups include, but are not limited to, lauryl (C12), myristyl (C14), palmityl (C16), stearyl (C18) and icosyl (C20). In preferred embodiments, $R^1$ and $R^2$ are the same, i.e., $R^1$ and $R^2$ are both myristyl (i.e., dimyristyl), $R^1$ and $R^2$ are both stearyl (i.e., distearyl), etc.

In Formula VI above, "$R^1$ and $R^2$" are independently selected and are alkyl groups having from about 10 to about 20 carbon atoms; PEG is a polyethyleneglycol; and L is a non-ester-containing linker moiety as described above. Suitable alkyl groups include, but are not limited to, lauryl (C12), myristyl (C14), palmityl (C16), stearyl (C18) and icosyl (C20). In a preferred embodiment; $R^1$ and $R^2$ are the same, i.e., they are both myristyl (C14) or both palmityl (C16) or both stearyl (C18). In a preferred embodiment, the alkyl groups are saturated.

In Formula VI above, "PEG" is a polyethylene glycol having an average molecular weight ranging of about 550 daltons to about 10,000 daltons, more preferably of about 750 daltons to about 5,000 daltons, more preferably of about 1,000 daltons to about 5,000 daltons, more preferably of about 1,500 daltons to about 3,000 daltons and, even more preferably, of about 2,000 daltons, or about 750 daltons. The PEG can be optionally substituted with alkyl, alkoxy, acyl or aryl. In a preferred embodiment, the terminal hydroxyl group is substituted with a methoxy or methyl group.

In Formula VI, above, "L" is a non-ester containing linker moiety or an ester containing linker moiety. In a preferred embodiment, L is a non-ester containing linker moiety. Suitable non-ester containing linkers include, but are not limited to, an amido linker moiety, an amino linker moiety, a carbonyl linker moiety, a carbamate linker moiety, a urea linker moiety, an ether linker moiety, a disulphide linker moiety, a succinamidyl linker moiety and combinations thereof. In a preferred embodiment, the non-ester containing linker moiety is a carbamate linker moiety (i.e., a PEG-C-DAA conjugate). In another preferred embodiment, the non-ester containing linker moiety is an amido linker moiety (i.e., a PEG-A-DAA conjugate). In a preferred embodiment, the non-ester containing linker moiety is a succinamidyl linker moiety (i.e., a PEG-S-DAA conjugate).

The PEG-DAA conjugates are synthesized using standard techniques and reagents known to those of skill in the art. It will be recognized that the PEG-DAA conjugates will contain various amide, amine, ether, thio, carbamate and urea linkages. T hose of skill in the art will recognize that methods and reagents for forming these bonds are well known and readily available. See, e.g., March, ADVANCED ORGANIC CHEMISTRY (Wiley 1992), Larock, COMPREHENSIVE ORGANIC TRANSFORMATIONS (VCH 1989); and Furniss, VOGEL'S TEXTBOOK OF PRACTICAL ORGANIC CHEMISTRY 5th ed. (Longman 1989). It will also be appreciated that any functional groups present may require protection and deprotection at different points in the synthesis of the PEG-DAA conjugates. Those of skill in the art will recognize that such techniques are well known.

See, e.g., Green and Wuts, PROTECTIVE GROUPS IN ORGANIC SYNTHESIS (Wiley 1991).

In a presently preferred embodiment, the PEG-DAA conjugate is a dilauryloxypropyl (C12)-PEG conjugate, dimyristyloxypropyl (C14)-PEG conjugate, a dipalmitoyloxypropyl (C16)-PEG conjugate or a disteryloxypropyl (C18)-PEG conjugate. Those of skill in the art will readily appreciate that other dialkyloxypropyls can be used in the PEG-DAA conjugates of the present invention.

In addition to the foregoing, it will be readily apparent to those of skill in the art that other hydrophilic polymers can be used in place of PEG. Examples of suitable polymers that can be used in place of PEG include, but are not limited to, polyvinylpyrrolidone, polymethyloxazoline, polyethyloxazoline, polyhydroxypropyl methacrylamide, polymethacrylamide and polydimethylacrylamide, polylactic acid, polyglycolic acid, and derivatized celluloses, such as hydroxymethylcellulose or hydroxyethylcellulose.

In addition to the foregoing components, the SNALPs and SPLPs of the present invention can further comprise cationic poly(ethylene glycol) (PEG) lipids, or CPLs, that have been designed for insertion into lipid bilayers to impart a positive charge (see, Chen, et al., Bioconj. Chem. 11:433-437 (2000)). Suitable SPLPs and SPLP-CPLs for use in the present invention, and methods of making and using SPLPs and SPLP-CPLs, are disclosed, e.g., in U.S. Pat. No. 6,852,334 and WO 00/62813. Cationic polymer lipids (CPLs) useful in the present invention have the following architectural features: (1) a lipid anchor, such as a hydrophobic lipid, for incorporating the CPLs into the lipid bilayer; (2) a hydrophilic spacer, such as a polyethylene glycol, for linking the lipid anchor to a cationic head group; and (3) a polycationic moiety, such as a naturally occurring amino acid, to produce a protonizable cationic head group.

Suitable CPL include compounds of Formula VII:

A-W—Y (VII)

wherein A, W and Y are as described below.

With reference to Formula VII, "A" is a lipid moiety such as an amphipathic lipid, a neutral lipid or a hydrophobic lipid that acts as a lipid anchor. Suitable lipid examples include vesicle-forming lipids or vesicle adopting lipids and include, but are not limited to, diacylglycerolyls, dialkylglycerolyls, N—N-dialkylaminos, 1,2-diacyloxy-3-aminopropanes and 1,2-dialkyl-3-aminopropanes.

"W" is a polymer or an oligomer, such as a hydrophilic polymer or oligomer. Preferably, the hydrophilic polymer is a biocompatable polymer that is nonimmunogenic or possesses low inherent immunogenicity. Alternatively, the hydrophilic polymer can be weakly antigenic if used with appropriate adjuvants. Suitable nonimmunogenic polymers include, but are not limited to, PEG, polyamides, polylactic acid, polyglycolic acid, polylactic acid/polyglycolic acid copolymers and combinations thereof. In a preferred embodiment, the polymer has a molecular weight of about 250 to about 7000 daltons.

"Y" is a polycationic moiety. The term polycationic moiety refers to a compound, derivative, or functional group having a positive charge, preferably at least 2 positive charges at a selected pH, preferably physiological pH. Suitable polycationic moieties include basic amino acids and their derivatives such as arginine, asparagine, glutamine, lysine and histidine; spermine; spermidine; cationic dendrimers; polyamines; polyamine sugars; and amino polysaccharides. The polycationic moieties can be linear, such as linear tetralysine, branched or dendrimeric in structure. Polycationic moieties have between about 2 to about 15 positive charges, preferably between about 2 to about 12 positive charges, and more preferably between about 2 to about 8 positive charges at selected pH values. The selection of which polycationic moiety to employ may be determined by the type of liposome application which is desired.

The charges on the polycationic moieties can be either distributed around the entire liposome moiety, or alternatively, they can be a discrete concentration of charge density in one particular area of the liposome moiety e.g., a charge spike. If the charge density is distributed on the liposome, the charge density can be equally distributed or unequally distributed. All variations of charge distribution of the polycationic moiety are encompassed by the present invention.

The lipid "A," and the nonimmunogenic polymer "W," can be attached by various methods and preferably, by covalent attachment. Methods known to those of skill in the art can be used for the covalent attachment of "A" and "W." Suitable linkages include, but are not limited to, amide, amine, carboxyl, carbonate, carbamate, ester and hydrazone linkages. It will be apparent to those skilled in the art that "A" and "W" must have complementary functional groups to effectuate the linkage. The reaction of these two groups, one on the lipid and the other on the polymer, will provide the desired linkage. For example, when the lipid is a diacylglycerol and the terminal hydroxyl is activated, for instance with NHS and DCC, to form an active ester, and is then reacted with a polymer which contains an amino group, such as with a polyamide (see, U.S. Pat. Nos. 6,320,017 and 6,586,559), an amide bond will form between the two groups.

In certain instances, the polycationic moiety can have a ligand attached, such as a targeting ligand or a chelating moiety for complexing calcium. Preferably, after the ligand is attached, the cationic moiety maintains a positive charge. In certain instances, the ligand that is attached has a positive charge. Suitable ligands include, but are not limited to, a compound or device with a reactive functional group and include lipids, amphipathic lipids, carrier compounds, bioaffinity compounds, biomaterials, biopolymers, biomedical devices, analytically detectable compounds, therapeutically active compounds, enzymes, peptides, proteins, antibodies, immune stimulators, radiolabels, fluorogens, biotin, drugs, haptens, DNA, RNA, polysaccharides, liposomes, virosomes, micelles, immunoglobulins, functional groups, other targeting moieties, or toxins.

D. Nucleic Acid Component

The nucleic acid component of the present invention comprises an interfering RNA that silences (e.g., partially or completely inhibits) expression of a gene of interest. An interfering RNA can be provided in several forms. For example an interfering RNA can be provided as one or more isolated small-interfering RNA (siRNA) duplexes, longer double-stranded RNA (dsRNA) or as siRNA or dsRNA transcribed from a transcriptional cassette in a DNA plasmid. The interfering RNA can be administered alone or in combination with the administration of conventional agents used to treat the disease or disorder associated with the gene of interest. Genes of interest include, but are not limited to, genes associated with viral infection and survival, genes associated with liver and kidney diseases and disorders, genes associated with tumorigenesis and cell transformation, angiogenic genes, immunomodulator genes, such as those associated with inflammatory and autoimmune responses, ligand receptor genes, and genes associated with neurodegenerative disorders.

1. Selecting siRNA Sequences

Suitable siRNA sequences can be identified using any means known in the art. Typically, the methods described in Elbashir, et al., *Nature* 411:494-498 (2001) and Elbashir, et al., *EMBO J* 20: 6877-6888 (2001) are combined with rational design rules set forth in Reynolds et al., *Nature Biotech.* 22(3):326-330 (2004).

Typically, the sequence within about 50 to about 100 nucleotides 3' of the AUG start codon of a transcript from the target gene of interest is scanned for dinucleotide sequences (e.g., AA, CC, GG, or UU) (see, e.g., Elbashir, et al., *EMBO J* 20: 6877-6888 (2001)). The nucleotides immediately 3' to the dinucleotide sequences are identified as potential siRNA target sequences. Typically, the 19, 21, 23, 25, 27, 29, 31, 33, 35 or more nucleotides immediately 3' to the dinucleotide sequences are identified as potential siRNA target sites. In some embodiments, the dinucleotide sequence is an AA sequence and the 19 nucleotides immediately 3' to the AA dinucleotide are identified as a potential siRNA target site. Typically siRNA target sites are spaced at different positions along the length of the target gene. To further enhance silencing efficiency of the siRNA sequences, potential siRNA target sites may be further analyzed to identify sites that do not contain regions of homology to other coding sequences. For example, a suitable siRNA target site of about 21 base pairs typically will not have more than 16-17 contiguous base pairs of homology to other coding sequences. If the siRNA sequences are to be expressed from an RNA Pol III promoter, siRNA target sequences lacking more than 4 contiguous A's or T's are selected.

Once the potential siRNA target site has been identified siRNA sequences complementary to the siRNA target sites may be designed. To enhance their silencing efficiency, the siRNA sequences may also be analyzed by a rational design algorithm to identify sequences that have one or more of the following features: (1) G/C content of about 25% to about 60% G/C; (2) at least 3 A/Us at positions 15-19 of the sense strand; (3) no internal repeats; (4) an A at position 19 of the sense strand; (5) an A at position 3 of the sense strand; (6) a U at position 10 of the sense strand; (7) no G/C at position 19 of the sense strand; and (8) no G at position 13 of the sense strand. siRNA design tools that incorporate algorithms that assign suitable values of each of these features and are useful for selection of siRNA can be found at, e.g., http://boz094.ust.hk/RNAi/siRNA.

In some embodiments, once a potential siRNA sequence has been identified, the sequence is analyzed for the presence or absence of immunostimulatory motifs (e.g., GU-rich motifs) as described in, e.g., co-pending U.S. Provisional Patent Application No. 60/585,301, filed Jul. 2, 2004; 60/589,363, filed Jul. 19, 2004; 60/627,326, filed Nov. 12, 2004; and 60/665,297, filed Mar. 25, 2005. Once identified, the immunostimulatory siRNA molecules can be modified to increase or decrease their immunostimulatory properties and the non-immunostimulatory molecules can be modified so that they possess immunostimulatory properties

2. Generating siRNA siRNA can be provided in several forms including, e.g., as one or more isolated small-interfering RNA (siRNA) duplexes, longer double-stranded RNA (dsRNA) or as siRNA or dsRNA transcribed from a transcriptional cassette in a DNA plasmid. siRNA may also be chemically synthesized. Preferably, the synthesized or transcribed siRNA have 3' overhangs of about 1-4 nucleotides, preferably of about 2-3 nucleotides and 5' phosphate termini. The siRNA sequences may have overhangs (e.g., 3' or 5' overhangs as described in (Elbashir, et al., *Genes Dev.* 15:188 (2001); Nykänen, et al., *Cell* 107:309 (2001)) or may lack overhangs (i.e., to have blunt ends).

An RNA population can be used to provide long precursor RNAs, or long precursor RNAs that have substantial or complete identity to a selected target sequence can be used to make the siRNA. The RNAs can be isolated from cells or tissue, synthesized, and/or cloned according to methods well known to those of skill in the art. The RNA can be a mixed population (obtained from cells or tissue, transcribed from cDNA, subtracted, selected, etc.), or can represent a single target sequence. RNA can be naturally occurring (e.g., isolated from tissue or cell samples), synthesized in vitro (e.g., using T7 or SP6 polymerase and PCR products or a cloned cDNA); or chemically synthesized.

To form a long dsRNA, for synthetic RNAs, the complement is also transcribed in vitro and hybridized to form a dsRNA. If a naturally occurring RNA population is used, the RNA complements are also provided (e.g., to form dsRNA for digestion by *E. coli* RNAse III or Dicer), e.g., by transcribing cDNAs corresponding to the RNA population, or by using RNA polymerases. The precursor RNAs are then hybridized to form double stranded RNAs for digestion. The dsRNAs can be directly administered to a subject or can be digested in vitro prior to administration.

Alternatively, one or more DNA plasmids encoding one or more siRNA templates are used to provide siRNA. siRNA can be transcribed as sequences that automatically fold into duplexes with hairpin loops from DNA templates in plasmids having RNA polymerase III transcriptional units, for example, based on the naturally occurring transcription units for small nuclear RNA U6 or human RNase P RNA H1 (see, Brummelkamp, et al., *Science* 296:550 (2002); Donzé, et al., *Nucleic Acids Res.* 30:e46 (2002); Paddison, et al., *Genes Dev.* 16:948 (2002); Yu, et al., *Proc. Natl. Acad. Sci.* 99:6047 (2002); Lee, et al., *Nat. Biotech.* 20:500 (2002); Miyagishi, et al., *Nat. Biotech.* 20:497 (2002); Paul, et al., *Nat. Biotech.* 20:505 (2002); and Sui, et al., *Proc. Natl. Acad. Sci.* 99:5515 (2002)). Typically, a transcriptional unit or cassette will contain an RNA transcript promoter sequence, such as an H1-RNA or a U6 promoter, operably linked to a template for transcription of a desired siRNA sequence and a termination sequence, comprised of 2-3 uridine residues and a polythymidine (T5) sequence (polyadenylation signal) (Brummelkamp, Science, supra). The selected promoter can provide for constitutive or inducible transcription. Compositions and methods for DNA-directed transcription of RNA interference molecules is described in detail in U.S. Pat. No. 6,573,099. The transcriptional unit is incorporated into a plasmid or DNA vector from which the interfering RNA is transcribed. Plasmids suitable for in vivo delivery of genetic material for therapeutic purposes are described in detail in U.S. Pat. Nos. 5,962,428 and 5,910,488. The selected plasmid can provide for transient or stable delivery of a target cell. It will be apparent to those of skill in the art that plasmids originally designed to express desired gene sequences can be modified to contain a transcriptional unit cassette for transcription of siRNA.

Methods for isolating RNA, synthesizing RNA, hybridizing nucleic acids, making and screening cDNA libraries, and performing PCR are well known in the art (see, e.g., Gubler & Hoffman, *Gene* 25:263-269 (1983); Sambrook et al., supra; Ausubel et al., supra), as are PCR methods (see U.S. Pat. Nos. 4,683,195 and 4,683,202; PCR Protocols: A Guide to Methods and Applications (Innis et al., eds, 1990)). Expression libraries are also well known to those of skill in the art. Additional basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

A suitable plasmid is engineered to contain, in expressible form, a template sequence that encodes a partial length sequence or an entire length sequence of a gene product of interest. Template sequences can also be used for providing isolated or synthesized siRNA and dsRNA. Generally, it is desired to downregulate or silence the transcription and translation of a gene product of interest.

3. Genes of Interest

Genes of interest include, but are not limited to, genes associated with viral infection and survival, genes associated with metabolic diseases and disorders (e.g., liver diseases and disorders), genes associated with tumorigenesis and cell transformation, angiogenic genes, immunomodulator genes, such as those associated with inflammatory and autoimmune responses, ligand receptor genes, and genes associated with neurodegenerative disorders.

a) Genes Associated with Viral Infection and Survival

Genes associated with viral infection and survival include those expressed by a virus in order to bind, enter and replicate in a cell. Of particular interest are viral sequences associated with chronic viral diseases. Viral sequences of particular interest include sequences of Hepatitis viruses (Hamasaki, et al., *FEBS Lett.* 543:51 (2003); Yokota, et al., *EMBO Rep.* 4:602 (2003); Schlomai, et al., *Hepatology* 37:764 (2003); Wilson, et al., *Proc. Natl. Acad. Sci.* 100: 2783 (2003); Kapadia, et al., *Proc. Natl. Acad. Sci.* 100:2014 (2003); and FIELDS VIROLOGY (Knipe et al. eds. 2001)), Human Immunodeficiency Virus (HIV) (Banerjea, et al., *Mol. Ther.* 8:62 (2003); Song, et al., *J. Virol.* 77:7174 (2003); Stephenson *JAMA* 289:1494 (2003); Qin, et al., *Proc. Natl. Acad. Sci.* 100:183 (2003)), Herpes viruses (Jia, et al., *J. Virol.* 77:3301 (2003)), and Human Papilloma Viruses (HPV) (Hall, et al., *J. Virol.* 77:6066 (2003); Jiang, et al., *Oncogene* 21:6041 (2002)). Exemplary hepatitis viral nucleic acid sequences that can be silenced include, but are not limited to: nucleic acid sequences involved in transcription and translation (e.g., En1, En2, X, P), nucleic acid sequences encoding structural proteins (e.g., core proteins including C and C-related proteins; capsid and envelope proteins including S, M, and/or L proteins, or fragments thereof) (see, e.g., FIELDS VIROLOGY, 2001, supra). Exemplary Hepatits C nucleic acid sequences that can be silenced include, but are not limited to: serine proteases (e.g., NS3/NS4), helicases (e.g. NS3), polymerases (e.g., NS5B), and envelope proteins (e.g., E1, E2, and p7). Hepatitis A nucleic acid sequences are set forth in e.g., Genbank Accession No. NC_001489; Hepatitis B nucleic acid sequences are set forth in, e.g., Genbank Accession No. NC_003977; Hepatitis C nucleic acid sequences are set forth in, e.g., Genbank Accession No. NC_004102; Hepatitis D nucleic acid sequence are set forth in, e.g., Genbank Accession No. NC_001653; Hepatitis E nucleic acid sequences are set forth in e.g., Genbank Accession No. NC_001434; and Hepatitis G nucleic acid sequences are set forth in e.g., Genbank Accession No. NC_001710.

b) Genes Associated with Metabolic Diseases and Disorders

Genes associated with metabolic diseases and disorders (e.g., disorders in which the liver is the target and liver diseases and disorders) include, for example genes expressed in, for example, dyslipidemia (e.g., liver X receptors (e.g., LXRα and LXRβ Genback Accession No. NM_007121), farnesoid X receptors (FXR) (Genbank Accession No. NM_005123), sterol-regulatory element binding protein (SREBP), Site-1 protease (S1P), 3-hydroxy-3-methylglutaryl coenzyme-A reductase (HMG coenzyme-A reductase), Apolipoprotein (ApoB), and Apolipoprotein (ApoE)) and diabetes (e.g., Glucose 6-phosphatase) (see, e.g., Forman et al., *Cell* 81:687 (1995); Seol et al., *Mol. Endocrinol.* 9:72 (1995), Zavacki et al., *PNAS USA* 94:7909 (1997); Sakai, et al., *Cell* 85:1037-1046 (1996); Duncan, et al., *J. Biol. Chem.* 272:12778-12785 (1997); Willy, et al., *Genes Dev.* 9(9):1033-45 (1995); Lehmann, et al., *J. Biol. Chem.* 272(6):3137-3140 (1997); Janowski, et al., *Nature* 383:728-731 (1996); Peet, et al., *Cell* 93:693-704 (1998)). One of skill in the art will appreciate that genes associated with metabolic diseases and disorders (e.g., diseases and disorders in which the liver is a target and liver diseases and disorders) include genes that are expressed in the liver itself as well as and genes expressed in other organs and tissues.

c) Genes Associated with Tumorigenesis

Examples of gene sequences associated with tumorigenesis and cell transformation include translocation sequences such as MLL fusion genes, BCR-ABL (Wilda, et al., *Oncogene,* 21:5716 (2002); Scherr, et al., *Blood* 101:1566), TEL-AML1, EWS-FLI1, TLS-FUS, PAX3-FKHR, BCL-2, AML1-ETO and AML1-MTG8 (Heidenreich, et al., *Blood* 101:3157 (2003)); overexpressed sequences such as multidrug resistance genes (Nieth, et al., *FEBS Lett.* 545:144 (2003); Wu, et al, *Cancer Res.* 63:1515 (2003)), cyclins (Li, et al., *Cancer Res.* 63:3593 (2003); Zou, et al., *Genes Dev.* 16:2923 (2002)), beta-Catenin (Verma, et al., *Clin Cancer Res.* 9:1291 (2003)), telomerase genes (Kosciolek, et al., *Mol Cancer Ther.* 2:209 (2003)), c-MYC, N-MYC, BCL-2, ERBB1 and ERBB2 (Nagy, et al. *Exp. Cell Res.* 285:39 (2003)); and mutated sequences such as RAS (reviewed in Tuschl and Borkhardt, *Mol. Interventions,* 2:158 (2002)). For example, silencing of sequences that encode DNA repair enzymes find use in combination with the administration of chemotherapeutic agents (Collis, et al., *Cancer Res.* 63:1550 (2003)). Genes encoding proteins associated with tumor migration are also target sequences of interest, for example, integrins, selectins and metalloproteinases. The foregoing examples are not exclusive. Any whole or partial gene sequence that facilitates or promotes tumorigenesis or cell transformation, tumor growth or tumor migration can be included as a gene sequence of interest.

d) Angiogenic/Anti-Angiogenic Genes

Angiogenic genes are able to promote the formation of new vessels. Of particular interest is Vascular Endothelial Growth Factor (VEGF) (Reich, et al., *Mol. Vis.* 9:210 (2003)) or VEGFr. siRNA sequences that target VEGFr are set forth in, e.g., GB 2396864; U.S. Patent Publication No. 20040142895; and CA2456444.

Anti-angiogenic genes are able to inhibit neovascularization. These genes are particularly useful for treating those cancers in which angiogenesis plays a role in the pathological development of the disease. Examples of anti-angiogenic genes include, but are not limited to, endostatin (see e.g., U.S. Pat. No. 6,174,861), angiostatin (see, e.g., U.S. Pat. No. 5,639,725), and VEGF-R2 (see e.g., Decaussin et al. (1999) *J. Pathol.* 188(4): 369-737).

e) Immonomodulator Genes

Immunomodulator genes are genes that modulate one or more immune responses. Examples of immunomodulator genes include cytokines such as growth factors (e.g., TGF-α, TGF-□β, EGF, FGF, IGF, NGF, PDGF, CGF, GM-CSF, SCF, etc.), interleukins (e.g., IL-2, IL-3, IL-4, IL-6, IL-7, IL-10, IL-12, IL-15, IL-20, etc.), interferons (e.g., IFN-α, IFN-β, IFN-γ, etc.), TNF (e.g., TNF-α), and Flt3-Ligand. Fas and Fas Ligand genes are also immunomodulator target sequences of interest (Song, et al., *Nat. Med.* 9:347 (2003)). Genes encoding secondary signaling molecules in hematopoietic and lymphoid cells are also included in the present invention, for example, Tec family kinases, such as Bruton's tyrosine kinase (Btk) (Heinonen, et al., *FEBS Lett.* 527:274 (2002)).

f) Cell Receptor Ligands

Cell receptor ligands include ligands that are able to bind to cell surface receptors (e.g., insulin receptor, EPO receptor, G-protein coupled receptors, receptors with tyrosine kinase activity, cytokine receptors, growth factor receptors, etc.), to modulate (e.g., inhibit, activate, etc.) the physiological pathway that the receptor is involved in (e.g., glucose level modulation, blood cell development, mitogenesis, etc.). Examples of cell receptor ligands include cytokines, growth factors, interleukins, interferons, erythropoietin (EPO), insulin, glucagon, G-protein coupled receptor ligands, etc.). Templates coding for an expansion of trinucleotide repeats (e.g., CAG repeats), find use in silencing pathogenic sequences in neurodegenerative disorders caused by the expansion of trinucleotide repeats, such as spinobulbular muscular atrophy and Huntington's Disease (Caplen, et al., *Hum. Mol. Genet.* 11:175 (2002)).

g) Tumor Suppressor Genes

Tumor suppressor genes are genes that are able to inhibit the growth of a cell, particularly tumor cells. Thus, delivery of these genes to tumor cells is useful in the treatment of cancers. Tumor suppressor genes include, but are not limited to, p53 (Lamb et al., *Mol. Cell. Biol.* 6:1379-1385 (1986), Ewen et al., *Science* 255:85-87 (1992), Ewen et al. (1991) *Cell* 66:1155-1164, and Hu et al., *EMBO J.* 9:1147-1155 (1990)), RB1 (Toguchida et al. (1993) *Genomics* 17:535-543), WT1 (Hastie, N. D., *Curr. Opin. Genet. Dev.* 3:408-413 (1993)), NF1 (Trofatter et al., *Cell* 72:791-800 (1993), Cawthon et al., *Cell* 62:193-201 (1990)), VHL (Latif et al., *Science* 260:1317-1320 (1993)), APC (Gorden et al., *Cell* 66:589-600 (1991)), DAP kinase (see e.g., Diess et al. (1995) *Genes Dev.* 9: 15-30), p16 (see e.g., Marx (1994) *Science* 264(5167): 1846), ARF (see e.g., Quelle et al. (1995) *Cell* 83(6): 993-1000), Neurofibromin (see e.g., Huynh et al. (1992) *Neurosci. Lett.* 143(1-2): 233-236), and PTEN (see e.g., Li et al. (1997) *Science* 275(5308): 1943-1947).

III. Preparation of SNALPS

The present invention provides a method of preparing serum-stable nucleic acid-lipid particles in which the plasmid or other nucleic acid is encapsulated in a lipid bilayer and is protected from degradation. The particles made by the methods of this invention typically have a size of about 50 nm to about 150 nm, more typically about 100 nm to about 130 nm, most typically about 110 nm to about 115 nm. The particles can be formed by any method known in the art including, but not limited to: a continuous mixing method, a detergent dialysis method, or a modification of a reverse-phase method which utilizes organic solvents to provide a single phase during mixing of the components.

In preferred embodiments, the cationic lipids are lipids of Formula I and II or combinations thereof. In other preferred embodiments, the noncationic lipids are ESM, DOPE, DOPC, DPPE, DMPE, 16:0 Monomethyl Phosphatidylethanolamine, 16:0 Dimethyl Phosphatidylethanolamine, 18:1 Trans Phosphatidylethanolamine, 18:0 18:1 Phosphatidylethanolamine (SOPE), 16:0 18:1 Phosphatidylethanolamine, DSPE, polyethylene glycol-based polymers (e.g., PEG 2000, PEG 5000, PEG-modified diacylglycerols, or PEG-modified dialkyloxypropyls), distearoylphosphatidylcholine (DSPC), cholesterol, or combinations thereof. In still other preferred embodiments, the organic solvents are methanol, chloroform, methylene chloride, ethanol, diethyl ether or combinations thereof.

In a particularly preferred embodiment, the nucleic acid is a plasmid; the cationic lipid is a lipid of Formula I or II or combinations thereof; the noncationic lipid is ESM, DOPE, PEG-DAAs, distearoylphosphatidylcholine (DSPC), cholesterol, or combinations thereof (e.g. DSPC and PEG-DAAs); and the organic solvent is methanol, chloroform, methylene chloride, ethanol, diethyl ether or combinations thereof In a particularly preferred embodiment, the present invention provides for nucleic acid-lipid particles produced via a continuous mixing method, e.g., process that includes providing an aqueous solution comprising a nucleic acid such as an siRNA or a plasmid, in a first reservoir, and providing an organic lipid solution in a second reservoir, and mixing the aqueous solution with the organic lipid solution such that the organic lipid solution mixes with the aqueous solution so as to substantially instantaneously produce a liposome encapsulating the nucleic acid (e.g., siRNA). This process and the apparatus for carrying this process is described in detail in U.S. Patent Publication No. 20040142025.

The action of continuously introducing lipid and buffer solutions into a mixing environment, such as in a mixing chamber, causes a continuous dilution of the lipid solution with the buffer solution, thereby producing a liposome substantially instantaneously upon mixing. As used herein, the phrase "continuously diluting a lipid solution with a buffer solution" (and variations) generally means that the lipid solution is diluted sufficiently rapidly in a hydration process with sufficient force to effectuate vesicle generation. By mixing the aqueous solution comprising a nucleic acid with the organic lipid solution, the organic lipid solution undergoes a continuous stepwise dilution in the presence of the buffer solution (i.e., aqueous solution) to produce a nucleic acid-lipid particle.

The serum-stable nucleic acid-lipid particles formed using the continuous mixing method typically have a size of from about 50 nm to about 150 nm, more typically about 100 nm to about 130 nm, most typically about 110 nm to about 115 nm. The particles thus formed do not aggregate and are optionally sized to achieve a uniform particle size.

In some embodiments, the particles are formed using detergent dialysis. Without intending to be bound by any particular mechanism of formation, a plasmid or other nucleic acid (e.g., siRNA) is contacted with a detergent solution of cationic lipids to form a coated nucleic acid complex. These coated nucleic acids can aggregate and precipitate. However, the presence of a detergent reduces this aggregation and allows the coated nucleic acids to react with excess lipids (typically, non-cationic lipids) to form particles in which the plasmid or other nucleic acid is encapsulated in a lipid bilayer. Thus, the present invention provides a method for the preparation of serum-stable nucleic acid-lipid particles, comprising:

(a) combining a nucleic acid with cationic lipids in a detergent solution to form a coated nucleic acid-lipid complex;

(b) contacting non-cationic lipids with the coated nucleic acid-lipid complex to form a detergent solution comprising a nucleic acid-lipid complex and non-cationic lipids; and (c) dialyzing the detergent solution of step (b) to provide a solution of serum-stable nucleic acid-lipid particles, wherein the nucleic acid is encapsulated in a lipid bilayer and the particles are serum-stable and have a size of from about 50 to about 150 nm.

An initial solution of coated nucleic acid-lipid complexes is formed by combining the nucleic acid with the cationic lipids in a detergent solution.

In these embodiments, the detergent solution is preferably an aqueous solution of a neutral detergent having a critical micelle concentration of 15-300 mM, more preferably 20-50 mM. Examples of suitable detergents include, for example, N,N'-((octanoylimino)-bis-(trimethylene))-bis-(D-gluconamide) (BIGCHAP); BRIJ 35; Deoxy-BIGCHAP; dodecylpoly(ethylene glycol) ether; Tween 20; Tween 40; Tween 60; Tween 80; Tween 85; Mega 8; Mega 9; Zwittergent® 3-08; Zwittergent® 3-10; Triton X-405; hexyl-, heptyl-, octyl- and nonyl-β-D-glucopyranoside; and heptylthioglucopyranoside; with octyl β-D-glucopyranoside and Tween-20 being the most preferred. The concentration of detergent in the detergent solution is typically about 100 mM to about 2 M, preferably from about 200 mM to about 1.5 M.

The cationic lipids and nucleic acids will typically be combined to produce a charge ratio (+/−) of about 1:1 to about 20:1, preferably in a ratio of about 1:1 to about 12:1, and more preferably in a ratio of about 2:1 to about 6:1. Additionally, the overall concentration of nucleic acid in solution will typically be from about 25 μg/mL to about 1 mg/mL, preferably from about 25 μg/mL to about 200 μm/mL, and more preferably from about 50 μg/mL to about 100 μm/mL. The combination of nucleic acids and cationic lipids in detergent solution is kept, typically at room temperature, for a period of time which is sufficient for the coated complexes to form. Alternatively, the nucleic acids and cationic lipids can be combined in the detergent solution and warmed to temperatures of up to about 37° C. For nucleic acids which are particularly sensitive to temperature, the coated complexes can be formed at lower temperatures, typically down to about 4° C.

In a preferred embodiment, the nucleic acid to lipid ratios (mass/mass ratios) in a formed nucleic acid-lipid particle will range from about 0.01 to about 0.08. The ratio of the starting materials also falls within this range because the purification step typically removes the unencapsulated nucleic acid as well as the empty liposomes. In another preferred embodiment, the nucleic acid-lipid particle preparation uses about 400 μg nucleic acid per 10 mg total lipid or a nucleic acid to lipid ratio of about 0.01 to about 0.08 and, more preferably, about 0.04, which corresponds to 1.25 mg of total lipid per 50 μg of nucleic acid.

The detergent solution of the coated nucleic acid-lipid complexes is then contacted with non-cationic lipids to provide a detergent solution of nucleic acid-lipid complexes and non-cationic lipids. The non-cationic lipids which are useful in this step include, diacylphosphatidylcholine, diacylphosphatidylethanolamine, ceramide, sphingomyelin, cephalin, cardiolipin, and cerebrosides. In preferred embodiments, the non-cationic lipids are diacylphosphatidylcholine, diacylphosphatidylethanolamine, ceramide or sphingomyelin. The acyl groups in these lipids are preferably acyl groups derived from fatty acids having $C_{10}$-$C_{24}$ carbon chains. More preferably the acyl groups are lauroyl, myristoyl, palmitoyl, stearoyl or oleoyl. In particularly preferred embodiments, the non-cationic lipid will be 1,2-sn-dioleoyl-phosphatidylethanolamine (DOPE), palmitoyl oleoyl phosphatidylcholine (POPC), egg phosphatidylcholine (EPC), distearoylphosphatidylcholine (DSPC), cholesterol, or a mixture thereof. In the most preferred embodiments, the nucleic acid-lipid particles will be fusogenic particles with enhanced properties in vivo and the non-cationic lipid will be DSPC or DOPE. In addition, the nucleic acid-lipid particles of the present invention may further comprise cholesterol. In other preferred embodiments, the non-cationic lipids will further comprise polyethylene glycol-based polymers such as PEG 2000, PEG 5000 and polyethylene glycol conjugated to a diacylglycerol, a ceramide or a phospholipid, as described in U.S. Pat. No. 5,820,873 and U.S. Patent Publication No. 20030077829. In further preferred embodiments, the non-cationic lipids will further comprise polyethylene glycol-based polymers such as PEG 2000, PEG 5000 and polyethylene glycol conjugated to a dialkyloxypropyl.

The amount of non-cationic lipid which is used in the present methods is typically about 2 to about 20 mg of total lipids to 50 μg of nucleic acid. Preferably the amount of total lipid is from about 5 to about 10 mg per 50 μg of nucleic acid.

Following formation of the detergent solution of nucleic acid-lipid complexes and non-cationic lipids, the detergent is removed, preferably by dialysis. The removal of the detergent results in the formation of a lipid-bilayer which surrounds the nucleic acid providing serum-stable nucleic acid-lipid particles which have a size of from about 50 nm to about 150 nm, more typically about 100 nm to about 130 nm, most typically about 110 nm to about 115 nm. The particles thus formed do not aggregate and are optionally sized to achieve a uniform particle size.

The serum-stable nucleic acid-lipid particles can be sized by any of the methods available for sizing liposomes. The sizing may be conducted in order to achieve a desired size range and relatively narrow distribution of particle sizes.

Several techniques are available for sizing the particles to a desired size. One sizing method, used for liposomes and equally applicable to the present particles is described in U.S. Pat. No. 4,737,323. Sonicating a particle suspension either by bath or probe sonication produces a progressive size reduction down to particles of less than about 50 nm in size. Homogenization is another method which relies on shearing energy to fragment larger particles into smaller ones. In a typical homogenization procedure, particles are recirculated through a standard emulsion homogenizer until selected particle sizes, typically between about 60 and 80 nm, are observed. In both methods, the particle size distribution can be monitored by conventional laser-beam particle size discrimination, or QELS.

Extrusion of the particles through a small-pore polycarbonate membrane or an asymmetric ceramic membrane is also an effective method for reducing particle sizes to a relatively well-defined size distribution. Typically, the suspension is cycled through the membrane one or more times until the desired particle size distribution is achieved. The particles may be extruded through successively smaller-pore membranes, to achieve a gradual reduction in size.

In another group of embodiments, the present invention provides a method for the preparation of serum-stable nucleic acid-lipid particles, comprising:

(a) preparing a mixture comprising cationic lipids and non-cationic lipids in an organic solvent;

(b) contacting an aqueous solution of nucleic acid with said mixture in step (a) to provide a clear single phase; and (c) removing said organic solvent to provide a suspension of nucleic acid-lipid particles, wherein said nucleic acid is encapsulated in a lipid bilayer, and said particles are stable in serum and have a size of from about 50 to about 150 nm.

The nucleic acids (or plasmids), cationic lipids and non-cationic lipids which are useful in this group of embodiments are as described for the detergent dialysis methods above.

The selection of an organic solvent will typically involve consideration of solvent polarity and the ease with which the solvent can be removed at the later stages of particle formation. The organic solvent, which is also used as a solubilizing agent, is in an amount sufficient to provide a clear single phase mixture of nucleic acid and lipids. Suitable solvents include, but are not limited to, chloroform, dichloromethane, diethylether, cyclohexane, cyclopentane, benzene, toluene, methanol, or other aliphatic alcohols such as propanol, isopropanol, butanol, tert-butanol, iso-butanol, pentanol and hexanol. Combinations of two or more solvents may also be used in the present invention.

Contacting the nucleic acid with the organic solution of cationic and non-cationic lipids is accomplished by mixing together a first solution of nucleic acid, which is typically an aqueous solution, and a second organic solution of the lipids. One of skill in the art will understand that this mixing can take place by any number of methods, for example by mechanical means such as by using vortex mixers.

After the nucleic acid has been contacted with the organic solution of lipids, the organic solvent is removed, thus forming an aqueous suspension of serum-stable nucleic acid-lipid particles. The methods used to remove the organic solvent will typically involve evaporation at reduced pressures or blowing a stream of inert gas (e.g., nitrogen or argon) across the mixture.

The serum-stable nucleic acid-lipid particles thus formed will typically be sized from about 50 nm to about 150 nm, more typically about 100 nm to about 130 nm, most typically about 110 nm to about 115 nm. To achieve further size reduction or homogeneity of size in the particles, sizing can be conducted as described above.

In other embodiments, the methods will further comprise adding nonlipid polycations which are useful to effect the delivery to cells using the present compositions. Examples of suitable nonlipid polycations include, but are limited to, hexadimethrine bromide (sold under the brandname POLY-BRENE®, from Aldrich Chemical Co., Milwaukee, Wis., USA) or other salts of heaxadimethrine. Other suitable polycations include, for example, salts of poly-L-ornithine, poly-L-arginine, poly-L-lysine, poly-D-lysine, polyallylamine and polyethyleneimine.

In certain embodiments, the formation of the nucleic acid-lipid particles can be carried out either in a mono-phase system (e.g., a Bligh and Dyer monophase or similar mixture of aqueous and organic solvents) or in a two-phase system with suitable mixing.

When formation of the complexes is carried out in a mono-phase system, the cationic lipids and nucleic acids are each dissolved in a volume of the mono-phase mixture. Combination of the two solutions provides a single mixture in which the complexes form. Alternatively, the complexes can form in two-phase mixtures in which the cationic lipids bind to the nucleic acid (which is present in the aqueous phase), and "pull" it into the organic phase.

In another embodiment, the present invention provides a method for the preparation of nucleic acid-lipid particles, comprising:

(a) contacting nucleic acids with a solution comprising non-cationic lipids and a detergent to form a nucleic acid-lipid mixture;

(b) contacting cationic lipids with the nucleic acid-lipid mixture to neutralize a portion of the negative charge of the nucleic acids and form a charge-neutralized mixture of nucleic acids and lipids; and (c) removing the detergent from the charge-neutralized mixture to provide the nucleic acid-lipid particles in which the nucleic acids are protected from degradation.

In one group of embodiments, the solution of non-cationic lipids and detergent is an aqueous solution. Contacting the nucleic acids with the solution of non-cationic lipids and detergent is typically accomplished by mixing together a first solution of nucleic acids and a second solution of the lipids and detergent. One of skill in the art will understand that this mixing can take place by any number of methods, for example, by mechanical means such as by using vortex mixers. Preferably, the nucleic acid solution is also a detergent solution. The amount of non-cationic lipid which is used in the present method is typically determined based on the amount of cationic lipid used, and is typically of from about 0.2 to 5 times the amount of cationic lipid, preferably from about 0.5 to about 2 times the amount of cationic lipid used.

In some embodiments, the nucleic acids are precondensed as described in, e.g., U.S. patent application Ser. No. 09/744,103.

The nucleic acid-lipid mixture thus formed is contacted with cationic lipids to neutralize a portion of the negative charge which is associated with the nucleic acids (or other polyanionic materials) present. The amount of cationic lipids used will typically be sufficient to neutralize at least 50% of the negative charge of the nucleic acid. Preferably, the negative charge will be at least 70% neutralized, more preferably at least 90% neutralized. Cationic lipids which are useful in the present invention, include, for example, DLinDMA and, DLenDMA. These lipids and related analogs have been described in U.S. Provisional Patent Application Nos. 60/578,075, filed Jun. 7, 2004; 60/610,746, filed Sep. 17, 2004; and 60/679,427, filed May 9, 2005.

Contacting the cationic lipids with the nucleic acid-lipid mixture can be accomplished by any of a number of techniques, preferably by mixing together a solution of the cationic lipid and a solution containing the nucleic acid-lipid mixture. Upon mixing the two solutions (or contacting in any other manner), a portion of the negative charge associated with the nucleic acid is neutralized. Nevertheless, the nucleic acid remains in an uncondensed state and acquires hydrophilic characteristics.

After the cationic lipids have been contacted with the nucleic acid-lipid mixture, the detergent (or combination of detergent and organic solvent) is removed, thus forming the nucleic acid-lipid particles. The methods used to remove the detergent will typically involve dialysis. When organic solvents are present, removal is typically accomplished by evaporation at reduced pressures or by blowing a stream of inert gas (e.g., nitrogen or argon) across the mixture.

The particles thus formed will typically be sized from about 50 nm to several microns, more typically about 50 nm to about 150 nm, even more typically about 100 nm to about 130 nm, most typically about 110 nm to about 115 nm. To achieve further size reduction or homogeneity of size in the particles, the nucleic acid-lipid particles can be sonicated, filtered or subjected to other sizing techniques which are used in liposomal formulations and are known to those of skill in the art.

In other embodiments, the methods will further comprise adding nonlipid polycations which are useful to effect the lipofection of cells using the present compositions. Examples of suitable nonlipid polycations include, hexadimethrine bromide (sold under the brandname POLYBRENE®, from Aldrich Chemical Co., Milwaukee, Wis., USA) or other salts of hexadimethrine. Other suitable polycations include, for example, salts of poly-L-ornithine, poly-L-arginine, poly-L-lysine, poly-D-lysine, polyallylamine and polyethyleneimine. Addition of these salts is preferably after the particles have been formed.

In another aspect, the present invention provides methods for the preparation of nucleic acid-lipid particles, comprising:
(a) contacting an amount of cationic lipids with nucleic acids in a solution; the solution comprising from about 15-35% water and about 65-85% organic solvent and the amount of cationic lipids being sufficient to produce a +/− charge ratio of from about 0.85 to about 2.0, to provide a hydrophobic nucleic acid-lipid complex;
(b) contacting the hydrophobic, nucleic acid-lipid complex in solution with non-cationic lipids, to provide a nucleic acid-lipid mixture; and
(c) removing the organic solvents from the nucleic acid-lipid mixture to provide nucleic acid-lipid particles in which the nucleic acids are protected from degradation.

The nucleic acids, non-cationic lipids, cationic lipids and organic solvents which are useful in this aspect of the invention are the same as those described for the methods above which used detergents. In one group of embodiments, the solution of step (a) is a mono-phase. In another group of embodiments, the solution of step (a) is two-phase.

In preferred embodiments, the non-cationic lipids are ESM, DOPE, DOPC, polyethylene glycol-based polymers (e.g., PEG 2000, PEG 5000, PEG-modified diacylglycerols, or PEG-modified dialkyloxypropyls), distearoylphosphatidylcholine (DSPC), DPPE, DMPE, 16:0 Monomethyl Phosphatidylethanolamine, 16:0 Dimethyl Phosphatidylethanolamine, 18:1

Trans Phosphatidylethanolamine, 18:0 18:1 Phosphatidylethanolamine (SOPE), 16:0 18:1 Phosphatidylethanolamine, DSPE, cholesterol, or combinations thereof. In still other preferred embodiments, the organic solvents are methanol, chloroform, methylene chloride, ethanol, diethyl ether or combinations thereof In one embodiment, the nucleic acid is a plasmid from which an interfering RNA is transcribed; the cationic lipid is DLindMA, DLenDMA, DODAC, DDAB, DOTMA, DOSPA, DMRIE, DOGS or combinations thereof; the non-cationic lipid is ESM, DOPE, DAG-PEGs, distearoylphosphatidylcholine (DSPC), DPPE, DMPE, 16:0 Monomethyl Phosphatidylethanolamine, 16:0 Dimethyl Phosphatidylethanolamine, 18:1 Trans Phosphatidylethanolamine, 18:0 18:1 Phosphatidylethanolamine (SOPE), 16:0 18:1 Phosphatidylethanolamine DSPE, cholesterol, or combinations thereof (e.g. DSPC and PEG-DAA); and the organic solvent is methanol, chloroform, methylene chloride, ethanol, diethyl ether or combinations thereof As above, contacting the nucleic acids with the cationic lipids is typically accomplished by mixing together a first solution of nucleic acids and a second solution of the lipids, preferably by mechanical means such as by using vortex mixers. The resulting mixture contains complexes as described above. These complexes are then converted to particles by the addition of non-cationic lipids and the removal of the organic solvent. The addition of the non-cationic lipids is typically accomplished by simply adding a solution of the non-cationic lipids to the mixture containing the complexes. A reverse addition can also be used. Subsequent removal of organic solvents can be accomplished by methods known to those of skill in the art and also described above.

The amount of non-cationic lipids which is used in this aspect of the invention is typically an amount of from about 0.2 to about 15 times the amount (on a mole basis) of cationic lipids which was used to provide the charge-neutralized nucleic acid-lipid complex. Preferably, the amount is from about 0.5 to about 9 times the amount of cationic lipids used.

In yet another aspect, the present invention provides nucleic acid-lipid particles which are prepared by the methods described above. In these embodiments, the nucleic acid-lipid particles are either net charge neutral or carry an overall charge which provides the particles with greater gene lipofection activity. Preferably, the nucleic acid component of the particles is a nucleic acid which interferes with the production of an undesired protein. In a preferred embodiment, the nucleic acid comprises an interfering RNA, the non-cationic lipid is egg sphingomyelin and the cationic lipid is DLinDMA or DLenDMA. In a preferred embodiment, the nucleic acid comprises an interfering RNA, the non-cationic lipid is a mixture of DSPC and cholesterol, and the cationic lipid is DLinDMA or DLenDMA. In other preferred embodiments, the non-cationic lipid may further comprise cholesterol.

A variety of general methods for making SNALP-CPLs (CPL-containing SNALPs) are discussed herein. Two general techniques include "post-insertion" technique, that is, insertion of a CPL into for example, a pre-formed SNALP, and the "standard" technique, wherein the CPL is included in the lipid mixture during for example, the SNALP formation steps. The post-insertion technique results in SNALPs having CPLs mainly in the external face of the SNALP bilayer membrane, whereas standard techniques provide SNALPs having CPLs on both internal and external faces. The method is especially useful for vesicles made from phospholipids (which can contain cholesterol) and also for vesicles containing PEG-lipids (such as PEG-DAAs and PEG-DAGs). Methods of making SNALP-CPL, are taught, for example, in U.S. Pat. Nos. 5,705,385, 6,586,410, 5,981, 501 6,534,484; 6,852,334; U.S. Patent Publication No. 20020072121; and WO 00/62813.

IV. Administration of Nucleic Acid-Lipid Particle Formulations

Once formed, the serum-stable nucleic acid-lipid particles of the present invention are useful for the introduction of nucleic acids into cells. Accordingly, the present invention also provides methods for introducing a nucleic acids (e.g., a plasmid or and siRNA) into a cell. The methods are carried out in vitro or in vivo by first forming the particles as described above and then contacting the particles with the cells for a period of time sufficient for delivery of the nucleic acid to the cell to occur.

The nucleic acid-lipid particles of the present invention can be adsorbed to almost any cell type with which they are mixed or contacted. Once adsorbed, the particles can either be endocytosed by a portion of the cells, exchange lipids with cell membranes, or fuse with the cells. Transfer or incorporation of the nucleic acid portion of the particle can take place via any one of these pathways. In particular, when fusion takes place, the particle membrane is integrated into the cell membrane and the contents of the particle combine with the intracellular fluid.

The nucleic acid-lipid particles of the present invention can be administered either alone or in mixture with a physiologically-acceptable carrier (such as physiological saline or phosphate buffer) selected in accordance with the route of administration and standard pharmaceutical practice. Generally, normal saline will be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc.

The pharmaceutical carrier is generally added following particle formation. Thus, after the particle is formed, the particle can be diluted into pharmaceutically acceptable carriers such as normal saline.

The concentration of particles in the pharmaceutical formulations can vary widely, i.e., from less than about 0.05%, usually at or at least about 2-5% to as much as 10 to 30% by weight and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, particles composed of irritating lipids may be diluted to low concentrations to lessen inflammation at the site of administration.

The pharmaceutical compositions of the present invention may be sterilized by conventional, well known sterilization techniques. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, and calcium chloride. Additionally, the particle suspension may include lipid-protective agents which protect lipids against free-radical and lipid-peroxidative damages on storage. Lipophilic free-radical quenchers, such as alphatocopherol and water-soluble iron-specific chelators, such as ferrioxamine, are suitable.

The nucleic acid-lipid particles can be incorporated into a broad range of topical dosage forms including, but not limited to, gels, oils, emulsions, topical creams, pastes, ointments, lotions and the like.

A. In Vivo Administration

Systemic delivery for in vivo gene therapy, i.e., delivery of a therapeutic nucleic acid to a distal target cell via body systems such as the circulation, has been achieved using nucleic acid-lipid particles such as those disclosed in WO 96/40964, U.S. Pat. Nos. 5,705,385, 5,976,567, 5,981,501, and 6,410,328. This latter format provides a fully encapsulated nucleic acid-lipid particle that protects the nucleic acid from nuclease degradation in serum, is nonimmunogenic, is small in size and is suitable for repeat dosing.

For in vivo administration, administration can be in any manner known in the art, e.g., by injection, oral administration, inhalation, transdermal application, or rectal administration. Administration can be accomplished via single or divided doses. The pharmaceutical compositions are preferably administered parenterally, i.e., intraarticularly, intravenously, intraperitoneally, subcutaneously, or intramuscularly. More preferably, the pharmaceutical compositions are administered intravenously or intraperitoneally by a bolus injection (see, e.g., Stadler, et al., U.S. Pat. No. 5,286,634). Intracellular nucleic acid delivery has also been discussed in Straubringer, et al., *Methods Enzymol*, Academic Press, New York. 101:512 (1983); Mannino, et al., *Biotechniques* 6:682 (1988); Nicolau, et al., *Crit. Rev. Ther. Drug Carrier Syst.* 6:239 (1989), and Behr, *Acc. Chem. Res.* 26:274 (1993). Still other methods of administering lipid based therapeutics are described in, for example, Rahman et al., U.S. Pat. No. 3,993,754; Sears, U.S. Pat. No. 4,145,410; Papahadjopoulos et al., U.S. Pat. No. 4,235,871; Schneider, U.S. Pat. No. 4,224,179; Lenk et al., U.S. Pat. No. 4,522,803; and Fountain et al., U.S. Pat. No. 4,588,578. The lipid nucleic acid particles can be administered by direct injection at the site of disease or by injection at a site distal from the site of disease (see, e.g., Culver, HUMAN GENE THERAPY, MaryAnn Liebert, Inc., Publishers, New York. pp. 70-71(1994)).

The compositions of the present invention, either alone or in combination with other suitable components, can be made into aerosol formulations (i.e., they can be "nebulized") to be administered via inhalation (see, Brigham, et al., *Am. J. Sci.* 298(4):278 (1989)). Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

Generally, when administered intravenously, the nucleic acid-lipid formulations are formulated with a suitable pharmaceutical carrier. Many pharmaceutically acceptable carriers may be employed in the compositions and methods of the present invention. Suitable formulations for use in the present invention are found, for example, in REMINGTON'S PHARMACEUTICAL SCIENCES, Mack Publishing Company, Philadelphia, Pa., 17th ed. (1985). A variety of aqueous carriers may be used, for example, water, buffered water, 0.4% saline, 0.3% glycine, and the like, and may include glycoproteins for enhanced stability, such as albumin, lipoprotein, globulin, etc. Generally, normal buffered saline (135-150 mM NaCl) will be employed as the pharmaceutically acceptable carrier, but other suitable carriers will suffice. These compositions can be sterilized by conventional liposomal sterilization techniques, such as filtration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc. These compositions can be sterilized using the techniques referred to above or, alternatively, they can be produced under sterile conditions. The resulting aqueous solutions may be packaged for use or filtered under aseptic conditions and lyophilized, the lyophilized preparation being combined with a sterile aqueous solution prior to administration.

When preparing pharmaceutical preparations of the nucleic acid-lipid particles of the invention, it is preferable to use quantities of the particles which have been purified to reduce or eliminate empty particles or particles with nucleic acid associated with the external surface.

The methods of the present invention may be practiced in a variety of hosts. Preferred hosts include mammalian species, such as avian (e.g., ducks), primates (e.g., humans and chimpanzees as well as other nonhuman primates), canines, felines, equines, bovines, ovines, caprines, rodents (e.g., rats and mice), lagomorphs, and swine.

The amount of particles administered will depend upon the ratio of nucleic acid to lipid; the particular nucleic acid used, the disease state being diagnosed; the age, weight, and condition of the patient and the judgment of the clinician; but will generally be between about 0.01 and about 50 mg per kilogram of body weight; preferably between about 0.1 and about 5 mg/kg of body weight or about $10^8$-$10^{10}$ particles per injection.

B. Cells for Delivery of Interfering RNA

The compositions and methods of the present invention are used to treat a wide variety of cell types, in vivo and in vitro. Suitable cells include, e.g., hematopoietic precursor (stem) cells, fibroblasts, keratinocytes, hepatocytes, endothelial cells, skeletal and smooth muscle cells, osteoblasts, neurons, quiescent lymphocytes, terminally differentiated cells, slow or noncycling primary cells, parenchymal cells, lymphoid cells, epithelial cells, bone cells, and the like.

In vivo delivery of nucleic acid lipid particles encapsulating an interfering RNA is particularly suited for targeting tumor cells of any cell type. In vivo studies show that SNALP's accumulate at tumor sites and predominantly transfect tumor cells. See, Fenske, et al., *Methods Enzymol*, Academic Press, New York 346:36 (2002). The methods and compositions can be employed with cells of a wide variety of vertebrates, including mammals, and especially those of veterinary importance, e.g., canine, feline, equine, bovine, ovine, caprine, rodent, lagomorph, swine, etc., in addition to human cell populations.

To the extent that tissue culture of cells may be required, it is well known in the art. Freshney (1994) (Culture of Animal Cells, a Manual of Basic Technique, third edition Wiley-Liss, New York), Kuchler et al. (1977) Biochemical Methods in Cell Culture and Virology, Kuchler, R. J., Dowden, Hutchinson and Ross, Inc., and the references cited therein provides a general guide to the culture of cells. Cultured cell systems often will be in the form of monolayers of cells, although cell suspensions are also used.

C. Detection of SNALPs

In some embodiments, the nucleic acid-lipid particles are detectable in the subject 8, 12, 24, 48, 60, 72, or 96 hours after administration of the particles. The presence of the particles can be detected in the cells, tissues, or other biological samples from the subject. The particles by be detected, e.g., by direct detection of the particles, detection of the interfering RNA sequence, detection of the target sequence of interest (i.e., by detecting expression or reduced expression of the sequence of interest), or a combination thereof.

1. Detection of Particles

Nucleic acid-lipid particles are detected herein using any methods known in the art. For example, a label can be coupled directly or indirectly to a component of the SNALP or other lipid-based carrier system using methods well known in the art. A wide variety of labels can be used, with the choice of label depending on sensitivity required, ease of conjugation with the SNALP component, stability requirements, and available instrumentation and disposal provisions. Suitable labels include, but are not limited to, spectral labels, such as fluorescent dyes (e.g., fluorescein and derivatives, such as fluorescein isothiocyanate (FITC) and Oregon Green™; rhodamine and derivatives, such Texas red, tetrarhodimine isothiocynate (TRITC), etc., digoxigenin, biotin, phycoerythrin, AMCA, CyDyes™, and the like; radiolabels, such as $^3$H, $^{125}$I, $^{35}$S, $^{14}$C, $^{32}$P, $^{33}$P, etc.; enzymes, such as horse radish peroxidase, alkaline phosphatase, etc.; spectral colorimetric labels, such as colloidal gold or colored glass or plastic beads, such as polystyrene, polypropylene, latex, etc. The label can be detected using any means known in the art.

2. Detection of Nucleic Acids

Nucleic acids are detected and quantified herein by any of a number of means well known to those of skill in the art. The detection of nucleic acids proceeds by well known methods such as Southern analysis, northern analysis, gel electrophoresis, PCR, radiolabeling, scintillation counting, and affinity chromatography. Additional analytic biochemical methods such as spectrophotometry, radiography, electrophoresis, capillary electrophoresis, high performance liquid chromatography (HPLC), thin layer chromatography (TLC), hyperdiffusion chromatography, may also be employed The selection of a nucleic acid hybridization format is not critical. A variety of nucleic acid hybridization formats are known to those skilled in the art. For example, common formats include sandwich assays and competition or displacement assays. Hybridization techniques are generally described in "Nucleic Acid Hybridization, A Practical Approach," Ed. Hames, B. D. and Higgins, S. J., IRL Press, 1985.

The sensitivity of the hybridization assays may be enhanced through use of a nucleic acid amplification system which multiplies the target nucleic acid being detected. In vitro amplification techniques suitable for amplifying sequences for use as molecular probes or for generating nucleic acid fragments for subsequent subcloning are known. Examples of techniques sufficient to direct persons of skill through such in vitro amplification methods, including the polymerase chain reaction (PCR) the ligase chain reaction (LCR), Qβ-replicase amplification and other RNA polymerase mediated techniques (e.g., NASBA™) are found in Sambrook, et al., In *Molecular Cloning: A Laboratory Manual*, Cold Spring Harbor Laboratory Press, 2000, and Ausubel et al., SHORT PROTOCOLS IN MOLECULAR BIOLOGY, eds., Current Protocols, a joint venture between Greene Publishing Associates, Inc. and John Wiley & Sons, Inc., (2002), as well as Mullis et al. (1987), U.S. Pat. No. 4,683,202; PCR Protocols A Guide to Methods and Applications (Innis et al. eds) Academic Press Inc. San Diego, Calif. (1990) (Innis); Arnheim & Levinson (Oct. 1, 1990), C&EN 36; The *Journal Of NIH Research*, 3:81 (1991); (Kwoh et al., *Proc. Natl. Acad. Sci. USA*, 86:1173 (1989); Guatelli et al., *Proc. Natl. Acad. Sci. USA*, 87:1874 (1990); Lomell et al., *J. Clin. Chem.*, 35:1826 (1989); Landegren et al., *Science*, 241:1077 (1988); Van Brunt, *Biotechnology*, 8:291 (1990); Wu and Wallace, *Gene*, 4:560 (1989); Barringer et al., *Gene*, 89:117 (1990), and Sooknanan and Malek, *Biotechnology*, 13:563 (1995). Improved methods of cloning in vitro amplified nucleic acids are described in Wallace et al., U.S. Pat. No. 5,426,039. Other methods described in the art are the nucleic acid sequence based amplification (NASBA™, Cangene, Mississauga, Ontario) and Q Beta Replicase systems. These systems can be used to directly identify mutants where the PCR or LCR primers are designed to be extended or ligated only when a select sequence is present. Alternatively, the select sequences can be generally amplified using, for example, nonspecific PCR primers and the amplified target region later probed for a specific sequence indicative of a mutation.

Oligonucleotides for use as probes, e.g., in in vitro amplification methods, for use as gene probes, or as inhibitor components are typically synthesized chemically according to the solid phase phosphoramidite triester method described by Beaucage and Caruthers, *Tetrahedron Letts.*, 22(20):1859 1862 (1981), e.g., using an automated synthesizer, as described in Needham VanDevanter et al., *Nucleic Acids Res.*, 12:6159 (1984). Purification of oligonucleotides, where necessary, is typically performed by either native acrylamide gel electrophoresis or by anion exchange HPLC as described in Pearson and Regnier, *J. Chrom.*, 255:137 149 (1983). The sequence of the synthetic oligonucleotides can be verified using the chemical degradation method of Maxam and Gilbert (1980) in Grossman and Moldave (eds.) Academic Press, New York, *Methods in Enzymology*, 65:499.

An alternative means for determining the level of transcription is in situ hybridization. In situ hybridization assays are well known and are generally described in Angerer et al., *Methods Enzymol.*, 152:649 (1987). In an in situ hybridization assay cells are fixed to a solid support, typically a glass slide. If DNA is to be probed, the cells are denatured with heat or alkali. The cells are then contacted with a hybridization solution at a moderate temperature to permit annealing of specific probes that are labeled. The probes are preferably labeled with radioisotopes or fluorescent reporters.

D. Transfection Efficiency

The transfection efficiency of the nucleic acid-lipid particles described herein can be optimized using an ERP assay. For example, the ERP assay can be used to distinguish the effect of various cationic lipids, non-cationic lipids, and bilayer stabilizing components of the SNALPs based on their relative effect on binding/uptake or fusion with/destabilization of the endosomal membrane. This assay allows one to determine quantitatively how each component of the SNALPs affects transfection efficacy, thereby optimizing the SNALPs. As explained herein, the Endosomal Release Parameter or, alternatively, ERP is defined as:

Reporter Gene Expression/Cell
SNALP Uptake/Cell

It will be readily apparent to those of skill in the art that any reporter gene (e.g., luciferase, β-galactosidase, green fluorescent protein, etc.) can be used. In addition, the lipid component (or, alternatively, any component of the SNALP or lipid-based formulation) can be labeled with any detectable label provided the does inhibit or interfere with uptake into the cell. Using the ERP assay of the present invention, one of skill in the art can assess the impact of the various lipid components (e.g., cationic lipid of Formula I or II, non-cationic lipid, PEG-lipid derivative, PEG-DAA conjugate, ATTA-lipid derivative, calcium, CPLs, cholesterol, etc.) on cell uptake and transfection efficiencies, thereby optimizing the SPLP or other lipid-based carrier system. By comparing the ERPs for each of the various SPLPs or other lipid-based formulations, one can readily determine the optimized system, e.g., the SPLP or other lipid-based formulation that has the greatest uptake in the cell coupled with the greatest transfection efficiency.

Suitable labels for carrying out the ERP assay of the present invention include, but are not limited to, spectral labels, such as fluorescent dyes (e.g., fluorescein and derivatives, such as fluorescein isothiocyanate (FITC) and Oregon Green; rhodamine and derivatives, such Texas red, tetrarhodimine isothiocynate (TRITC), etc., digoxigenin, biotin, phycoerythrin, AMCA, CyDyes$^\theta$, and the like; radiolabels, such as $^3$H, $^{125}$I, $^{35}$S, $^{14}$C, $^{32}$P, $^{33}$P, etc.; enzymes, such as horse radish peroxidase, alkaline phosphatase, etc.; spectral colorimetric labels, such as colloidal gold or colored glass or plastic beads, such as polystyrene, polypropylene, latex, etc. The label can be coupled directly or indirectly to a component of the SNALP using methods well known in the art. As indicated above, a wide variety of labels can be used, with the choice of label depending on sensitivity required, ease of conjugation with the SNALP component, stability requirements, and available instrumentation and disposal provisions.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

The following examples are offered to illustrate, but not to limit the claimed invention.

Example 1

Materials and Methods

Materials:
DPPS, 1,2-Distearoyl-sn-glycero-3-phosphocholine (DSPC) and cholesterol were purchased from Avanti Polar Lipids (Alabaster, Ala.). TNS was obtained from Sigma-Aldrich Canada (Oakville, ON). RiboGreen was obtained from Molecular Probes (Eugene, Oreg.). The alkyl mesylates were purchased from Nu-Chek Prep, Inc. (Elysian, Minn., USA). siRNA (anti-luciferase and mismatch control) was purchased from Dharmacon (Lafayette, Colo., USA). The anti-luciferase sense sequence was 5'-GAUUAUGUC-CGGUUAUGUAUU-3' (SEQ ID NO:1). The anti-luciferase antisense sequence was 5'-UACAUAACCGGA-CAUAAUCUU-3' (SEQ ID NO:2). All other chemicals were purchased from Sigma-Aldrich (Oakville, ON, Canada).

Synthesis of DSDMA and DODMA:

DSDMA and DODMA were synthesized using the respective alkyl bromides with methodology derived from that of a DOTMA precursor (Feigner et al, *PNAS USA*, 84, 7413-7417 (1987)). 3-(Dimethylamino)-1,2-propanediol (714 mg, 6 mmol) and 95% sodium hydride (NaH, 1.26 g, 50 mmol) were stirred in benzene (30 mL) under argon for 30 minutes. The correct (either oleyl or stearyl) alkyl bromide (5.0 g, 15 mmol) was added and the reaction refluxed under argon for 18 hours. The reaction mixture was then cooled in an ice bath while quenching via the slow addition of ethanol. Following dilution with a further 150 mL of benzene, the mixture was washed with distilled water (2×150 mL) and brine (150 mL), using ethanol (~20 mL) to aid phase separation if necessary. The organic phase was dried over magnesium sulphate and evaporated. The crude product was purified on a silica gel (Kiesel Gel 60) column eluted with chloroform containing 0-5% methanol. Column fractions were analyzed by thin layer chromatography (TLC) (silica gel, chloroform/methanol 9:1 v/v, visualized with molybdate) and fractions containing pure product ($R_f$=0.5) were pooled and concentrated. The product was decolorized by stirring for 30 minutes in a suspension of activated charcoal (1 g) in ethanol (75 mL) at 60° C. The charcoal was removed by filtration through Celite, and the ethanol solution concentrated to typically yield 2.4 g (65%) of pure product. $^1$H-NMR (DSDMA): $\delta_H$ 3.65-3.32 (m, 7H, OCH, 3×OCH$_2$), 2.45-2.31 (m, 2H, NCH$_2$), 2.27 (s, 6H, 2×NCH$_3$), 1.61-1.45 (m, 4H, OCH$_2$C$\underline{H}_2$), 1.40-1.17 (m, 60H, H$_{stearyl}$), 0.86 (t, 6H, CH$_2$C$\underline{H}_3$). $^1$H-NMR (DODMA): $\delta_H$ 5.4-5.27 (m, 4H, 2×C$\underline{H}$=C$\underline{H}$), 3.65-3.35 (m, 7H, OCH, 3×OCH$_2$), 2.47-2.33 (m, 2H, NCH$_2$), 2.28 (s, 6H, 2×NCH$_3$), 2.06-1.94 (m, 8H, 4×C$\underline{H}_2$CH=CH), 1.61-1.50 (m, 4H, OCH$_2$C$\underline{H}_2$), 1.38-1.20 (m, 48H, H$_{oleyl}$), 0.88 (t, 6H, CH$_2$C$\underline{H}_3$).

Synthesis of 1,
2-DiLinoleyloxy-N,N-dimethylaminopropane
(DLinDMA) and
1,2-Dilinolenyloxy-N,N-dimethylaminopropane
(DLenDMA)

3-(Dimethylamino)-1,2-propanediol (714 mg, 6 mmol) and 95% sodium hydride (NaH, 1.26 g, 50 mmol) are stirred in benzene (30 mL) under nitrogen for 30 minutes. Linoleyl mesylate (5.0 g, 15 mmol) is added and the reaction refluxed under nitrogen for 3 hours. The reaction mixture is then cooled in an ice bath while quenching via the slow addition of ethanol. Following dilution with a further 150 mL of benzene, the mixture is washed with distilled water (2×150 mL) and brine (150 mL). The organic phase is dried over magnesium sulphate and evaporated to give the crude product.

The crude product is purified on a silica gel (Kiesel Gel 60) column eluted with 0-5% methanol in chloroform. Column fractions are analyzed by thin layer chromatography (TLC) (silica gel, chloroform/methanol 9:1 v/v, visualized with molybdate dip) and fractions containing purified product ($R_f$=0.5) are pooled and concentrated.

Decolorization and further purification of DLinDMA is effected with a second column, this time eluting with 20-50% ethyl acetate in hexane. Column fractions are analyzed by TLC (silica gel, ethyl acetate/hexane 1:1 v/v, visualized with molybdate) and fractions containing pure product ($R_f$=0.4) are pooled and concentrated. The procedure described herein typically yields 2.2 g (60%) of pure product.

For synthesis of DLenDMA, linolenyl mesylate is substituted for linoleyl mesylate and the remainder of the synthesis, decolorization, and purification reactions is carried out as described above.

Synthesis of PEG$_{2000}$-C-DMA:

PEG-C-DMA was synthesized as follows. In brief, a $C_{14}$ lipid anchor was prepared by first alkylating the hydroxyl groups of 3-allyloxypropane-1,2-diol with myristyl bromide. The allyl group was subsequently removed via palladium catalysis, resulting in the $C_{14}$ hydroxyl lipid. The hydroxyl group was converted to the primary amine by mesylation and amination to yield 1,2-dimyristyloxypropyl-3-amine, the lipid anchor. Conjugation with PEG was effected by treating monomethoxy poly(ethylene glycol) (average molecular weight 2000) with an excess of diphosgene to form the chloroformate. Addition of the $C_{14}$ amine lipid anchor and stirring overnight yielded PEG$_{2000}$-C-DMA, referred to here as PEG-C-DMA.

SNALP Preparation:

SNALP with a lipid composition of DSPC:Chol:PEG-C-DMA:Cationic Lipid (20:48:2:30 molar percent) were prepared using the spontaneous vesicle formation by ethanol dilution method [Jeffs et al., *Pharm. Res.* In Press (2005)]. The sample's were diafiltered against 100 mL of PBS (20 wash volumes) using a cross flow ultrafiltration cartridge (Amersham Biosciences, Piscataway, N.J.) and sterile filtered through Acrodisc 0.2 μm Posidyne filters (Pall Corp., Ann Arbor, Mich.). The siRNA concentration of final samples was determined using the RiboGreen assay and a siRNA standard curve. Particle size and polydispersity was determined using a Malvern Instruments Zetasizer 3000HSA (Malvern, UK). Nucleic acid encapsulation was determined using a RiboGreen assay, comparing fluorescence in the presence and absence of Triton X-100. RiboGreen fluorescence was measured using a Varian Eclipse Spectrofluorometer (Varian Inc) with $\lambda_{ex}$=500 nm, $\lambda_{em}$=525 nm.

TNS Assay:

20 μM of SNALP lipid and 6 μM of TNS were mixed in a fluorescence cuvette in 2 mL of 20 mM sodium phosphate, 25 mM citrate, 20 mM ammonium acetate and 150 mM NaCl, at a pH that was varied from 4.5 to 9.5. Fluorescence was determined at each pH using a Varian Eclipse Spectrofluorometer (Varian Inc) with settings of $\lambda_{ex}$=322 nm, $\lambda_{em}$=431 nm. Fluorescence for each system at the various pH was then normalized to the value at pH 4.5. The p$K_a$ values are the point at which 50% of the molecules present are charged. By assuming that minimum fluorescence represents zero charge, and maximum fluorescence represents 100% charge, p$K_a$ can be estimated by measuring the pH at the point exactly half way between the values of minimum and maximum charge.

$^{31}$P Nuclear Magnetic Resonance Spectroscopy:

Multilamellar vesicles (MLV) were prepared comprising DPPS and cationic lipid at a molar ratio of 1:1. This was accomplished by drying the lipids from chloroform solution, transferring to 10 mm NMR tubes, and hydrating in 1.5 mL of 10 mM sodium citrate, pH 4. Free induction decays (FIDs) corresponding to 1000 scans were obtained with a 3.0 μs, 60 o pulse with a 1 s interpulse delay and a spectral width of 25000 Hz. A gated two-level proton decoupling was used to ensure sufficient decoupling with minimum sample heating. An exponential multiplication corresponding to 50 Hz of line broadening was applied to the FIDs prior to Fourier transformation. The sample temperature (+/−1° C.) was regulated using a Bruker B-VT1000 variable temperature unit. Chemical shifts were referenced to 85% phosphoric acid as an external standard.

In Vitro Transfection:

Cells were cultured in MEM (Invitrogen) containing 10% fetal bovine serum (FBS) (CanSera) and 0.25 mg/mL G418 (Invitrogen). Neuro2A-G cells (Neuro2A cells stably transfected to express luciferase [R. E. Kingston. in *Current Protocols in Molecular Biology*, Vol. 2, pp. 9.1.4-9.1.9, John Wiley & Sons, Inc. (1997)]) were plated at a concentration of $4 \times 10^4$ cells per well in 24-well plates and grown overnight. Cells were treated with SNALP at doses of 0.0625-1.0 µg/mL nucleic acid (AntiLuc Active or Mismatch Control) and incubated for 48 hours at 37° C. and 5% $CO_2$. Cells were then washed with PBS and lysed with 200 µL 250 mM sodium phosphate containing 0.1% Triton X-100. The luciferase activity for each well was determined using Luciferase Reagent (Promega) and a standard luciferase protein (Roche). The luminescence for each was measured using a Berthold MicroLumatPlus LB96V plate luminometer. The resulting luciferase activity was then normalized for the amount of protein using the Micro BCA assay kit (Pierce). Luciferase knockdown relative to a control was then determined for each system.

Cellular Uptake:

SNALP were prepared incorporating the non-exchangeable tritium-labeled lipid cholesteryl hexadecyl ether (3H—CHE) (11.1 µCi/µmol total lipid) [Bally et al., in *Liposome Technology*, Vol. III, pp. 27-41, CRC Press (1993)]. Neuro2A cells (ATCC, VA, USA) were plated in 12 well plates at $1.6 \times 10^5$ cells per well in minimal essential media. The following day, media was removed and replaced with media containing radiolabelled SNALP at 0.5 m/mL nucleic acid. After 24 hours, the media and unincorporated SNALP were removed, adherent cells gently washed 4 times with PBS, and then lysed with 600 µL Lysis Buffer (250 mM phosphate with 0.1% Triton X-100). The resulting cell lysate (500 µL) was added to glass scintillation vials containing 5 mL Picofluor 40 (Perkin Elmer) and $^3$H—CHE was determined using a Beckman LS6500 scintillation counter (Beckman Instruments). The protein content of cell lysates was determined using the Micro BCA assay (Pierce). Uptake was expressed as a percentage of the total amount of activity applied to the cells per mg of cellular protein.

Uptake of SNALP Containing Cy3-Labeled siRNA:

SNALP were Formulated as previously described, but using siRNA labelled with the fluorophore Cy3 (Cy3-siRNA was a gift of Sirna Therapeutics Inc, Boulder, Colo.). The encapsulation, siRNA concentration, and particle size were determined as described.

For the uptake study, $8 \times 10^4$ Neuro2A-G cells were grown overnight on 4-well chamber slides (B D Falcon, Mississauga, ON) in MEM containing 0.25 mg/mL G418. DSDMA, DODMA, DLinDMA, and DLenDMA SNALP containing Cy3-siRNA, as well as naked Cy3-siRNA and unlabeled DSDMA SNALP were placed on the cells at 0.5 µg/mL siRNA. After a 4 hour incubation with the transfection media, the cells were washed with PBS, then with MEM containing G418 and finally with PBS once more. The cells were then fixed in a 4% paraformaldehyde solution in PBS for 10 min at room temperature. The cells were washed with PBS and stained with 300 nM DAPI (Molecular Probes, Eugene, Oreg.) in PBS for 5 minutes. The cells were washed with PBS, the mounting media ProLong Gold Antifade Reagent (Molecular Probes, Eugene, Oreg.) applied and a cover slip added. The cells were viewed using an Olympus BX60 Microscope modified for fluorescence capabilities. Cy3 fluorescence within the cells was visualized using a rhodamine cube set (Microgen Optics, Redding, Calif.) and the DAPI fluorescence was visualized using a DAPI cube set (Carsen Group, Markham, ON). Digital pictures were captured using an Olympus DP70 camera system. Pictures of the cells were taken at exposure times of ¼ sec when examining Cy3 fluorescence and 1/80 sec when examining DAPI fluorescence.

Example 2

SNALP Formulations Encapsulating siRNA

This example demonstrates encapsulating siRNA in SNALP formulated with either short- or long-chain PEG-DAG and produced by continuously mixing organic lipid and aqueous buffer solutions. PEG-DAG lipids employed were PEG-dimyristylglycerol ($C_{14}$) (PEG-DMG) and PEG-distearylglycerol ($C_{18}$) (PEG-DSG). Anti-β-galactosidase (β-gal) siRNA encapsulated in DSPC:Cholesterol:DODMA: PEG-DMG/PEG-DSG SNALP by this method resulted in ≥90% encapsulation (Ribogreen Assay) and ~120 nm particle size (Malvern sizer). The preparations had the following characteristics:

4 ml prep: anti-B-gal siRNA in DSPC:Chol:DODMA: PEG-DMG liposomes
  Initial mix=94% encapsulation
  Post dilution mix=98% encapsulation
  Post incubation mix=97% encapsulation
  Post overnight dialysis=96% encapsulation
  Particle size=109.7 nm
  Polydispersity=0.14
8 ml prep: anti-B-gal siRNA in DSPC:Chol:DODMA: PEG-DMG liposomes
  Post dilution & incubated mix=89%
  Post overnight dialysis=91%
  Particle size=127.5 nm
  Polydispersity=0.11
8 ml prep: anti-B-gal siRNA in DSPC: Chol:DODMA: PEG-DSG liposomes
  Post dilution & incubated mix=90%
  Post overnight dialysis=90%
  Post sterile-filter=90%
  Particle size=111.6 nm
  Polydispersity=0.24

Example 3

Figure 4:
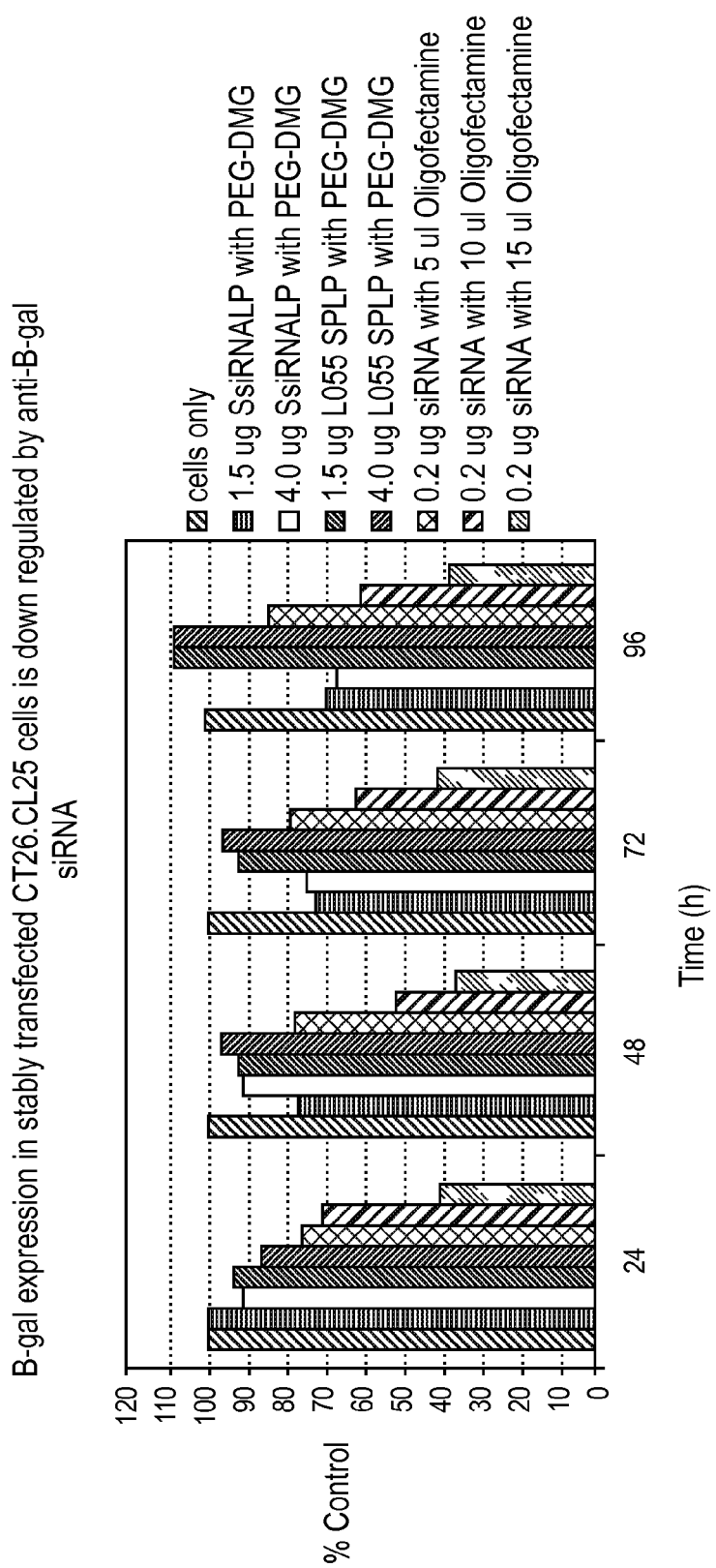
FIG. 4 illustrates downregulating β-galactosidase expression in CT26.CL25 cells via in vitro delivery of encapsulated anti-β-galactosidase siRNA in DSPC:Cholesterol:DODMA:PEG-DMG liposomes.
Figure 5:
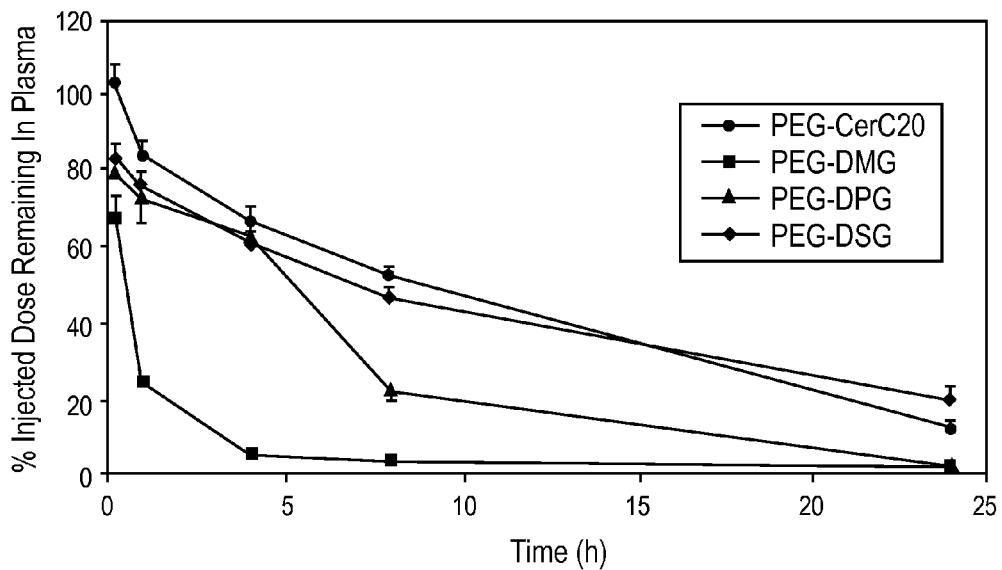
FIG. 5 illustrates that clearance studies with LUVs showed that SNALPs containing PEG-DAGs were comparable to SNALPs containing PEG-CeramideC20.
Figure 6:
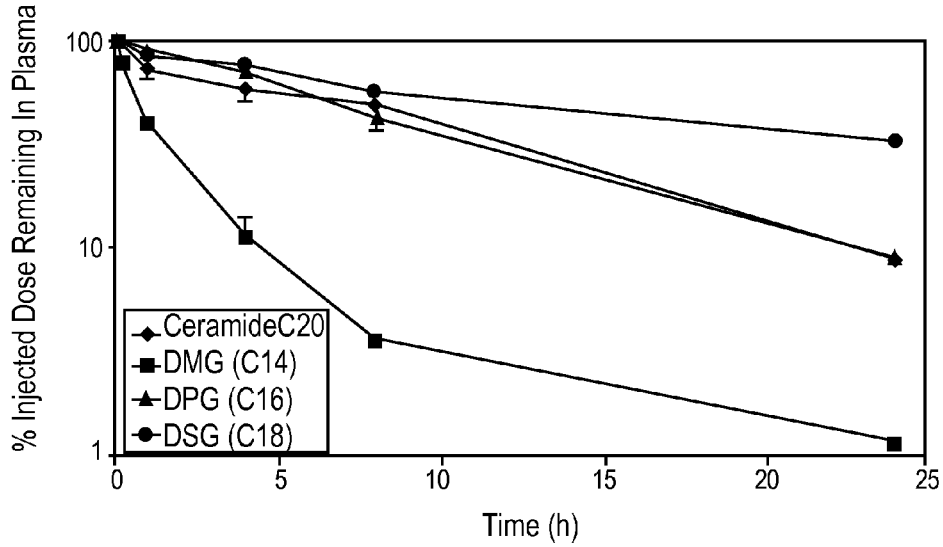
FIG. 6 illustrates the pharmacokinetic properties of SNALPs containing PEG-DAGs.
Figure 7A:
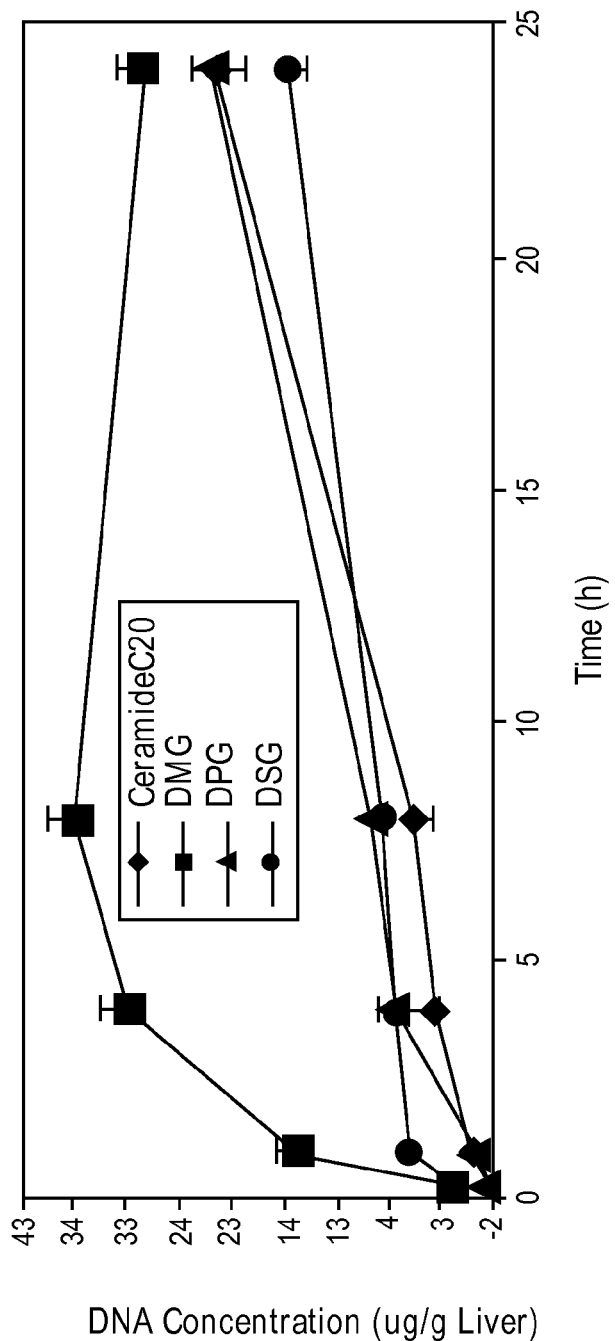
FIGS. 7A-7D illustrate the biodistribution properties of SNALPs containing PEG-DAGs.
Figure 7B:
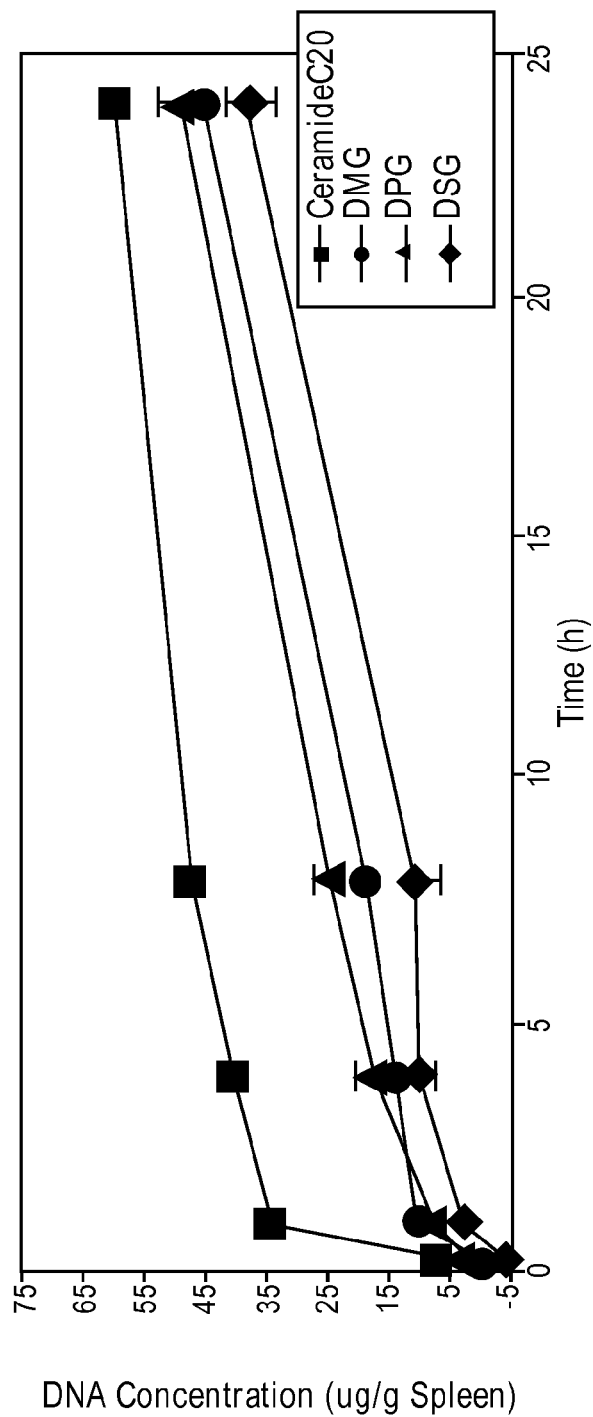
Figure 7C:
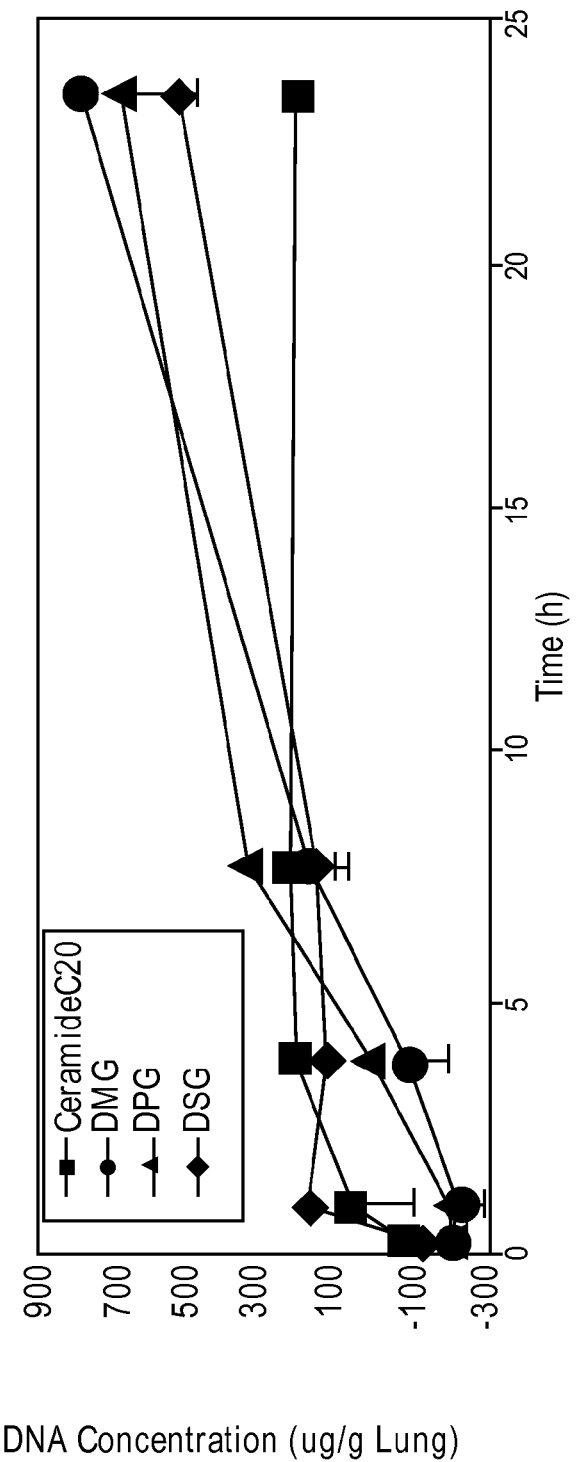
Figure 7D:
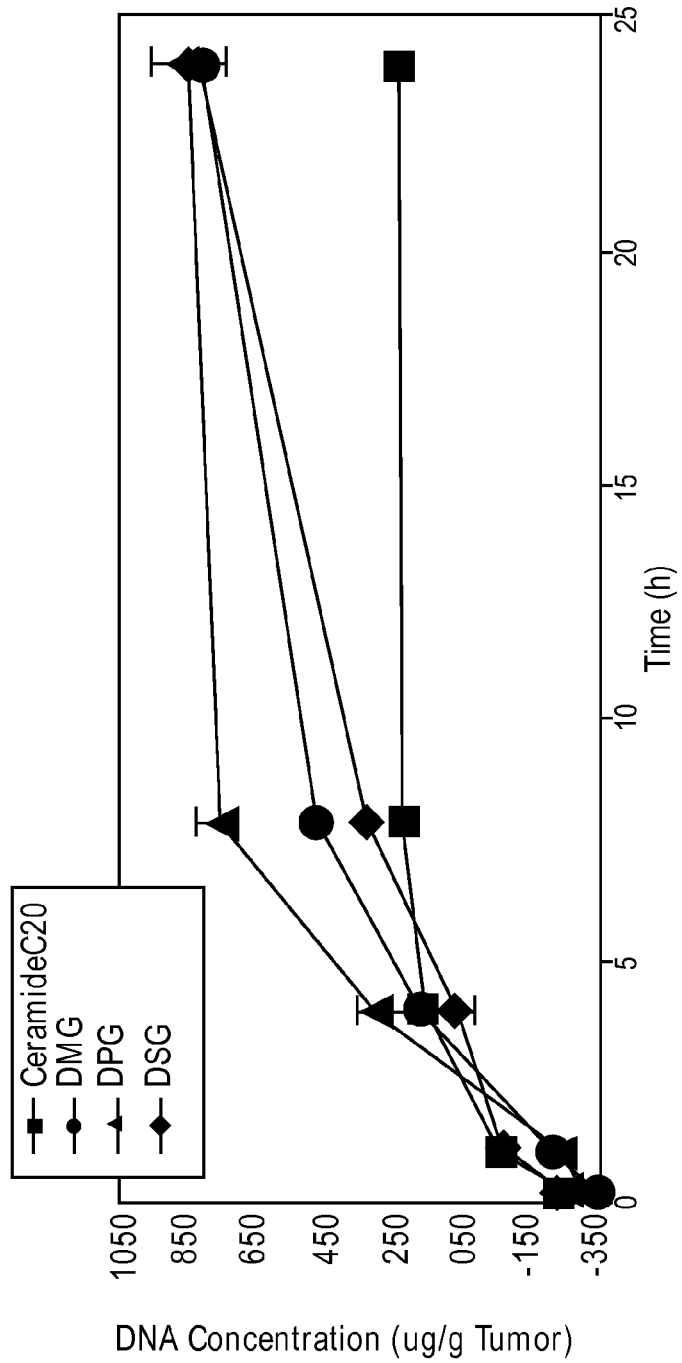

Downregulation of Intracellular Expression in Cells by Delivering In Vitro an SNALP Formulation Encapsulating siRNA This example demonstrates downregulation of β-Gal expression in CT26.CL25 cells delivered in vitro DSPC: Cholesterol:DODMA:PEG-DMG liposomes encapsulating anti-β-Gal siRNA. The results are depicted in FIG. 4.

In vitro delivery of 0.2 µg Oligofectamine-encapsulated anti-β-Gal siRNA decreased β-Gal activity by about 60% in comparison to unexposed control cells. Encapsulating 1.5 µg anti-β-Gal siRNA in DSPC:Cholesterol:DODMA:PEG-DMG liposomes decreased β-Gal activity by about 30% in comparison to unexposed control cells.

Example 4

Assays for Serum Stability

Lipid/therapeutic nucleic acid particles formulated according to the above noted techniques can be assayed for serum stability by a variety of methods.

For instance, in a typical DNase 1 digestion, 1 μg of DNA encapsulated in the particle of interest is incubated in a total volume of 100 μL of 5 mM HEPES, 150 mM NaCl, 10.0 mM $MgCl_2$ pH 7.4. DNase treated samples are treated with either 100 or 10 U of DNase I (Gibco-BRL). 1.0% Triton X-100 can be added in control experiments to ensure that lipid formulations are not directly inactivating the enzyme. Samples are incubated at 37° C. for 30 min after which time the DNA is isolated by addition of 500 μL of DNAZOL followed by 1.0 mL of ethanol. The samples are centrifuged for 30 min at 15,000 rpm in a tabletop microfuge. The supernatant is decanted and the resulting DNA pellet is washed twice with 80% ethanol and dried. This DNA is resuspended in 30 μL of TE buffer. 20 μL of this sample is loaded on a 1.0% agarose gel and subjected to electrophoresis in TAE buffer.

In a typical serum assay, 50 μg of DNA in free, encapsulated, or encapsulated+0.5% Triton X100 was aliquoted into 1.5 mL Eppendorf tubes. To the tubes were added 45 μl normal murine or human serum, dH2O (to make final volume 50 The tubes were sealed with parafilm and incubated at 37° C. A sample of the free, encapsulated, or encapsulated+0.5% Triton X100 not digested by nuclease (standard) was frozen in liquid nitrogen in an Eppendorf tube and stored at −20° C. Aliquots were taken at various time points, added to GDP buffer containing proteinase K (133 μg/mL) and immediately frozen in liquid nitrogen to stop the reaction. Once all of the time points were collected, the samples were incubated at 55° C. in a waterbath to activate proteinase K enabling it to denature any remaining exonuclease. Proteinase K digested samples were applied to polyacrylamide gels to assess levels of exonuclease degradation.

Particles disclosed above demonstrate serum stability by showing less than 5% and preferably undetectable amounts of DNA degradation (partial or total) as a result of such treatment, even in the presence of 100 U DNase 1. This compares favorably to free DNA, which is completely degraded, and plasmid/lipid complexes (such as DOTMA or DODAC:DOPE complexes), wherein DNA is substantially (i.e., greater than 20%, often 80%) degraded after such treatment.

Example 5

Characterization of SNALPs

This example describes disease site targeting and gene expression resulting from intravenous administration of SNALP encapsulating plasmids in tumor bearing mice.

Plasmid DNA was encapsulated in small (diameter ~70 nm) nucleic acid-lipid particles (i.e., SNALP) comprising comprise of one plasmid per particle, encapsulated within a lipid bilayer stabilized by the presence of a bilayer stabilizing component, such as a poly(ethyleneglycol) (PEG) coating. SNALP exhibited extended circulation lifetimes following intravenous administration and promoted delivery of intact plasmid to distal tumor sites resulting in reporter gene expression at the disease site.

Figure 8:
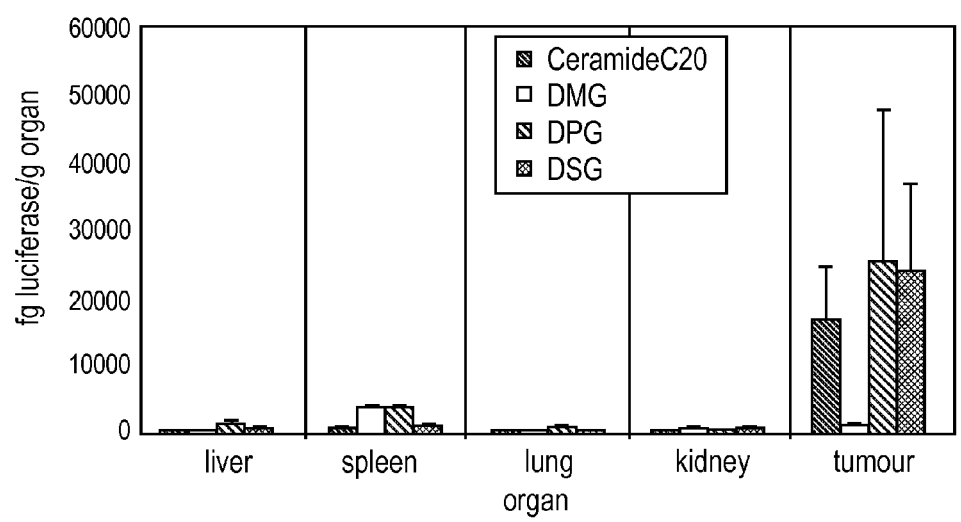
FIG. 8 illustrates the luciferase gene expression 24 hrs post IV administration of SPLPs containing PEG-CeramideC$_{20}$ versus PEG-DAGs in Neuro-2a Tumor Bearing Male A/J Mice.
Figure 9:
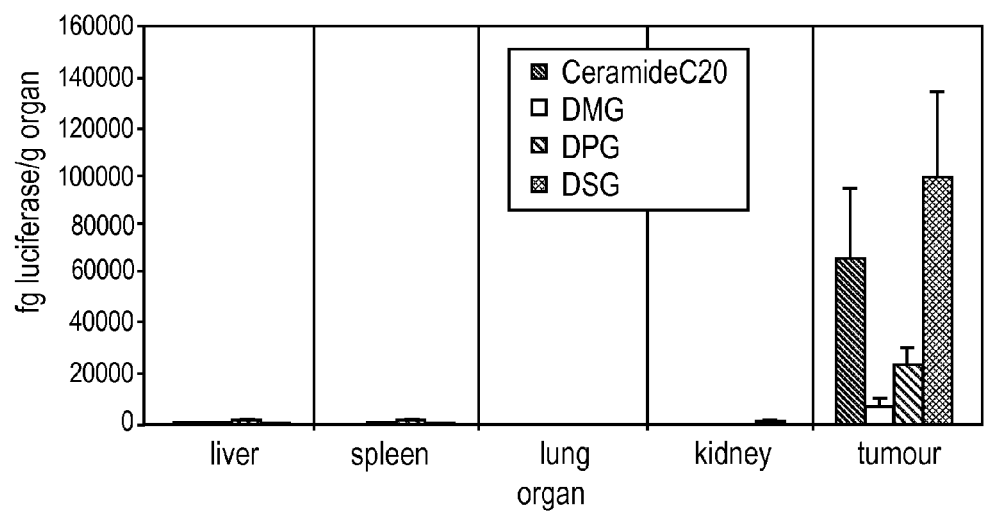
FIG. 9 illustrates the luciferase gene expression 48 hrs post IV administration of SPLPs containing PEG-CeramideC$_{20}$ versus PEG-DAGs in Neuro-2a Tumor Bearing Male A/J Mice.
Figure 10:
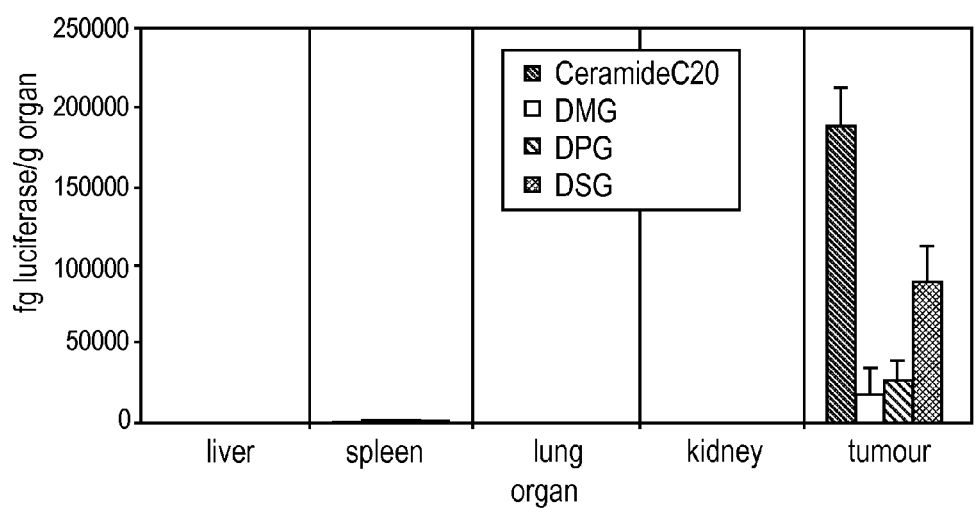
FIG. 10 illustrates the luciferase gene expression 72 hrs post IV administration of SPLPs containing PEG-CeramideC$_{20}$ versus PEG-DAGs in Neuro-2a Tumor Bearing Male A/J Mice.

SNALP with long circulation times accumulated to levels corresponding to five to ten percent of the total injected dose per gram of tumor or greater than 1000 copies of plasmid DNA per cell, giving rise to levels of gene expression that were more than two orders of magnitude greater than those observed in any other tissue. Interestingly, although the liver accumulated 20-30% of the total injected dose, very low levels of gene expression were observed in the liver. This is thought to be due to the limited hepatocellular uptake of the PEG-ylated SNALP. See, FIGS. 8-10.

The in vivo delivery and transfection potential of nucleic acid-lipid particles containing a bilayer stabilizing component was further enhanced through the incorporation of a cationic PEG lipid (CPL) consisting of a DSPE anchor, $PEG_{3400}$ spacer chain and a cationic head group. When CPL were incorporated into SNALP at concentrations of 2 to 4 mol % the resulting CPL-SNALP were of a similar size and stability as native SNALP. Incorporation of CPL resulted in a dramatic increase in intracellular delivery and a concomitant increase in transfection activity measured both in vitro and in vivo. Specifically, CPL-SNALP yielded $10^5$-fold more in vitro gene expression than native SNALP. When CPL-SNALP were administered intravenously they yielded a substantial (250 fold) increase in hepatic gene expression compared to native SNALP. The increase in CPL-SNALP potency was specific to the liver. The levels of gene expression measured in the lung, kidney, spleen or heart remained unchanged, contributing to more than two orders of magnitude differential in the gene expression measured in the liver vs. other organs.

These results illustrate the potential for modulating the delivery properties of PEG-lipid containing systems while retaining the stability and small uniform size required to achieve systemic gene delivery. In particular they demonstrate that disease site targeting and tissue specific gene expression can be re-programmed by altering the lipid composition of non-viral gene delivery systems.

Example 6

SNALPs Containing PEG-DAG Conjugates

This example demonstrates the preparation of a series of PEG-diacylglycerol lipids (PEG-DAG) SNALPs. In this example, the encapsulated nucleic acid is a plasmid.

PEG-DAG SNALP were prepared incorporating 10 mol percent PEG-dilaurylglycerol ($C_{12}$), PEG-dimyristylglycerol ($C_{14}$), PEG-dipalmitoylglycerol ($C_{16}$) or PEG-disterylglycerol ($C_{18}$) and evaluated for in vitro transfection activity, pharmacokinetics and the biodistribution of gene expression resulting from systemic administration in tumor bearing mice. PEG-DAG lipid containing SNALP demonstrated a similar relationship between acyl chain length and in vitro transfection activity to those containing PEG-ceramides. Shorter acyl chain anchors (dimyristyl ($C_{14}$) and dipalmitoyl ($C_{16}$)) resulted in SNALP particles that were less stable but have higher transfection activity in vitro than those incorporating longer acyl chain anchors (disteryl ($C_{18}$)). Evaluation of the pharmacokinetics of PEG-DAG containing SNALP confirmed a correlation between the stability of the PEG lipid component and the circulation lifetime of SNALP. SNALP containing PEG-dimyristylglycerol ($C_{14}$), PEG-dipalmitoylglycerol ($C_{16}$) and PEG-disterylglycerol ($C_{18}$) demonstrated circulation half-lives of 0.75, 7 and 15 hours respectively. Extended circulation lifetime in turn correlates with an increase in tumor delivery and concomitant gene expression.

Upon intravenous administration, PEG-disterylglycerol ($C_{18}$) containing SNALP bypass so-called 'first pass' organs, including the lung, and elicited gene expression in distal tumor tissue. The level of reporter gene expression observed in tumors represents a 100 to 1000-fold differential over that observed in any other tissue. This compared well with the behavior of SNALP containing PEG-ceramide $C_{20}$. The incorporation of PEG-DAG in SNALP confirmed that small size, low surface charge and extended circulation lifetimes are prerequisite to the passive disease site targeting leading to accumulation of plasmid DNA and gene expression in tumors following systemic administration of non-viral transfection systems. See, FIGS. 5-10.

Materials and Methods

Materials

DOPE and DSPC were obtained from Northern Lipids (Vancouver, BC). DODAC and the PEG-diacylglycerols were manufactured by Inex Pharmaceuticals (Burnaby, BC). The other materials, HEPES, OGP and $^3$H-cholesteryl hexadecyl ether, were obtained from a number of different commercial sources.

DOPE:DODAC:PEG-Diacylglycerols (82.5:7.5:10) large unilamellar vesicles were prepared via detergent dialysis in Hepes Buffered Saline (150 mM NaCl and 10 mM HEPES) for 48 hours. Lipid stock solutions were prepared in ethanol and then dried down to create a lipid film which was reconstituted in final 200 mM OGP. LUVs were labeled with $^3$H-cholesteryl hexadecyl ether at 1 uCi/1 mg lipid. Particle sizes were determined by nicomp analysis. Radioactivity was determined by scintillation counting with Picofluor20.

SNALP containing PEG-Diacyglycerols were formulated via detergent dialysis by varying the salt concentration to maximize the percent of DNA encapsulation. Optimal salt concentration was chosen for the 48 hour detergent dialysis. Empty vesicles were removed by one step sucrose centrifugation. 3.5% sucrose was used to separate out the empty particles from the plasmid-containing PEG-Diacylglycerol formulations except for PEG-Dimyristylglycerol containing SNALP which used 5.0% sucrose. Empty vesicles migrated to the top of the tube which were fractioned out and removed.

In Vitro Transfection $5 \times 10^4$ cells/ml were plated onto 24-well plates (1 ml). Cells were left to grow for 24 hours. 500 µl of transfection media (2.5 µg/well) was added and then incubated for stated timepoints. Transfection media was aspirated after timepoint and then exposed to complete media for another 24 hours at 37° C. in 5.0% $CO_2$. Complete media was removed. Cells were washed with PBS twice and stored at −70° C. until day of experiment. Cells were lysed with 150 µl of 1×CCLR containing protease inhibitors. Plates were shaken for 5 minutes. 20 µl of each sample were assayed in duplicate on a 96-well luminescence plate for luciferase activity.

Pharmacokinetics, Biodistribution, and In Vivo Gene Expression

Pharmacokinetics and biodistribution were all determined by normalizing the data to the quantity of radioactivity present. Approximately 500 µl of blood was obtained by cardiac puncture. Red blood cells and plasma were separated by centrifugation (4° C., 3000 rpm, 10 minutes) and 100 µl of plasma was used to determine radioactive counts. Organs were harvested at specified timepoints and homogenized in lysing matrix tubes (Fast Prep, 2×15 seconds, 4.5 intensity) to assay a portion of the mixture.

Gene expression was determined by luciferase assay. Organs were harvested, homogenized, and kept on ice throughout the experiment. Lysates were centrifuged (10, 000 rpm, 5 minutes) and 20 µl of supernatant were assayed in duplicate on a 96-well luminescence plate for luciferase activity. The results are depicted in FIGS. 7-10.

In Vitro Gene Silencing

Figure 17:
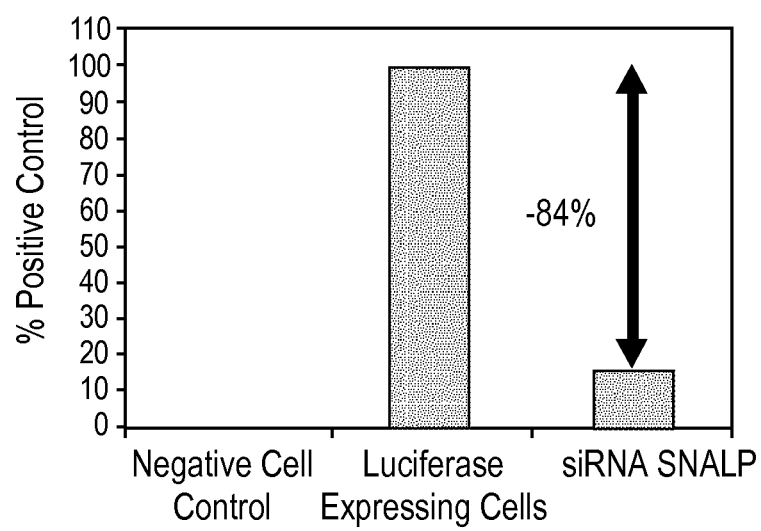
FIG. 17 illustrates in vitro data demonstrating silencing of luciferase expression in luciferase expressing cells treated with SPLPs comprising a PEG-lipid conjugate and containing a plasmid encoding luciferase under the control of the CMV promoter and SNALPs comprising a PEG-lipid conjugate and containing anti-luciferase siRNA.
Figure 18:
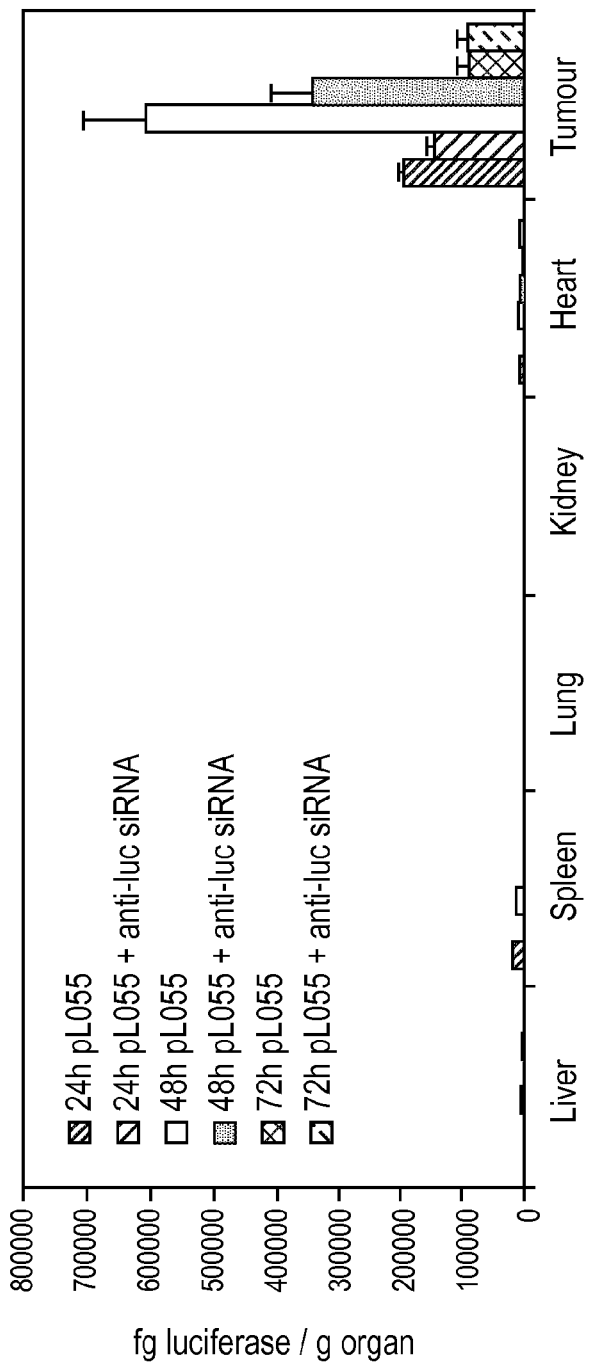
FIG. 18 illustrates in vivo data demonstrating silencing of luciferase expression in Neuro-2a tumor bearing male A/J mice treated with SPLPs comprising a PEG-DAA conjugate and containing a plasmid encoding luciferase under the control of the CMV promoter and SNALPs comprising a PEG-DAA conjugate and containing anti-luciferase siRNA.
Figure 19:
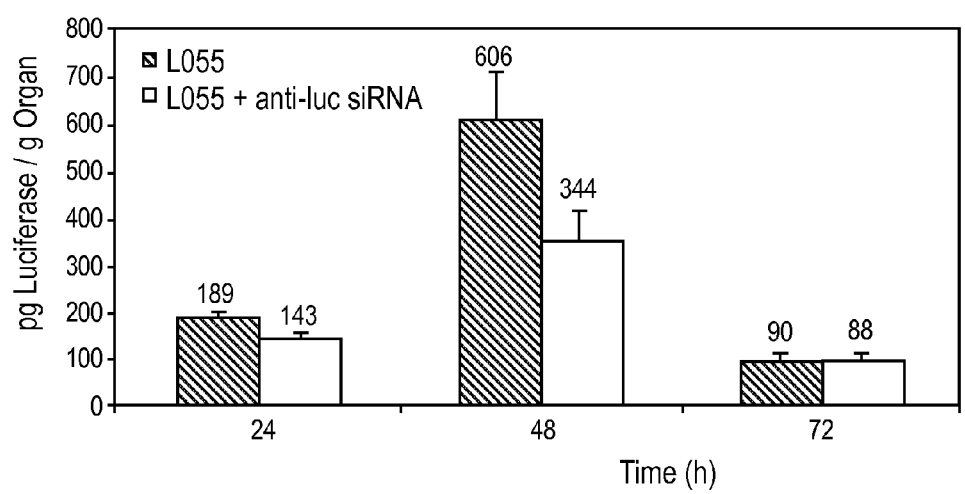
FIG. 19 illustrates in vivo data demonstrating silencing of luciferase expression in Neuro-2a tumor bearing male A/J mice treated with SPLPs comprising a PEG-DAA conjugate and containing a plasmid encoding luciferase under the control of the CMV promoter and SNALPs comprising a PEG-DAA conjugate and containing anti-luciferase siRNA.
Figure 20:
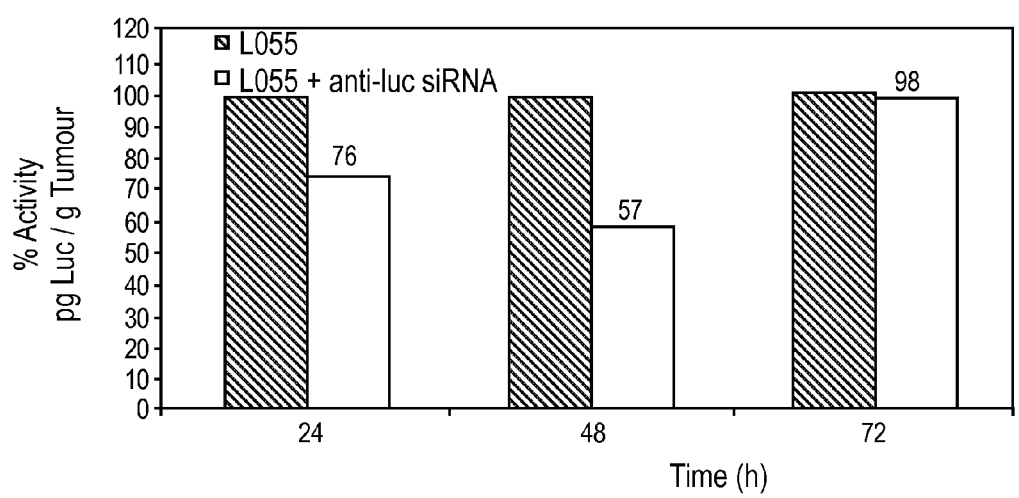
FIG. 20 illustrates in vivo data demonstrating silencing of luciferase expression in Neuro-2a tumor bearing male A/J mice treated with SPLPs comprising a PEG-DAA conjugate and containing a plasmid encoding luciferase under the control of the CMV promoter and SNALPs comprising a PEG-DAA conjugate and containing anti-luciferase siRNA.
Figure 21:
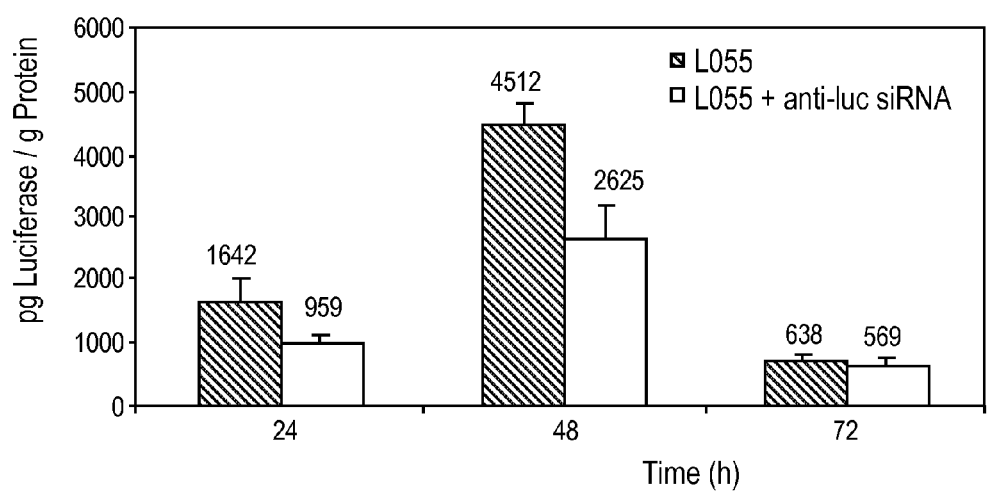
FIG. 21 illustrates in vivo data demonstrating silencing of luciferase expression in Neuro-2a tumor bearing male A/J mice treated with SPLPs comprising a PEG-DAA conjugate and containing a plasmid encoding luciferase under the control of the CMV promoter and SNALPs comprising a PEG-DAA conjugate and containing anti-luciferase siRNA.
Figure 22:
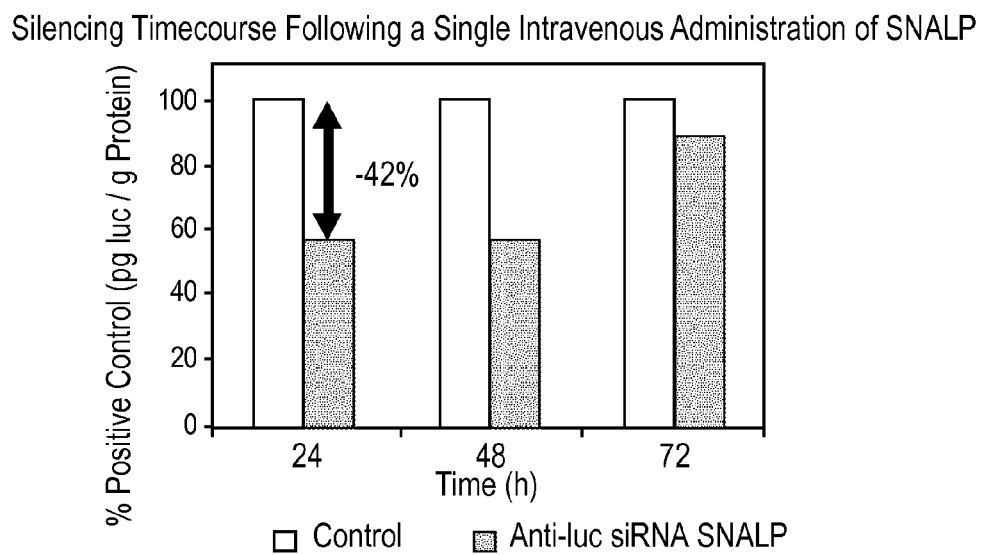
FIG. 22 illustrates in vivo data demonstrating silencing of luciferase expression in Neuro-2a tumor bearing male A/J mice treated with SPLPs comprising a PEG-DAA conjugate and containing a plasmid encoding luciferase under the control of the CMV promoter and SNALPs comprising a PEG-DAA conjugate and containing anti-luciferase siRNA.

Cells were transfected with SPLP comprising PEG-lipid conjugates and containing a plasmid encoding luciferase under the control of the CMV promoter and SNALPs containing anti-luciferase siRNA, according to the methods described above. Gene expression was determined by luciferase assay. The results are depicted in FIG. 17.

Example 7

Expression of Nucleic Acids Encapsulated in SPLP Comprising PEG-Dialkyloxypropyl Conjugates This example describes experiments comparing expression of nucleic acids encapsulated in SPLP comprising PEG-dialkyloxypropyl conjugates. All SPLP formulations comprise a plasmid encoding luiferase under the control of the CMV promoter (pLO55).

| Group | # Mice | Tumor | Route | Treatment | Route | # Doses | Timepoint | ASSAY*** |
|---|---|---|---|---|---|---|---|---|
| A | 4 | Neuro-2a | SC | PBS | IV | 1 | 48 hrs | Body weights, Blood analyses, Luciferase activity |
| B | 5 | Neuro-2a | SC | SPLP PEG-DSG | IV | 1 | 48 hrs | |
| C | 5 | Neuro-2a | SC | SPLP PEG-A-DSA | IV | 1 | 48 hrs | |
| D | 5 | Neuro-2a | SC | SPLP PEG-A-DPA | IV | 1 | 48 hrs | |
| E | 5 | Neuro-2a | SC | SPLP PEG-A-DMA | IV | 1 | 48 hrs | |

The lipids (DSPC:CHOL:DODMA:PEG-Lipid) were present in the SPLP in the following molar ratios (20:55:15:10). The following formulations were made:

A: PBS sterile filtered, 5 mL.
B: pL055-SPLP with PEG-DSG, 2 mL at 0.50 mg/mL.
C: pL055-SPLP with PEG-A-DSA, 2 mL at 0.50 mg/mL.
D: pL055-SPLP with PEG-A-DPA, 2 mL at 0.50 mg/mL.
E: pL055-SPLP with PEG-A-DMA, 2 mL at 0.50 mg/mL.

| Group | # Mice | Seeding date | Treatment | Injection date | Collection date |
|---|---|---|---|---|---|
| A | 4 | Day 0 | PBS | Day 12 | Day 14 |
| B | 5 | Day 0 | SPLP PEG-DSG | Day 12 | Day 14 |
| C | 5 | Day 0 | SPLP PEG-A-DSA | Day 12 | Day 14 |
| D | 5 | Day 0 | SPLP PEG-A-DPA | Day 12 | Day 14 |
| E | 5 | Day 0 | SPLP PEG-A-DMA | Day 12 | Day 14 |

$1.5 \times 10^6$ Neuro2A cells were administered to each mouse on day 0. When the tumors were of a suitable size (200-400 mm$^3$), mice were randomized and treated with one dose of an SPLP formulation or PBS by intravenous (IV) injection. Dose amounts are based on body weight measurements taken on the day of dosing. 48 hours after SPLP administration, the mice were sacrificed, their blood was collected, and the following tissues were collected weighed, immediately frozen and stored at −80° C. until further analysis: tumor, liver (cut in 2 halves), lungs, spleen and heart.

Figure 11:
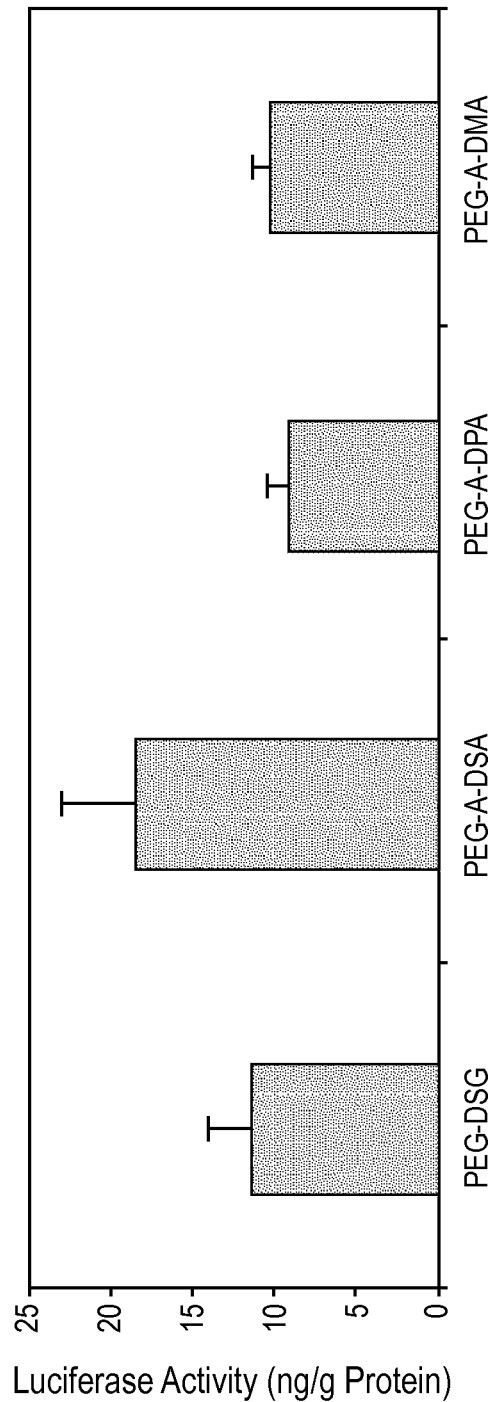
FIG. 11 illustrates data showing luciferase gene expression in tumors 48 hours after intravenous administration of SPLP comprising PEG-DAA conjugates and PEG-DAG conjugates.
Figure 12:
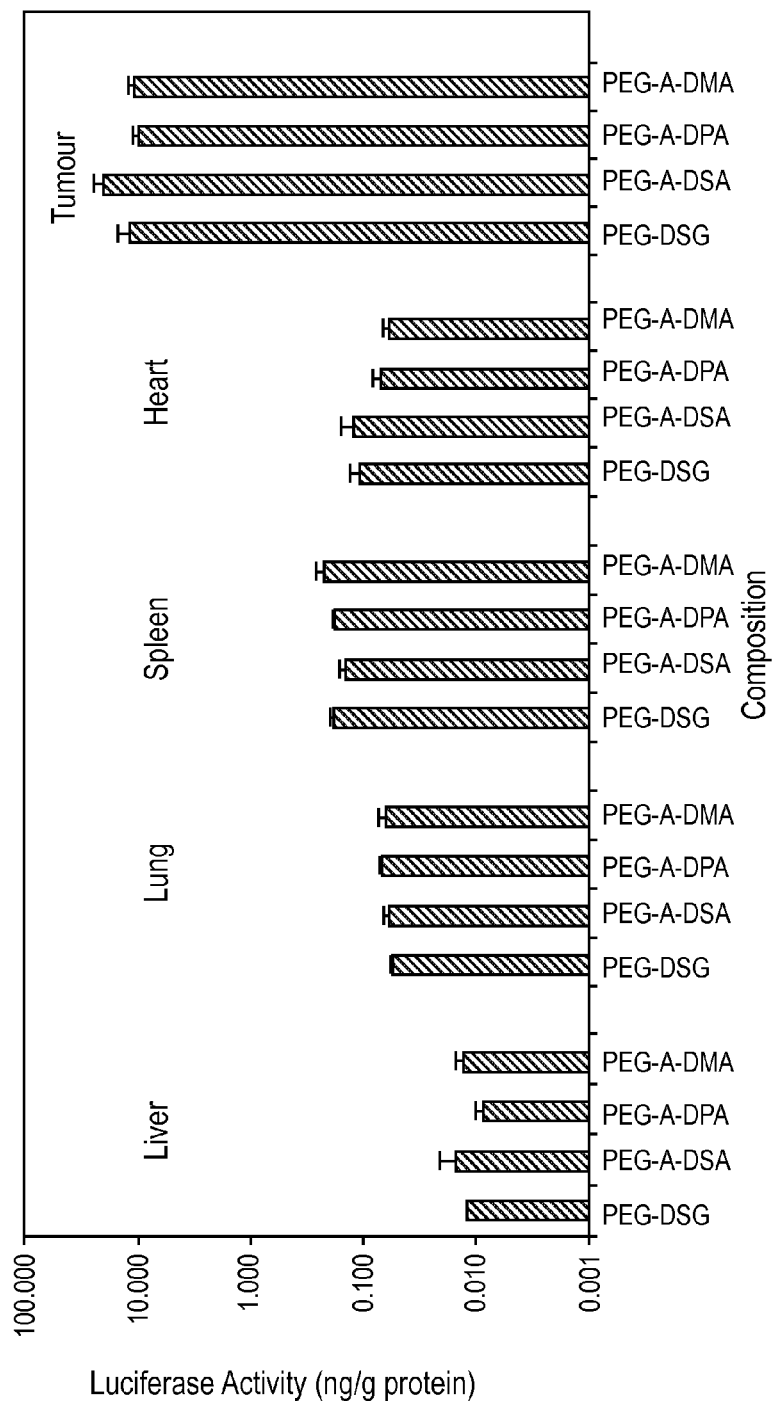
FIG. 12 illustrates data showing luciferase gene expression in liver, lung, spleen, heart, and tumor following intravenous administration of SPLP comprising PEG-DAA conjugates and PEG-DAG conjugates.
Figure 13:
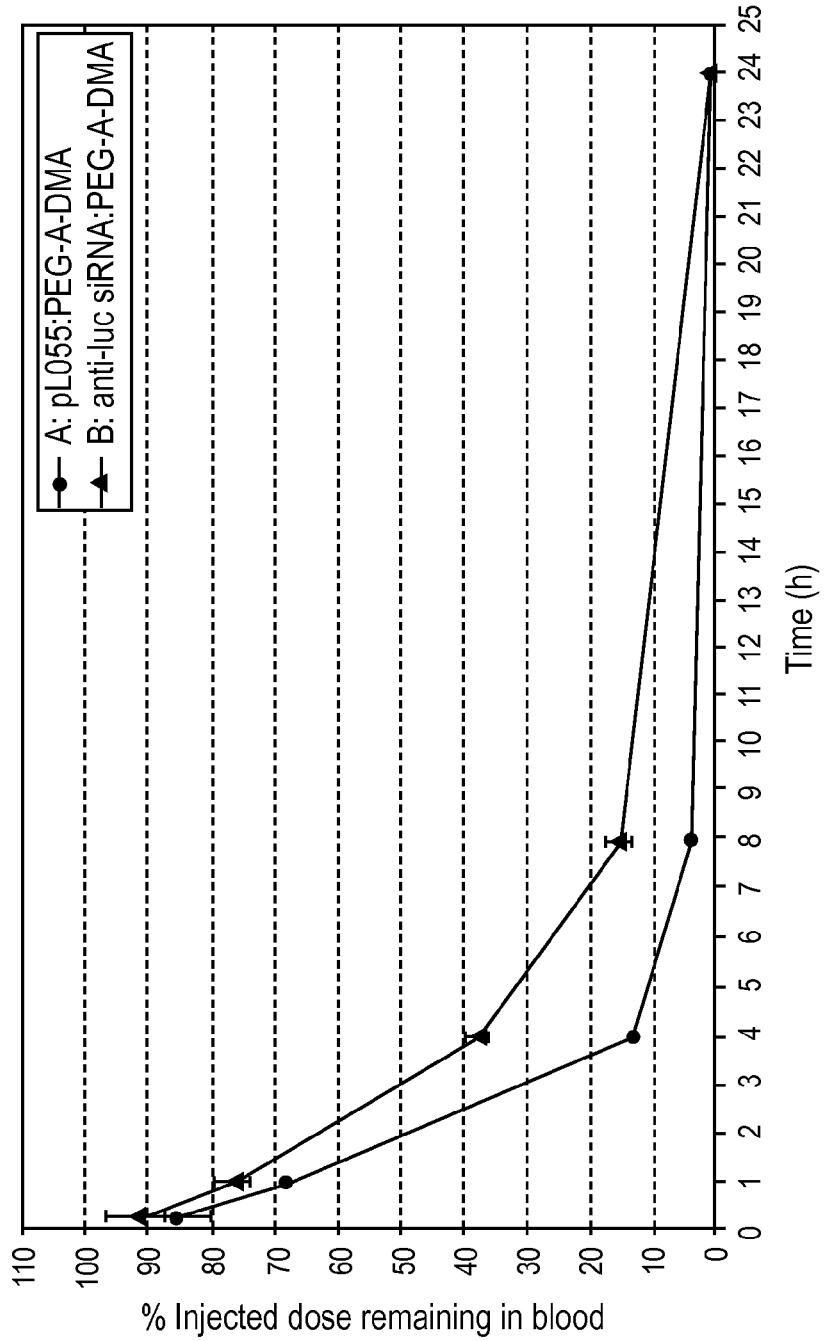
FIG. 13 illustrates data from clearance studies in Neuro-2a tumor bearing male A/J mice after administration of SPLPs comprising a PEG-DAA conjugate and containing a plasmid encoding luciferase under the control of the CMV promoter and SNALPs comprising a PEG-DAA conjugate and containing anti-luciferase siRNA.
Figure 14:
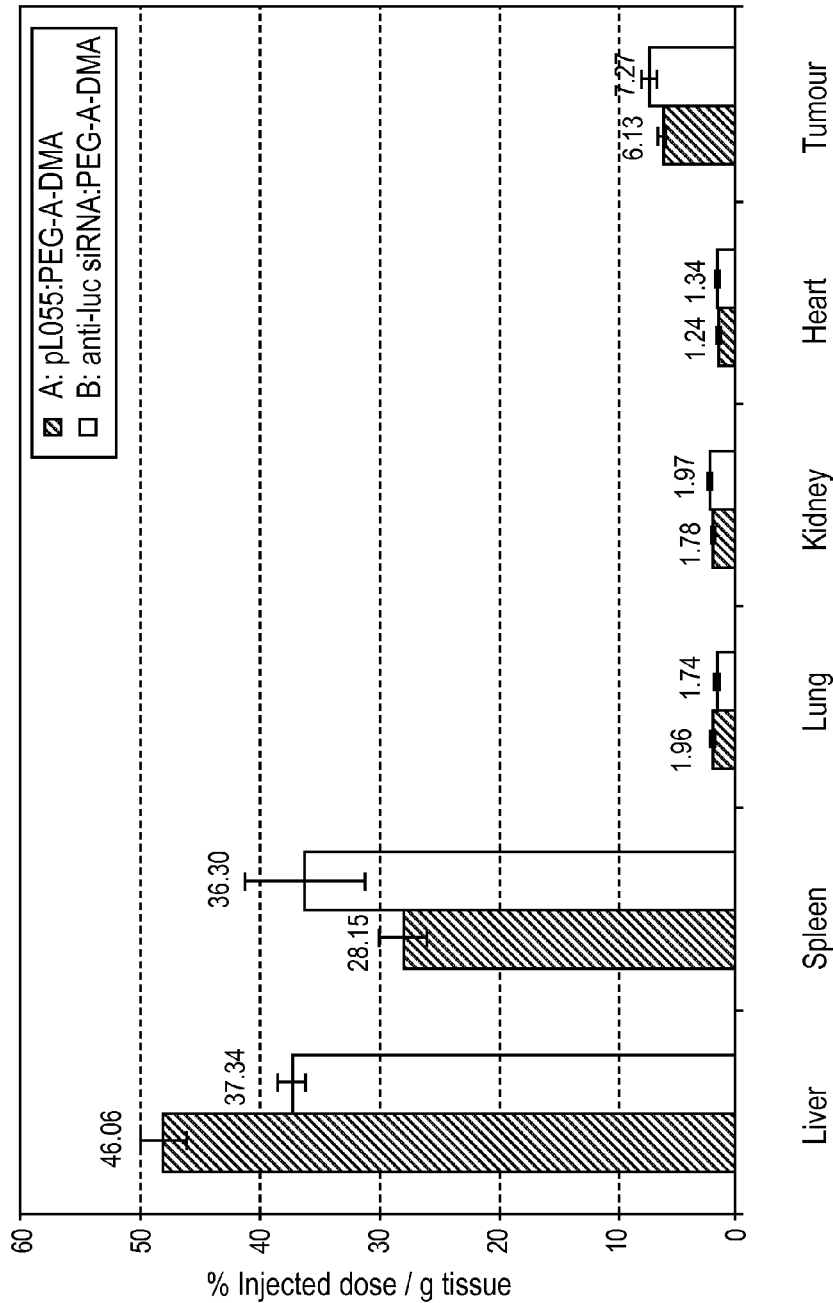
FIG. 14 illustrates data from studies of the pharmacokinetic properties of SPLPs comprising a PEG-DAA conjugate and containing a plasmid encoding luciferase under the control of the CMV promoter and SNALPs comprising a PEG-DAA conjugate and containing anti-luciferase siRNA in Neuro-2a tumor bearing male A/J mice.
Figure 15:
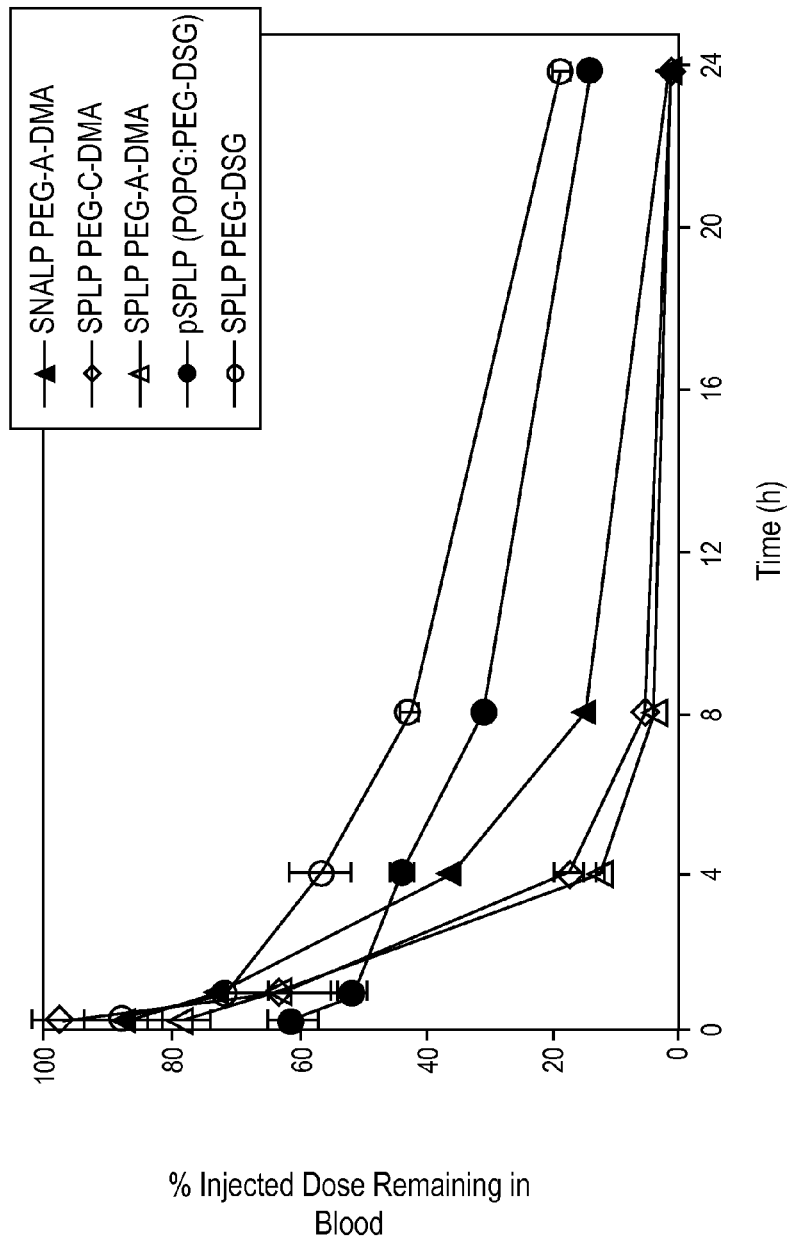
FIG. 15 illustrates data from clearance studies in Neuro-2a tumor bearing male A/J mice after administration of SPLPs comprising a PEG-DAA conjugate or a PEG-DAG conjugate and containing a plasmid encoding luciferase under the control of the CMV promoter, pSPLPs comprising a PEG-DAG conjugate and containing a plasmid encoding luciferase under the control of the CMV promoter and SNALPs comprising a PEG-DAA conjugate and containing anti-luciferase siRNA.
Figure 16:
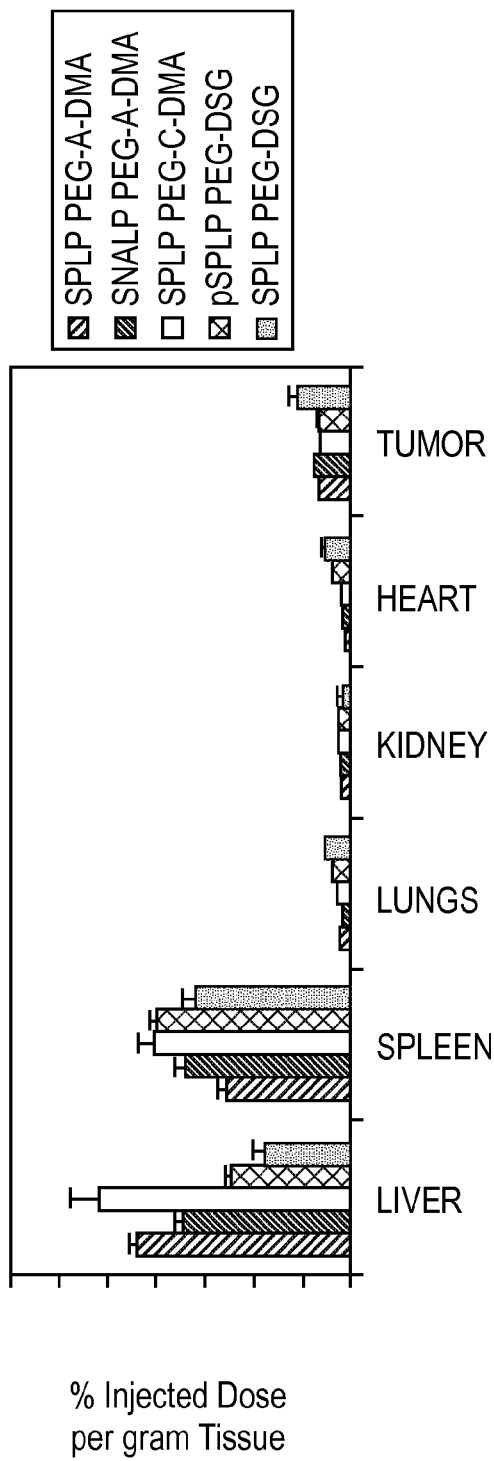
FIG. 16 illustrates data from studies of the pharmacokinetic properties of SPLPs comprising a PEG-DAA conjugate or a PEG-DAG conjugate and containing a plasmid encoding luciferase under the control of the CMV promoter, pSPLPs comprising a PEG-DAG conjugate and containing a plasmid encoding luciferase under the control of the CMV promoter and SNALPs comprising a PEG-DAA conjugate and containing anti-luciferase siRNA in Neuro-2a tumor bearing male A/J mice.

Gene expression in collected tissues was determined by assaying for enzymatic activity of expressed luciferase reporter protein. The results are shown in FIGS. 11 and 12.

The results indicate that SPLP comprising PEG-dialkyloxypropyls (i.e., PEG-DAA) can conveniently be used to transfect distal tumor to substantially the same extent as SPLP comprising PEG-diacylglycerols. Moreover, the transfection levels seen with SPLP containing PEG-dialkyloxypropyl are similar to those seen with SPLP containing PEG-diacylglycerols (e.g. PEG-DSG). It was also shown that similar to the PEG-diacylglycerol system, very little transfection occurred in non-tumor tissues. Moreover, the SPLP comprising PEG-dialkyloxypropyls exhibit reduced toxicity compared to other SPLP formulations.

Example 8

SNALPs Containing PEG-Dialkyloxypropyl Conjugates

This example described experiments analyzing the biodistribution (local and systemic) and pharmacokinetics of a series of PEG-dialkyloxypropyl lipids SNALPs (i.e., SPLP containing encapsulated siRNA.

Local Biodistribution

To determine the local distribution of SPLP resulting from systemic administration of anti-β galactosidase siRNA containing SNALP in Neuro-2a tumor bearing mice via fluorescent microscopy.
A: PBS
B: anti-βgal siRNA-Rhodamine-PE labeled-DSPC:Chol:DODMA:PEG-A-DMA SNALP (1:20:54:15:10)

| Group | Mice | Cells | Treatment | Timepoint | Assay |
|---|---|---|---|---|---|
| A | 2 | Neuro2A | PBS | 24 hr | Fluorescent Photomicroscopy |
| B | 5 | Neuro2A | anti-Bgal siRNA-Rhodamine-PE labeled-DSPC:Chol:DODMA:PEG-A-DMA | 24 hr | Fluorescent Photomicroscopy |

$1.5 \times 10^6$ Neuro2A cells were administered to each mouse on day 0. When the tumors were of a suitable size (200-400 $mm^3$, typically day 9-12)), mice were randomized and treated with one dose of an SNALP formulation comprising 100 μg siRNA or PBS by intravenous (IV) injection in a total volume of 230 μl. Dose amounts are based on body weight measurements taken on the day of dosing. 24 hours after SPLP administration, the mice were sacrificed, their blood was collected, and the following tissues were collected weighed, immediately frozen and stored at −80 C. until further analysis: tumor, liver (cut in 2 halves), lungs, spleen & heart.

Local distribution of the SNALP was determined by fluorescence microscopy. Accumulation of SNALP is seen in, e.g., the liver, demonstrating the SNALP comprising PEG-dialkyloxypropyls are able to extravasate, i.e., exit the circulation and home to a target tissue or organ.

Pharmacokinetics and Systemic Biodistribution

This example illustrates the pharmacokinetics and biodistribution of SPLPs containing a plasmid encoding luciferase under the control of the CMV promoter (LOSS) and SNALPs containing anti-luciferase siRNA in mice seeded subcutaneously with Neuro2A tumors.

| Group | Mice | Cells | Treatment | Timepoint (h) |
|---|---|---|---|---|
| A | 6 | Neuro2A | [3-H]CHE-L055-DSPC:Chol:DODMA:PEG-A-DMA | 0.25, 1, 4, 8, 24 |
| B | 6 | Neuro2A | [3-H]CHE-anti-luc siRNA-DSPC:Chol:DODMA:PEG-A-DMA | 0.25, 1, 4, 8, 24 |
| C | 6 | Neuro2A | [3-H]CHE-L055 -DSPC:Chol:DODMA:PEG-C-DMA | 0.25, 1, 4, 8, 24 |
| D | 6 | Neuro2A | [3-H]CHE-L055-pSPLP (PEI) | 0.25, 1, 4, 8, 24 |
| E | 6 | Neuro2A | [3-H]CHE-L055-DSPC:Chol:DODMA:PEG-DSG | 0.25, 1, 4, 8, 24 |

All samples are to be provided at 0.5 mg/ml nucleic acid. The following SPLP and SNALP formulations were prepared:
A. [$^3$H] CHE-L055-DSPC:Chol:DODMA:PEG-A-DMA (20:55:15:10)
B. [$^3$H] CHE-anti-luc siRNA-DSPC:Chol:DODMA:PEG-A-DMA (20:55:15:10)
C. [$^3$H] CHE-L055-DSPC:Chol:DODMA:PEG-C-DMA (20:55:15:10)
D. [$^3$H] CHE-L055-pSPLP (PEI) (i.e., precondensed SPLP)
E. [$^3$H] CHE-L055-DSPC:Chol:DODMA:PEG-DSG (20:55:15:10)

| Group | # Mice | Seeding date | Treatment | Injection date | Collection date |
|---|---|---|---|---|---|
| A | 6 | Day 0 | [3-H]CHE-L055-DSPC:Chol:DODMA:PEG-A-DMA | Day 12 | July 31 |
| B | 6 | Day 0 | [3-H]CHE-anti-luc siRNA-DSPC:Chol:DODMA:PEG-A-DMA | Day 12 | July 31 |
| C | 6 | Day 0 | [3-H]CHE-L055 -DSPC:Chol:DODMA:PEG-C-DMA | Day 13 | Day 14 |
| D | 6 | Day 0 | [3-H]CHE-L055-pSPLP (PEI) | Day 13 | Day 14 |
| E | 6 | Day 0 | [3-H]CHE-L055-DSPC:Chol:DODMA:PEG-DSG | Day 14 | Day 15 |

30 male A/J mice (Jackson Laboratories) were seeded subcutaneously with Neuro 2A cells at a dose of $1.5 \times 10^6$ cells in a total volume of 50 μL phosphate buffered saline on day zero. After tumors reached appropriate size (typically on day 9 or later), 200 μl (100 μm nucleic acid) of the SPLP or SNALP preparations described above, were administered intravenously. 0.25, 1, 2, 4, and 8 hours after administration of SPLP or SNALP, mice were weighed and blood (typically 25 μL) was collected by tail nick. 24 hours after administration of SPLP or SNALP, mice were sacrificed, blood was collected and assayed for clearance of [$^3$H]CHE. Organs (e.g., liver, lung, spleen, kidney, heart) and tumors were collected and evaluated for [$^3$H]CHE accumulation. The results are shown in FIGS. 13-16.

For all formulations, SPLP containing PEG-DSG remained in circulation the longest, with 50% of the injected dose remaining after 6 h. Interestingly, there appeared to be a initial rapid clearance of pSPLP within the first 15 minutes that was not seen for any other formulation. After 1 h the clearance profile of the pSPLP was quite similar to SPLP. This initial rapid clearance for the pSPLP sample may indicate that there are actually two types of particles present, one that clears very rapidly and one that behaves very much like SPLP.

Anti-Luc siRNA containing vesicles (SNALP) formulated with the C14 PEG-A-DMA showed more rapid clearance from blood than SPLP containing the C18 PEG-DSG. However, this SNALP formulation showed significantly slower blood clearance than SPLP formulated with the same PEG lipid. A possible reason for this result maybe that siRNA containing particles can evade the cellular immune system more readily than plasmid containing SPLP.

SPLP comprising PEG-C-DMA demonstrated a rapid clearance from blood, which was substantially the same as that observed for SPLP comprising PEG-A-DMA. For both of these formulations, the plasma half lives were approximately 2 h, lower than for SPLP containing C18 PEG-lipids.

SPLP containing PEG-DSG had the highest tumor accumulation at 10.9% inject dose per gram tissue. The two SPLP formulations containing the C14 PEG-lipids, PEG-A-DMA and PEG-C-DMA, had much lower tumor accumulation of 6.1% and 5.9% injected dose per gram tissue. The SiRNA SNALP had slightly more tumor accumulation than an SPLP sample with the same PEG-lipid at 7.3%, which also correlates relatively well with the plasma half-life for this SNALP. The pSPLP formulation had tumor accumulation at 7.5%, which is lower than the comparable PEG-DSG SPLP.

Accumulation of PEG-DSG containing SPLP and pSPLP in the heart and lungs was higher than the other SPLP and SNALP, which is consistent with the increased circulation half lives of particles with C18 PEG-lipids. Not surprisingly, there was an inverse relationship between plasma half-life and accumulation in the liver for all samples tested, while no trend was apparent for sample accumulation in the spleen. Accumulation in the kidneys was very low for all formulations tested, with accumulation between 1.2 and 2.4% injected dose per gram tissue.

Example 9

Silencing of Gene Expression with SNALPS

This example illustrates silencing of gene expression in Neuro 2A tumor bearing mice after co-administration of SPLPs containing a plasmid encoding luciferase under the control of the CMV promoter and SNALPs containing anti-luciferase siRNA.

| Group | # Mice | Tumor | Route | Treatment | Timepoint | Route | # Doses |
|---|---|---|---|---|---|---|---|
| 1 | 3 | Neuro-2a | SQ | PBS/PBS | 48 h | IV | 1 |
| 24A | 4 | | | L055-SPLP/PBS mix | 24 h | | |
| 24B | 4 | | | L055-SPLP/anti-luc siRNA liposomes mix | | | |
| 48A | 4 | | | L055-SPLP/PBS mix | 48 h | | |
| 48B | 4 | | | L055-SPLP/anti-luc siRNA liposomes mix | | | |
| 72A | 4 | | | L055-SPLP/PBS mix | 72 h | | |
| 72B | 4 | | | L055-SPLP/anti-luc siRNA liposomes mix | | | |

| Group | # Mice | Seeding Date | Route | IV Treatment | Timepoint | Injection date | Collection Date |
|---|---|---|---|---|---|---|---|
| 1 | 3 | Day 0 | SQ | PBS/PBS | 48 h | Day 13 | Day 15 |
| 24A | 4 | | | L055-SPLP/PBS mix | 24 h | Day 14 | |
| 24B | 4 | | | L055-SPLP/anti-luc siRNA liposomes mix | | Day 14 | |
| 48A | 4 | | | L055-SPLP/PBS mix | 48 h | Day 13 | |
| 48B | 4 | | | L055-SPLP/anti-luc siRNA liposomes mix | | Day 13 | |
| 72A | 4 | | | L055-SPLP/PBS mix | 72 h | Day 12 | |
| 72B | 4 | | | L055-SPLP/anti-luc siRNA liposomes mix | | Day 12 | |

36 male A/J mice (Jackson Laboratories) were seeded subcutaneously with Neuro 2A cells at a dose of 1.5×10⁶ cells in a total volume of 50 μL phosphate buffered saline on day zero. Once tumors reached appropriate size (typically on day 9 or later), 200-240 μl PBS, SPLP, or SNALP formulations (100 μg nucleic acid total) prepared as described in Example 6 above, were administered intravenously. 24, 48, or 72 after administration of PBS, SPLP or a mixture of SPLP and SNALP, mice were sacrificed and organs (e.g., liver, lung, spleen, kidney, heart) and tumors were collected and evaluated for luciferase activity. The results are shown in FIGS. 18-22.

The results demonstrate that co-administration of pL055 SPLP and anti-luc siRNA SNALP (both containing PEG-A-DMA) maximally decreases luciferase gene expression by 40% forty-eight hours after a single iv dose.

Example 10

Down Regulation of β-Gal Activity in Stably Transfected CT26-CL25 Cells

SNALP were prepared containing siRNA duplex directed against the β-Galactosidase reporter gene and applied to the β-galactosidase expressing stable cell line: CT26CL25, plated at 2×10⁴ cells/well at a concentration of 1.0 μg/mL siRNA. Cells were exposed to SNALP for 24 hours and β-galactosidase activity was determined after 96 hours. Silencing was observed in 90% of the cells in culture which correlates with silencing of a target protein in 40% of cells in vivo.

Example 11

Liver Distribution of Rhodamine Labeled SNALP Following a Single Intravenous Administration SNALP were prepared containing siRNA duplex directed against the β-Galactosidase reporter gene using and administered to A/J mice intravenously, through the tail vein. Tissues were collected at 24 hours, snap frozen and sectioned for visualization of SNALP dissemination. Cells were stained with rhodamine and counterstained with DAPI, which stains nuclei. The in vivo biodistribution of the SNALP favors the liver, with as much as 50% of the administered SNALP material delivered to the liver. The SNALP delivered to the liver is found in a diffuse pattern, distributed throughout the liver.

Example 12

Figure 23:
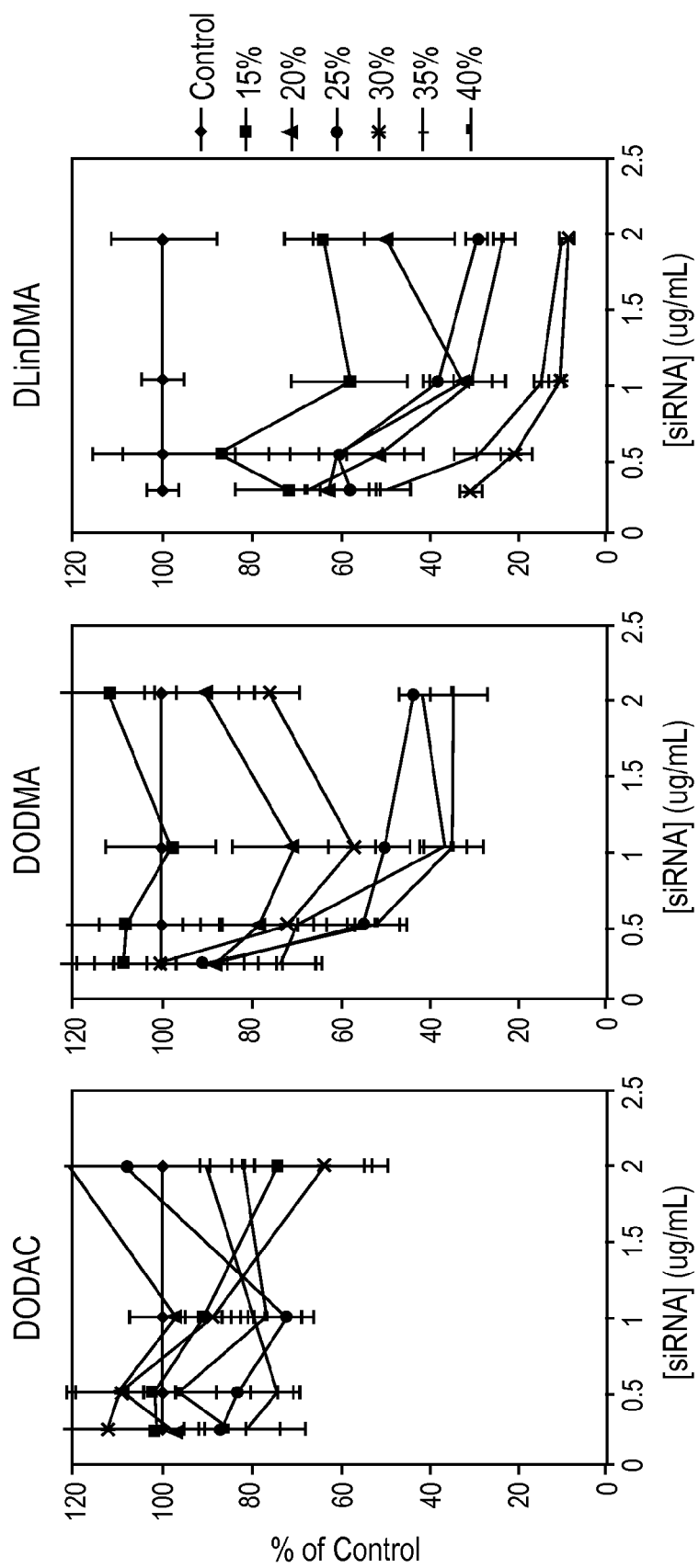
FIG. 23 illustrates data showing silencing of gene expression following in vitro transfection of Neuro2a cells stably expressing luciferase by an SPLP (i.e., SNALP) comprising DODAC, DODMA, or DLinDMA and encapsulating an anti-luciferase siRNA sequence.

Silencing of Gene Expression Following Delivery of siRNA Encapsulated in SPLP Comprising Cationic Lipids This example describes experiments comparing expression of nucleic acids following in vitro transfection of Neuro2A cells with SNALP comprising: (1) DODAC, DODMA, or DLinDMA; (2) PEG-C-DMA; and (3) an siRNA duplex directed against luciferase encapsulated in the SNALP (i.e., siRNA comprising the following sequence: GAUUAUGUCCGGUUAUGUAUU (SEQ ID NO:1) and targeting the DNA sequence complementary to: GATTATGTCCGGTTATGTATT (SEQ ID NO:3)). Neuro2A cells were stably transfected with a plasmid encoding luciferase under the control of the CMV promoter (pLO55). The stably transfected cells were then transfected with SNALP comprising: 15, 20, 25, 30, 35, or 40% of DODAC, DODMA, or DLinDMA; 2% PEG-C-DMA, and an siRNA duplex directed against luciferase encapsulated in the SNALP. Luciferase protein expression was measured 48 hours after transfection with SNALP. SNALP comprising 30% DLinDMA was more effective in reducing luciferase expression in the Neuro2A cells than SNALP comprising DODAC or DODMA were. These results are shown in FIG. 23.

DLinDMA, the most fusogenic lipid with the lowest apparent phase transition temperature, yielded the greatest knockdown when incorporated in SNALP, with luciferase expression only 21% that of the untreated control. This was followed by the DLenDMA formulation (32%), and DODMA (54%). The close correspondence between knockdown efficiency and the $H_{II}$ phase forming ability of the cationic lipid as observed suggests that the two parameters are linked.

Example 13

SNALP Containing Unsaturated Cationic Lipids Show Increased Gene-Silencing Activity The ability of SNALP containing each of the four cationic lipids (i.e., DSDMA, DODMA, DLinDMA, and DLenDMA) to effect gene silencing in stably transfected Neuro2A cells was evaluated. Neuro2A cells stably transfected to express the luciferase were treated with SNALP containing anti-luciferase siRNA for 48 hours. Gene-silencing efficiency was evaluated by comparing the remaining luciferase activity in these cells to that remaining in cells treated with control SNALP containing mismatch siRNA.

Figure 24:
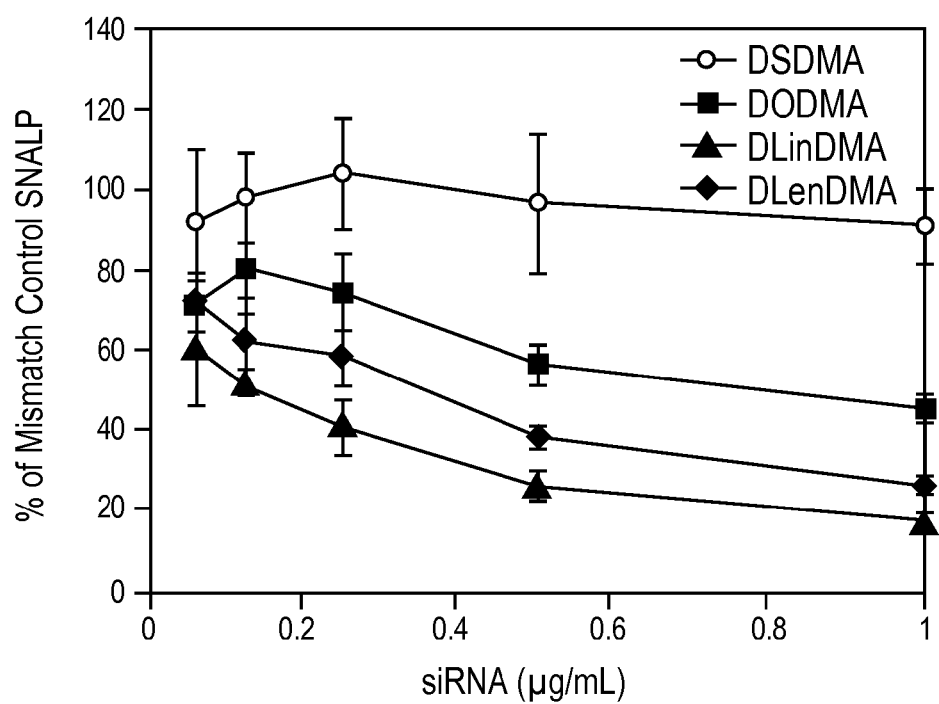
FIG. 24 illustrates data showing SNALP-mediated gene silencing in vitro.

Formulations comprising the saturated lipid DSDMA demonstrated no activity. As unsaturation in the lipid's alkyl chain increased, so did the capacity for RNA interference, with DLinDMA particles yielding an 80% knockdown in gene expression. ³¹P-NMR established DLinDMA as having the lowest phase transition temperature in the series and accordingly, being the most fusogenic lipid. Particles comprising DLenDMA, the most unsaturated lipid, were slightly less efficient than those containing DLinDMA. All results were found to be significant by t-Test (P<0.05 at siRNA concentration of 0.5 μg/mL, and P<0.01 at siRNA concentration of 1.0 μg/mL). Error bars represent standard deviation, n=3. The results are shown in FIG. 24.

Example 14

In Vivo Transfection of Organs by Various SPLP Formulations

This example describes experiments demonstrating in vivo transfection of organs with that SPLP comprising 15% DLinDMA can be used SPLP encapsulating a plasmid encoding luciferase under the control of the CMV promoter were administered to Neuro2A tumor bearing male A/J mice. The SPLP had the following formulations:

| | Sample Description |
|---|---|
| A | SPLP-PEG$_{2000}$-C-DMA |
| | (CHOL:DSPC:DODMA:PEG$_{2000}$-C-DMA 55:20:15:10 mol %) |
| B | SPLP-PEG$_{2000}$ DlinDMA |
| | (CHOL:DSPC:DlinDMA:PEG$_{2000}$-C-DMA 55:20:15:10 mol %) |
| C | SPLP-PEG$_{750}$-C-DMA/DODMA |
| | (CHOL:DSPC:DODMA:PEG$_{750}$-C-DMA 55:20:15:10 mol %) |

-continued

| | Sample Description |
|---|---|
| D | SPLP-PEG$_{750}$-C-DMA/DLinDMA (CHOL:DSPC:DlinDMA:PEG$_{750}$-C-DMA 55:20:15:10 mol %) 0.41 mg/ml |
| E | SPLP- High PEG$_{750}$-C-DMA (CHOL:DSPC:DODMA:PEG$_{750}$-C-DMA 50:20:15:15 mol %) |
| F | SPLP- High PEG$_{750}$-C-DMA (CHOL:DSPC:DlinDMA:PEG$_{750}$-C-DMA 50:20:15:15 mol %) |
| G | SPLP-DODAC (CHOL:DSPC:DODMA:PEG$_{2000}$-C-DMA:DODAC 45:20:15:10:10 mol %) 0.35 mg/ml |

Figure 25:
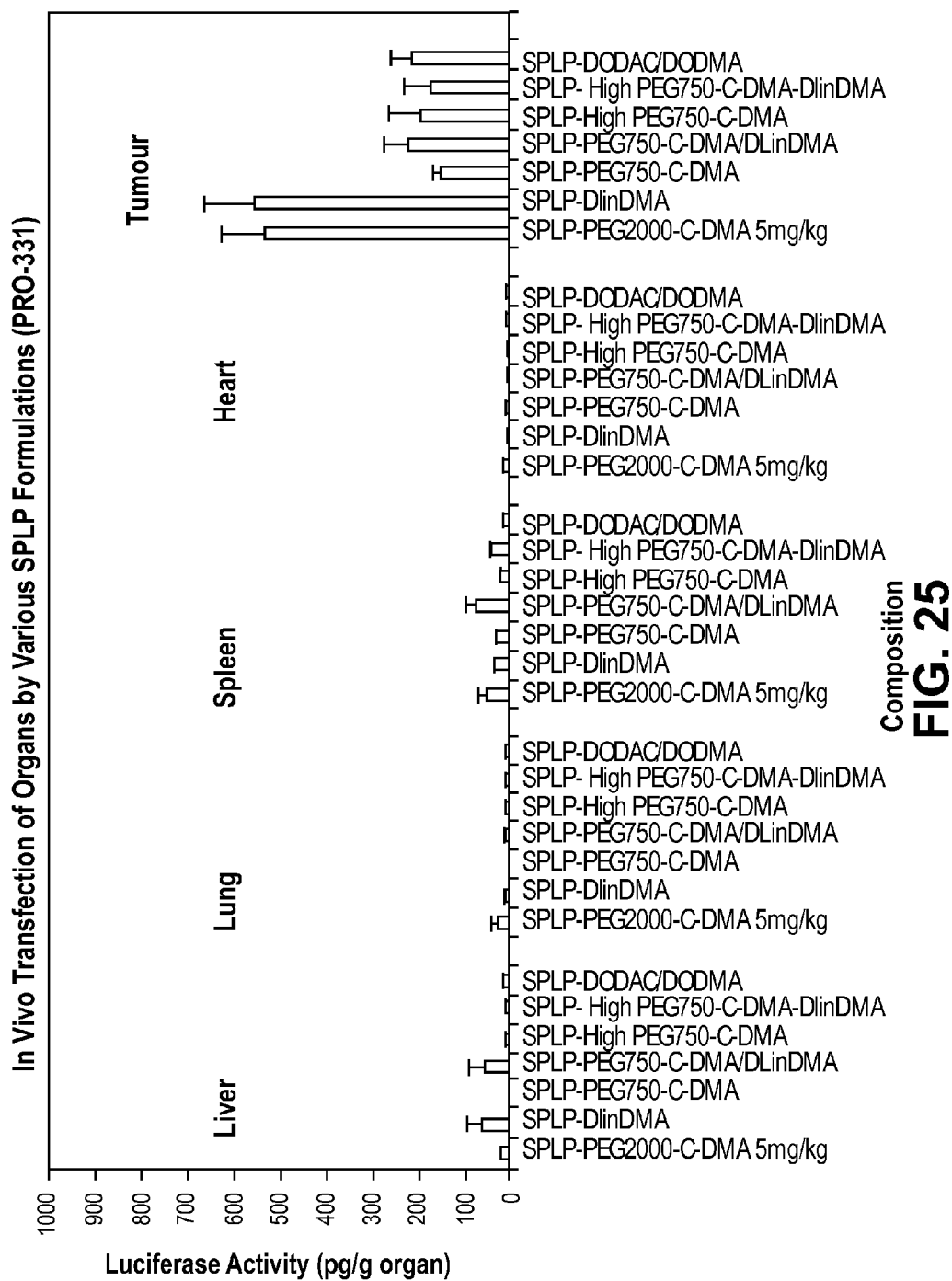
FIG. 25 illustrates data showing luciferase gene expression in tumors 48 hours following intravenous delivery of SPLP encapsulating a plasmid encoding luciferase. The SPLP comprised PEG-C-DMA conjugates and either DODMA or DLinDMA. The PEG moieties had molecular weight of either 2000 or 750.

Luciferase gene expression was assessed in liver, lung, spleen, heart and tumors 48 hours after intravenous administration of the SPLP. The results are shown in FIG. 25.

Example 15

In Vivo Transfection of Tumor by Additional SPLP Formulations

This example describes experiments demonstrating in vivo transfection of organs with that SPLP comprising DLinDMA or DODMA and varying percentages (15%, 10%, 5%, or 2.5%) of PEG-C-DMA. SPLP encapsulating a plasmid encoding luciferase were administered to Neuro2A tumor bearing male A/J mice. The SPLP had the following formulations:

| | Mol % (DSPC:Chol:PEG-C-DMA:DXDMA |
|---|---|
| A | 20:50:15:15 (DODMA) |
| B | 20:55:10:15 (DODMA) |
| C | 20:60:5:15 (DODMA) |
| D | 20:62.5:2.5:15 (DODMA) |
| E | 20:55:10:15 (DLinDMA) |
| F | 20:60:5:15 (DLinDMA) |
| G | 20:62.5:2.5:15 (DLinDMA) |

Figure 26:
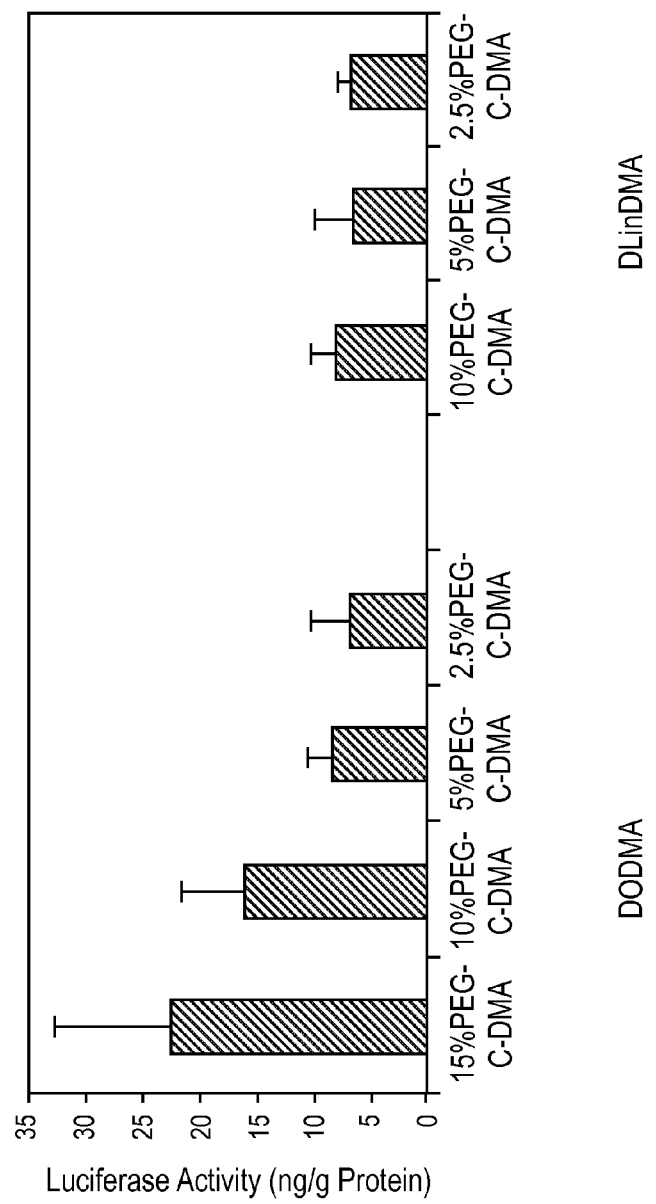
FIG. 26 illustrates data showing luciferase gene expression in Neuro2A tumor bearing male A/J mice 48 hours after intravenous administration of SPLP encapsulating a plasmid encoding luciferase. The SPLP comprised varying percentages (i.e., 15%, 10%, 5% or 2.5%) of PEG-C-DMA and either DODMA or DLinDMA.

Luciferase gene expression was assessed in tumors 48 hours after intravenous administration of SPLP. The results are shown in FIG. 26.

Example 16

Blood Clearance of Lipid Vesicles Comprising PEG-C-DMA

This example describes experiments conducted to assess the blood clearance rate of lipid vesicles comprising various percentages of PEG-C-DMA. A single intravenous dose of $^3$H—CHE-labeled SPLP, SNALP, or empty vesicles was administered to male A/J mice. SPLP comprised the cationic lipid DODMA and SNALP comprised the cationic lipid DLinDMA. The lipid vesicles had the following formulations:

| Group | Treatment | Mol % (DSPC:Chol:PEG-C-DMA:Cationic Lipid) |
|---|---|---|
| A | Empty vesicles | 20:48:2:30 |
| B | SNALP (DlinDMA, PEG-C-DMA) | 20:48:2:30 |
| C | SNALP (DlinDMA, PEG-C-DMA) | 20:55:5:20 |
| D | SPLP (15 mol % PEG-C-DMA) | 20:50:15:15 |
| E | SPLP (10 mol % PEG-C-DMA) | 20:55:10:15 |
| F | SPLP (5 mol % PEG-C-DMA) | 20:60:5:15 |

Figure 27:
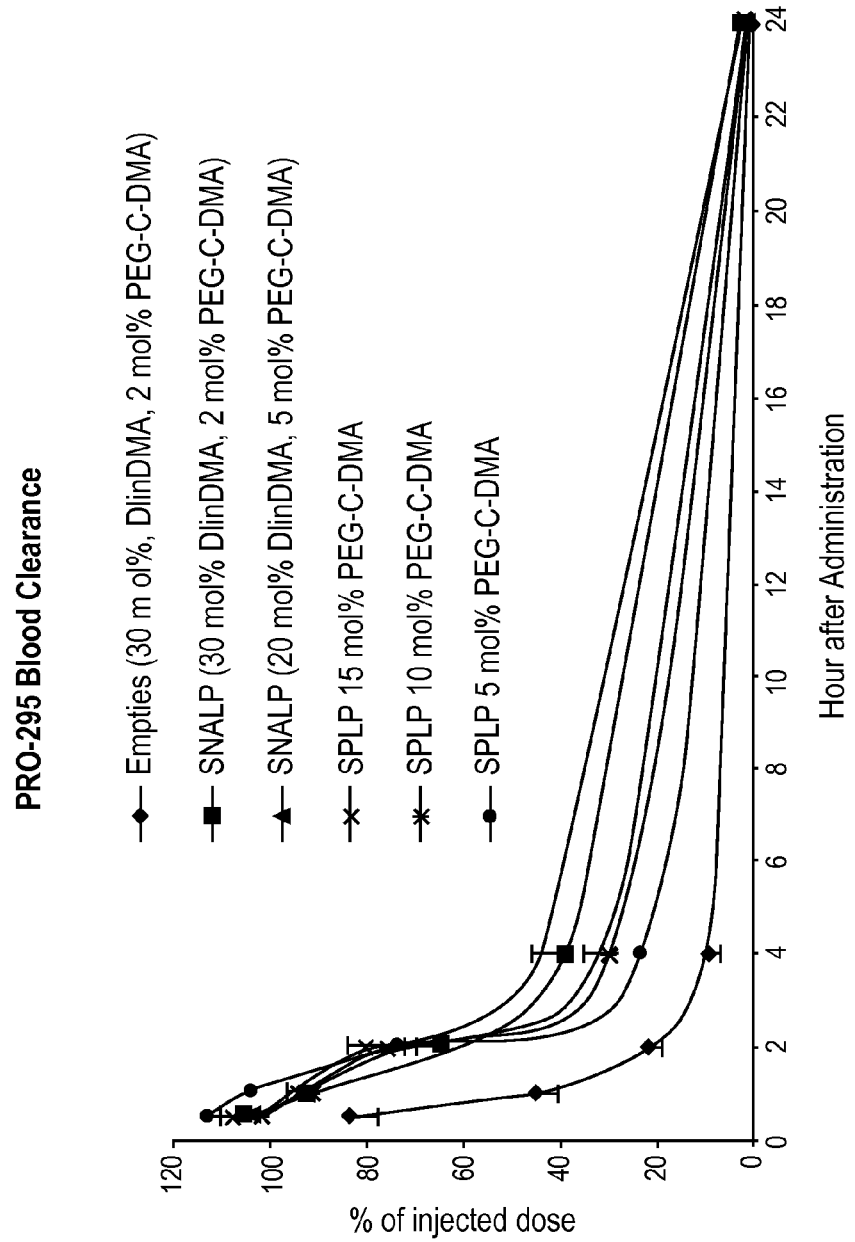
FIG. 27 illustrates data showing the percentage of the injected dose of SPLP, SNALP, or empty vesicles remaining in plasma of male A/J mice following a single intravenous administration of $^3$H—CHE-labeled SPLP or SNALP, or empty vesicles, containing various percentages (i.e., 2%, 5%, 10%, or 15%) of PEG-C-DMA.

The percentage of the injected dose of lipid vesicle remaining in plasma of the mice was determined at 1, 2, 4, and 24 hours following the administration of the $^3$H—CHE-labeled SPLP, SNALP, or empty vesicles. The results are shown in FIG. 27.

Example 17

Biodistribution of Lipid Vesicles Comprising PEG-C-DMA

The example describes experiments conducted to assess the biodistribution of lipid vesicles comprising various percentages of PEG-C-DMA. A single intravenous dose of $^3$H—CHE-labeled SPLP, SNALP, or empty vesicles was administered to Neuro 2A tumor bearing male A/J mice. SPLP comprised the cationic lipid DODMA and SNALP comprised the cationic lipid DLinDMA. The lipid vesicles had the following formulations:

| Group | Treatment | Mol % (DSPC:Chol:PEG-C-DMA:Cationic Lipid) |
|---|---|---|
| A | Empty vesicles | 20:48:2:30 |
| B | SNALP (DlinDMA, PEG-C-DMA) | 20:48:2:30 |
| C | SNALP (DlinDMA, PEG-C-DMA) | 20:55:5:20 |
| D | SPLP (15 mol % PEG-C-DMA) | 20:50:15:15 |
| E | SPLP (10 mol % PEG-C-DMA) | 20:55:10:15 |
| F | SPLP (5 mol % PEG-C-DMA) | 20:60:5:15 |

Figure 28:
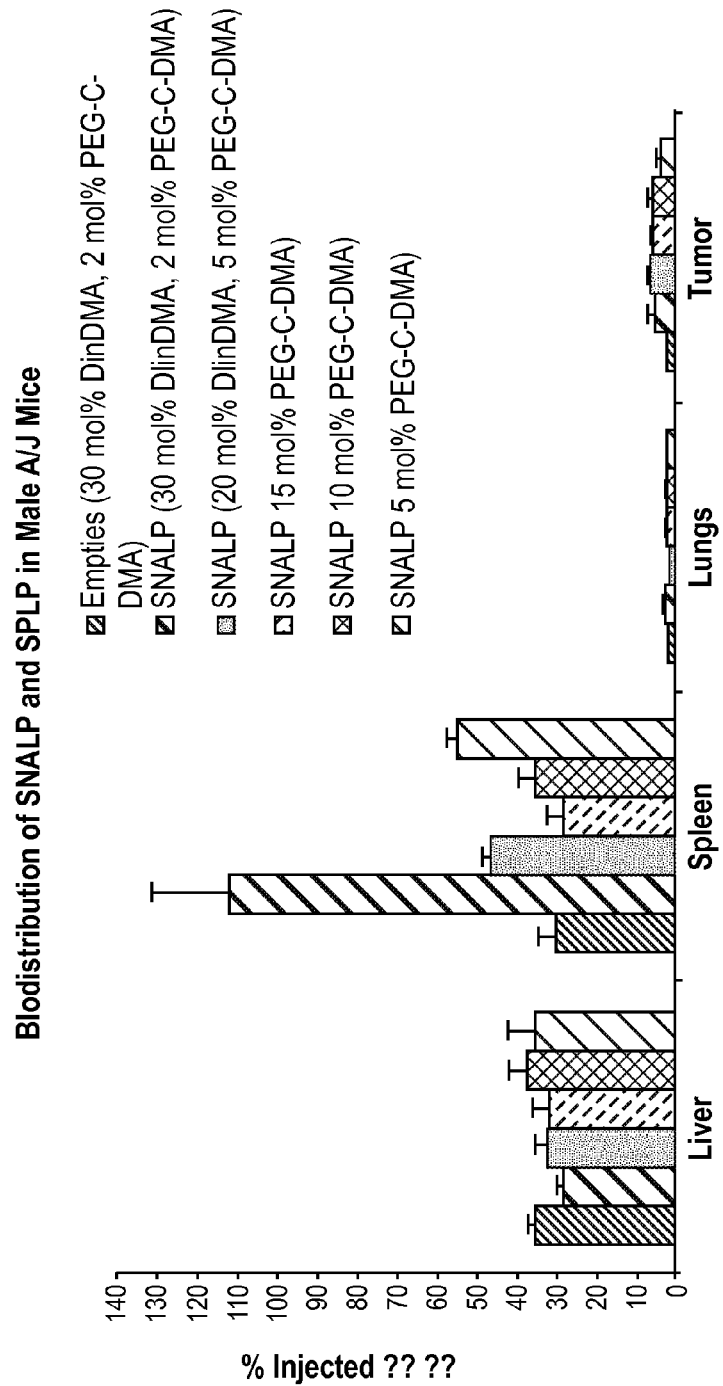
FIG. 28 illustrates data showing the biodistribution SPLP, SNALP or empty vesicles in Neuro-2A tumor-bearing male A/J mice 48 hours after a single intravenous administration of $^3$H—CHE-labelled formulations comprising varying percentages of PEG-C-DMA. The SNALP and empty vesicles comprised DLinDMA. The SPLP comprised DODMA.

The percentage of the injected dose of lipid vesicles was assessed in the liver, spleen, lungs, and tumor of the mice 48 hours after administration of the $^3$H—CHE-labeled vesicles. The results are shown in FIG. 28.

Example 18

Silencing of Gene Expression at a Distal Tumor

This example describes experiments demonstrating gene silencing in distal tumors following administration of SNALP comprising DLinDMA and encapsulating an anti-luciferase siRNA sequence.

Neuro 2A cells were stably transfected with a plasmid encoding luciferase under the control of the CMV promoter (pLO55) to generate Neuro 2A-G cells. Male A/J mice were seeded with the Neuro 2A-G cells. The SNALP encapsulating the anti-luciferase siRNA sequence (i.e., siRNA comprising the following sequence: GAUUAUGUCCG-GUUAUGUAUU (SEQ ID NO:1) and targeting the DNA sequence complementary to: GATTATGTCCGGTTATGT-ATT (SEQ ID NO:3)) were administered to the Neuro2A-G tumor bearing A/J mice intravenously. The SNALP formulations were as follows:

| Group | | Mol % (DSPC:Chol:PEG-C-DAA:DLinDMA) |
|---|---|---|
| | PBS | |
| A | Anti Luciferase SNALP | 20:48:2:30 |
| B | Control (Invert Sequence) SNALP | 20:48:2:30 |
| C | Anti Luciferase SNALP | 20:55:5:20 |
| D | Control (Invert Sequence) SNALP | 20:55:5:20 |
| E | Anti Luciferase SNALP | 20:55:10:15 |
| F | Control (Invert Sequence) SNALP | 20:55:10:15 |

Figure 29:
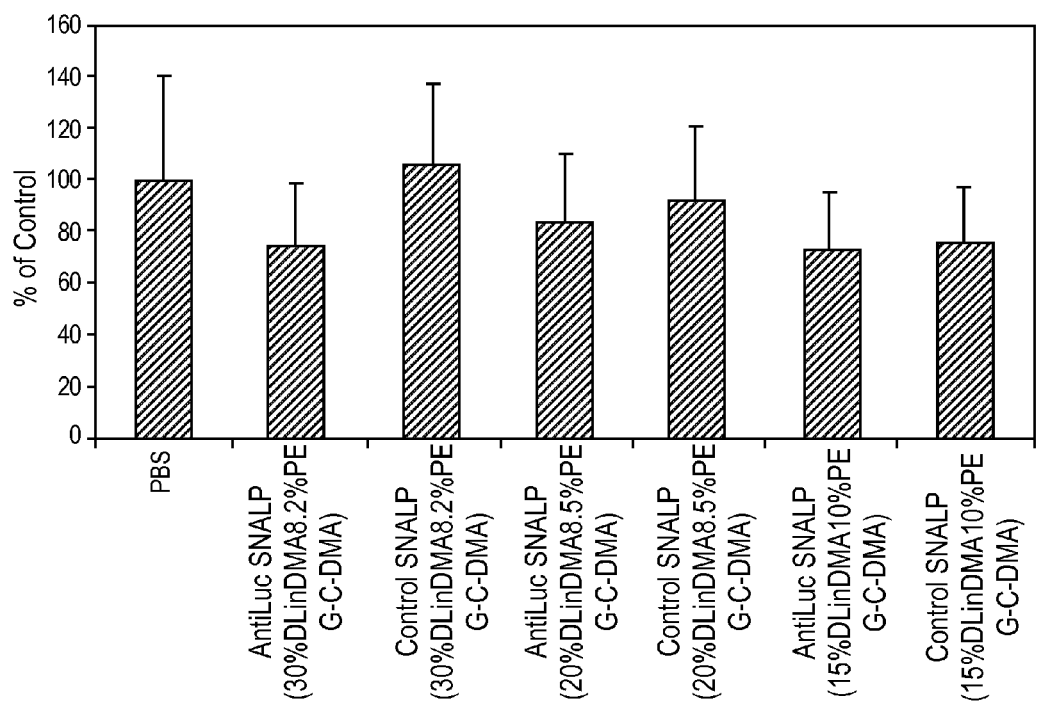
FIG. 29 illustrates data showing silencing of luciferase expression in distal, stable Neuro2A-G tumors in A/J mice 48 hours after intravenous administration of SNALP comprising DLinDMA.

Luciferase gene expression was measured 48 hours following administration of SNALP comprising DLinDMA and encapsulating an anti-luciferase siRNA sequence. The results are shown in FIG. 29.

Example 19

Silencing of Gene Expression in Neuro2A-G Tumor Cells In Vitro

This example describes experiments demonstrating gene silencing in mammalian cells following contact with SNALP comprising DLinDMA and encapsulating an anti-luciferase siRNA sequence described in Example 3 above. Neuro 2A cells were stably transfected with a plasmid encoding luciferase as described in Example 3 above to generate Neuro 2A-G cells. The Neuro 2A-G cell were contacted with SNALP formulations for 24 or 48 hours. The SNALP formulations comprised either PEG-C-DLA ($C_{12}$) or PEG-C-DMA ($C_{14}$) and are as follows:

| Group | Treatment | Mol % (DSPC:Chol:PEG-C-DAA:DLinDMA) |
|---|---|---|
| A | SNALP (PEG-C-DLA) | 20:48:2:30 |
| B | SNALP (PEG-C-DLA) | 20:45:5:30 |
| C | SNALP (PEG-C-DLA) | 20:40:10:30 |
| D | SNALP (PEG-C-DMA) | 20:48:2:30 |

Figure 30:
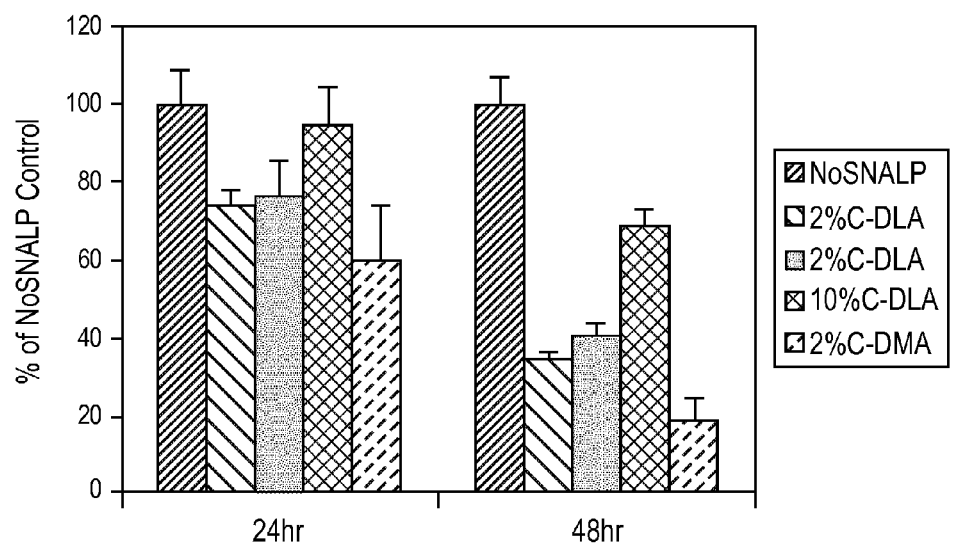
FIG. 30 illustrates data showing silencing of luciferase expression in Neuro2A-G cells following delivery of SNALP formulations comprising DLinDMA and encapsulating anti-luciferase siRNA.

Luciferase gene expression was measured 24 or 48 hours following contacting the Neuro 2A-G cells with SNALP encapsulating an anti-luciferase siRNA sequence. The results are shown in FIG. 30.

Example 20

Silencing of Gene Expression in Neuro2A-G Tumor Cells In Vitro

This example describes experiments demonstrating gene silencing in mammalian cells following contact with SNALP comprising DLinDMA and encapsulating an anti-luciferase siRNA sequence described in Example 3 above. Neuro 2A cells were stably transfected with a plasmid encoding luciferase as described in Example 3 above to generate Neuro 2A-G cells. The Neuro 2A-G cells were contacted with SNALP formulations for 48 hours in the presence and absence of chloroquine. The SNALP formulations contained varying percentages of PEG-C-DMA ($C_{14}$) and either DODMA or DLinDMA. The formulation were as follows:

| Group | Treatment | Mol % (DSPC:Chol:PEG-C-DAA:DLinDMA) |
|---|---|---|
| A | PBS | — |
| B | Naked siRNA | — |
| C | SNALP (PEG-C-DMA) | 20:40:10:30 |
| D | SNALP (PEG-C-DMA) | 20:46:4:30 |
| E | SNALP (PEG-C-DMA) | 20:48:2:30 |
| F | SNALP (PEG-C-DMA) | 20:49:1:30 |

Figure 31:
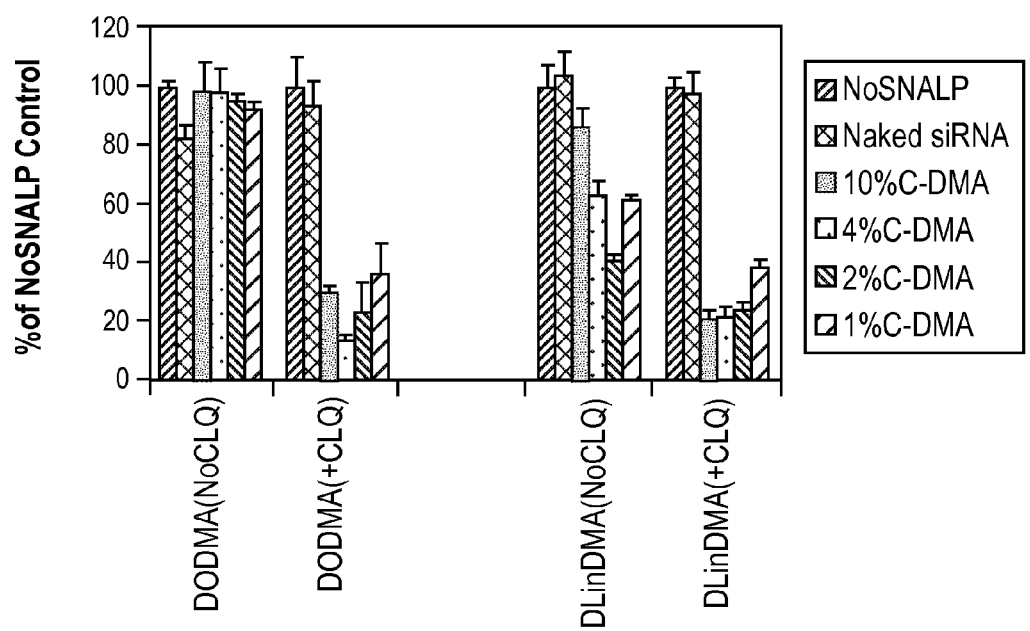
FIG. 31 illustrates data showing silencing of luciferase expression in Neuro2A-G cells following delivery of SNALP formulations comprising DLinDMA and encapsulating anti-luciferase siRNA. Delivery of the SNALP formulations was performed in the absence or presence of chloroquine.

Luciferase gene expression was measured 48 hours following contacting the Neuro 2A-G cells with the SNALP encapsulating an anti-luciferase siRNA sequence. The results are shown in FIG. 31.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications, patents and PCT publications, and Genbank Accession Nos. are herein incorporated by reference in their entirety for all purposes.

What is claimed is:

1. A method of introducing an interfering RNA into a cell, said method comprising contacting said cell with a nucleic acid-lipid particle comprising
   (a) said interfering RNA;
   (b) a cationic lipid of Formula I having the following structure:

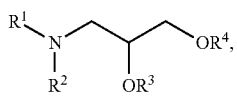

(I)

wherein:
   $R^1$ and $R^2$ are independently selected from the group consisting of: H and $C_1$-$C_3$ alkyl; and
   $R^3$ and $R^4$ are independently selected from the group consisting of alkyl groups having from about 10 to about 20 carbon atoms, wherein at least one of $R^3$ and $R^4$ comprises at least two sites of unsaturation;
   (c) a non-cationic lipid; and
   (d) a conjugated lipid that inhibits aggregation of particles.

2. The method of claim 1, wherein said interfering RNA in said nucleic acid-lipid particle is resistant in aqueous solution to degradation with a nuclease.

3. The method of claim 1, wherein said particle has a median diameter of less than about 150 nm.

4. The method of claim 1, wherein said interfering RNA comprises a small interfering RNA (siRNA).

5. The method of claim 1, wherein said interfering RNA is transcribed from a plasmid.

6. The method of claim 1, wherein said non-cationic lipid is a member selected from the group consisting of dioleoyl-phosphatidylethanolamine (DOPE), palmitoyloleoyl-phosphatidylcholine (POPC), egg phosphatidylcholine (EPC), distearoylphosphatidylcholine (DSPC), palmitoyloleyolphosphatidylglycerol (POPG), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, palmitoyloleoyl-phosphatidylethanolamine (POPE), 1-stearoyl-2-oleoyl-phosphatidyethanolamine (SOPE), cholesterol, and a mixture thereof.

7. The method of claim 1, wherein the conjugated lipid that inhibits aggregation of particles is a member selected from the group consisting of a polyethyleneglycol (PEG)-lipid conjugate, a polyamide (ATTA)-lipid conjugate, and a mixture thereof.

8. The method of claim 1, wherein the conjugated lipid that inhibits aggregation of particles is a polyethyleneglycol (PEG)-lipid.

9. The method of claim 8, wherein the PEG-lipid is member selected from the group consisting of a PEG-diacylglycerol, a PEG-dialkyloxypropyl, a PEG-phospholipid, a PEG-ceramide, and a mixture thereof.

10. The method of claim 1, wherein the conjugated lipid that inhibits aggregation of particles is a polyethyleneglycol (PEG)-dialkyloxypropyl conjugate.

11. The method of claim 10, wherein the PEG-dialkyloxypropyl conjugate is PEG-dimyristyloxypropyl ($C_{14}$).

12. The method of claim 1, wherein said cell is in a mammal.

13. The method of claim 12, wherein presence of said interfering RNA in said cell is detectable for at least 48 hours after said contacting.

14. The method of claim 12, wherein presence of said interfering RNA in said cell is detectable for at least 24 hours after said contacting.

* * * * *

SEQUENCE LISTING

```
<160> NUMBER OF SEQ ID NOS: 3

<210> SEQ ID NO 1
<211> LENGTH: 21
<212> TYPE: RNA
<213> ORGANISM: Artificial Sequence
<220> FEATURE:
```

```
<223> OTHER INFORMATION: Description of Artificial Sequence:
      anti-luciferase siRNA sense sequence

<400> SEQUENCE: 1
gauuaugucc gguuauguau u                                          21

<210> SEQ ID NO 2
<211> LENGTH: 21
<212> TYPE: RNA
<213> ORGANISM: Artificial Sequence
<220> FEATURE:
<223> OTHER INFORMATION: Description of Artificial Sequence:
      anti-luciferase siRNA antisense sequence

<400> SEQUENCE: 2
uacauaaccg gacauaaucu u                                          21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence:
      complementary target DNA sequence

<400> SEQUENCE: 3
gattatgtcc ggttatgtat t                                          21
```